United States Patent
Jaffee et al.

(10) Patent No.: US 11,965,162 B2
(45) Date of Patent: Apr. 23, 2024

(54) MICRORNA AND INHIBITORS THEREOF AND METHODS OF TREATMENT

(71) Applicant: The Johns Hopkins University, Baltimore, MD (US)

(72) Inventors: Elizabeth A. Jaffee, Baltimore, MD (US); Nina Chu, Baltimore, MD (US); Jacquelyn Winifred Zimmerman, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/233,378

(22) Filed: Apr. 16, 2021

(65) Prior Publication Data

US 2021/0324383 A1 Oct. 21, 2021

Related U.S. Application Data

(60) Provisional application No. 63/011,225, filed on Apr. 16, 2020.

(51) Int. Cl.
| | | |
|---|---|---|
| *C12N 15/113* | (2010.01) | |
| *A61K 31/7088* | (2006.01) | |
| *A61K 45/06* | (2006.01) | |
| *A61P 35/00* | (2006.01) | |
| *C12Q 1/6886* | (2018.01) | |

(52) U.S. Cl.
CPC ........ *C12N 15/113* (2013.01); *A61K 31/7088* (2013.01); *A61K 45/06* (2013.01); *A61P 35/00* (2018.01); *C12Q 1/6886* (2013.01); *C12Q 2600/178* (2013.01)

(58) Field of Classification Search
None
See application file for complete search history.

(56) References Cited

U.S. PATENT DOCUMENTS

| | | |
|---|---|---|
| 4,391,904 A | 7/1983 | Litman et al. |
| 5,034,506 A | 7/1991 | Summerton et al. |
| 5,223,409 A | 6/1993 | Ladner et al. |
| 5,288,514 A | 2/1994 | Ellman |
| 5,399,363 A | 3/1995 | Liversidge et al. |
| 5,403,484 A | 4/1995 | Ladner et al. |
| 5,466,468 A | 11/1995 | Schneider et al. |
| 5,474,796 A | 12/1995 | Brennan |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,543,158 A | 8/1996 | Gref et al. |
| 5,549,974 A | 8/1996 | Holmes |
| 5,569,588 A | 10/1996 | Ashby et al. |
| 5,571,698 A | 11/1996 | Ladner et al. |
| 5,593,853 A | 1/1997 | Chen et al. |
| 5,605,662 A | 2/1997 | Heller et al. |
| 5,641,515 A | 6/1997 | Ramtoola |
| 5,846,225 A | 12/1998 | Rosengart et al. |
| 9,970,009 B2 | 5/2018 | Bhat et al. |
| 2010/0286232 A1* | 11/2010 | Schmittgen ............. A61P 43/00 435/6.1 |
| 2012/0270928 A1 | 10/2012 | Bhat et al. |

FOREIGN PATENT DOCUMENTS

| | | | |
|---|---|---|---|
| WO | 1991019735 A1 | 12/1991 | |
| WO | 1992000091 A1 | 1/1992 | |
| WO | 1993020242 A1 | 10/1993 | |
| WO | WO-2008036765 A2 * | 3/2008 | ............. A61K 48/00 |

OTHER PUBLICATIONS

Szymonski et al. Cancer 145,2321, pp. 1-32 (Year: 2022).*
Chalret du Rieu et al. Clinical Chemistry 56: 4, 603-612 (Year: 2010).*
Hidalgo, M. Pancreatic cancer., New England Journal of Medicine., (2010), pp. 1605-1622, vol. 362.
Collins et al. Oncogenic KRas is required for both the initiation of maintenance of pancreatic cancer in mice., J Clin Invest., (2012), pp. 639-653, vol. 122.
Di Magliano et al. Roles for KRas in pancreatic tumor development and progression., Gastroenterology., (2013), pp. 1220-1229, vol. 144.
Lou et al. Pancreatic cancer: modulation of KRas, microRNAs, and intracellular communication in the setting of tumor heterogeneity., Pancreas., (2013), pp. 1218-1226, vol. 42.
Hingorani et al. Preinvasive and invasive ductal pancreatic cancer and its early detection in the mouse., Cancer Cell., (2003), pp. 437-450, vol. 4.
Kanda et al. Presence of somatic mutations in most early-stage pancreatic intraepithelial neoplasia., Gastroenterology., (2012), vol. 142.
Eser et al. Oncogenic KRas signaling in pancreatic cancer., Br J Cancer., (2014), pp. 817-822.
Von Ahrens et al. The role of stromal cancer-associated fibroblasts in pancreatic cancer., J Hematol Oncol., (2017), vol. 10.
Morris et al. KRas, Hedgehog, Wnt and the twisted developmental biology of pancreatic ductal adenocarcinoma., Nature Reviews Cancer., (2010), pp. 683-695, vol. 10.
Choi et al. Challenges in Ras therapeutics in pancreatic cancer., Semin Cancer Biol., (2019), pp. 101-108, vol. 54.
Bournet et al. Targeting KRas for diagnosis, prognosis, and treatment of pancreatic cancer: hopes and realities., European Journal of Cancer., (2016), pp. 75-83, vol. 54.
Keenan et al. A listeria vaccine and depeltion of T-regulatory cells activate immunity against early stage pancreatic intraepithelial neoplasms and prolong survival of mice., Gastroenterology., (2014), pp. 1784-1794, vol. 146.
Rupainmoole et al. MicroRNA therapeutics: towards a new era of the management of cancer and other diseases., Nature Reviews Drug Discovery., (2017), pp. 203-222, vol. 16.

(Continued)

*Primary Examiner* — Brian Whiteman
(74) *Attorney, Agent, or Firm* — Fox Rothschild LLP

(57) ABSTRACT

In one aspect, compositions are provided for the early diagnosis and treatment of pancreatic ductal adenocarcinoma and include microRNAs, e.g. miR-21 and inhibitors thereof. The treatment compositions can be useful for early detection, and for intercepting developing premalignant pancreatic lesions and other KRAS-driven premalignancies.

22 Claims, 15 Drawing Sheets

(56) References Cited

OTHER PUBLICATIONS

Nana-Sinkam et al. Clinical applications for microRNAs in cancer., Clin Pharmacol Ther., (2013), pp. 98-104,, vol. 93.
Taucher et al. Non-coding RNAs in pancreatic cancer: challenges and opportunities for clinical application., Cell Oncol., (2016), pp. 295-318, vol. 39.
Seto et al. Cobomarsen, an oligonucleotide inhibitor of miR-155, coordinately regulates multiple survival pathways to reduce cellular proliferation and survival in cutaneous T-cell lymphoma., Br J Haematol., (2018), pp. 428-444.
Hingorani et al. Trp53R172H and KRasG12D cooperate to promote chromosomal instability and widely metastatic pancreatic ductal adenocarcinoma in mice., Cancer Cell., (2005), pp. 469-483, vol. 7.
Sheedy, FJ. Turning 21: induction of miR-21 as a key switch in the inflammatory response., Frontiers in Immunology., (2015), vol. 6.
Cui et al. MicroRNA-224 promotes tumor progression in nonsmall cell lung cancer., Proc Natl Acad Sci USA., (2015), pp. E4288-E4297, vol. 112.
Luo et al. GAGE: generally applicable gene set enrichment for pathway analysis., BMC Bioinformatics., (2009), vol. 10.
Nagano et al. Shisa2 promotes the maturation of somitic precursors and transition to the segmental fate in Xenopus embryos., Development., (2006), pp. 4643-4654, vol. 133.
Stehbens et al. FGFR2-activating mutations disrupt cell polarity to potentiate migration and invasion in endometrial cancer cell models., J Cell Sci., (2018).
Criscitiello et al. Targeting FGFR pathway in breast cancer., Breast Cancer Innov Res Manag., (2017), pp. 819-822, vol. 37.
Rucki et al. Heterogeneous stromal signaling within the tumor microenvironment controls the metastasis of pancreatic cancer., Cancer Research., (2017), pp. 41-52, vol. 77.
Hagedorn et al. Locked nucleic acid: modality, diversity, and drug discovery., Drug Discovery Today., (2018), pp. 101-114, vol. 23.
Aran et al. xCell: digitally portraying the tissue cellular heterogeneity landscape., Genome Biology., (2017), vol. 18.
Luo et al. MiRNA-21 mediates the antiangiogenic activity of metformin through targeting PTEN and SMAD7 expression and PI3K/AKT pathway., Sci Rep., (2017).
Xue et al. MIR-21 and miR-155 promote non-small cell lung cancer progression by downregulating SOCS1, SOCS6, and PTEN., Oncotarget., (2016), p. 84508-84519, vol. 7.
Frankel et al. Programmed cell death 4 (PDCD4) is an important functional target of the microRNA miR-21 in breast cancer cells., J Biol Chem., (2008), pp. 1026-1033, vol. 283.
Zhao et al. miR-21 promotes EGF-induced pancreatic cancer cell proliferation by targeting Spry2., Cell Death Discovery., (2018), vol. 9.
Zhu et al. MicroRNA-21 targets the tumor suppressor gene tropomyosin 1 (TPM1)., J Biol Chem., (2007), p. 14328-14336, vol. 282.
Shi et al. KRas induces lung tumorigenesis through microRNAs modulation article., Cell Death Discovery., (2018), vol. 9.
Gong et al. MIR-21/RASA1 axis affects the malignancy of colon cancer cells via Ras pathways., World J Gastroenterology., (2015), pp. 1488-1497, vol. 21.
Petrova et al. The hypoxic tumour microenvironment., Oncogenesis., (2018), vol. 10.
He et al. Hypoxia-inducible microRNA-224 promotes the cell growth, migration and invasion by directly targeting RASSF8 in gastric cancer., Mol Cancer., (2017), vol. 16.
Scisciani et al. Transcriptional regulation of miR-224 upregulated in human HCCs by NFkB inflammatory pathways., J Hepatology., (2012), pp. 855-861, vol. 56.
Zhu et al. MicroRNA-224 promotes pancreatic cancer cell proliferation and migration by targeting the TXNIP-mediated HIF1a pathway., Cell Physiol Biochem., (2018), pp. 1735-1746, vol. 48.
Medina et al. OncomiR addiction in an in vivo model of microRNA-21-induced pre-B-cell lymphoma., Nature., (2010), pp. 86-90.
Hatley et al. Modulation of KRas-dependent lung tumorigenesis by microRNA-21., Cancer Cell., (2010), pp. 282-293, vol. 18.

Yu et al. MicroRNA alterations of pancreatic intraepithelial neoplasias., Clin Cancer Research., (2012), pp. 981-992, vol. 18.
Du Rieu et al. MicroRNA-21 is induced early in pancreatic ductal adenocarcinoma precursor lesions., Clin Chem., (2010), pp. 603-612, vol. 56.
Qu et al. Circulating miRNA-21-5p as a diagnostic biomarker for pancreatic cancer: evidence from comprehensive miRNA expression profiling analysis and clinical validation., Sci Rep., (2017), pp. 1-12, vol. 7.
Goto et al. An elevated expression of serum exosomal microRNA-191, -21, -451a of pancreatic neoplasm is considered to be efficient diagnostic marker., BMC Cancer., (2018), pp. 1-11, vol. 18.
Ali et al. Contribution of microRNAs in understanding the pancreatic tumor microenvironment involving cancer associated stellate and fibroblast cells., Am J Cancer Research., (2015), pp. 1251-1264, vol. 5.
Kunita et al. MicroRNA-21 in cancer-associated fibroblasts supports lung adenocarcinoma progression., Sci Rep., (2018), vol. 8.
Wang et al. MIR-21 overexpression enhances TGF-B1-induced epithelial-to-mesenchymal transition to target smad7 and aggravates renal damage in diabetic nephropathy., (2014), pp. 163-172.
Liu et al. miR-21 mediates fibrogenic activation of pulmonary fibroblasts and lung fibrosis., J Exp Med., (2010), pp. 1589-1597.
Ren et al. Extracellular vesicles secreted by hypoxia pre-challenged mesenchymal stem cells promote non-small cell lung cancer cell growth and mobility as well as macrophage M2 polarization via miR-21-5p delivery., J Exp Clin Cancer Res., (2019), vol. 38.
Zhou et al. Exosomes released from tumor-associated macrophages transfer miRNAs that induce a Treg/Th17 cell imbalance in epithelial ovarian cancer., Cancer Immunol Research., (2018), pp. 1578-1592, vol. 6.
Li et al. MicroRNA-155 and microRNA-21 promote the expansion of functional myeloid-derived suppressor cells., J Immunology., (2014), pp. 1034-1043, vol. 192.
Foley et al. Semaphorin 3D autocrine signaling mediates the metastatic role of annexin A2 in pancreatic cancer., Sci Signaling., (2015), vol. 8.
Walter et al. Pancreatic cancer associated fibroblasts display normal allelotypes., Cancer Biol Therapeutics., (2008), pp. 882-888, vol. 7.
Schindelin et al. Fiji: an open-source platform for biological-image analysis., Nature Methods., (2012), pp. 676-682, vol. 9.
Li et al. RSEM: accurate transcript quantification from RNA-Seq data with or without a reference genome., BMC Bioinformatics., (2011), vol. 12.
Leng et al. EBSeq: an empirical Bayes hierarchical model for inference in RNA-seq experiments., Bioinformatics., (2013), pp. 1035-1043, vol. 29.
Thorsson et al. The immune landscape of cancer., Immunity., (2018), pp. 812-830, vol. 48.
Liu et al. An integrated TCGA pan-cancer clinical data resource to drive high-quality survival outcome analytics., Cell., (2018), pp. 400-416, vol. 173.
Klinkhammer et al. PDGF in organ fibrosis., Mol Aspects Med., (2018), pp. 44-62, vol. 62.
Xia et al. Anti-tumor effects of DNA vaccine targeting human fibroblast activation protein a by producing specific immune responses and altering tumor microenvironment in the 4T1 murine breast cancer model., Cancer Immunol Immunotherapies., (2016), pp. 613-624.
Rhim et al. EMT and dissemination precede pancreatic tumor formation., Cell., (2012), pp. 349-361, vol. 148.
Straarup et al. Short locked nucleic acid antisense oligonucleotides potently reduce apolipoprotein B mRNA and serum cholesterol in mice and non-human primates., Nucleic Acids Research., (2010), pp. 7100-7111, vol. 38.
Seppala et al. Patient-derived organoid pharmacotyping is a clinically tractable strategy for precision medicine in pancreatic cancer., Ann Surg., (2020), pp. 427-435.
Baker et al. Modeling pancreatic cancer with organoids., Trends in Cancer., (2016), pp. 176-190, vol. 2.
Moreira et al. Pancreas 3D organoids: current and future aspects as a research platform for personalized medicine in pancreatic cancer., Cmgh., (2018), pp. 289-298, vol. 5.

(56) References Cited

OTHER PUBLICATIONS

Boj et al. Organoid models of human and mouse ductal pancreatic cancer., Cell., (2015), pp. 324-338, vol. 160.

Tiriac et al. Successful creation of pancreatic cancer organoids by means of EUS-guided fine-needle biopsy sampling for personalized cancer treatment., Gastrointest Endosc., (2018), pp. 1474-1480, vol. 87.

Tsai et al. Development of primary human pancreatic cancer organoids, matched stromal and immune cells and 3D tumor microenvironment models., BMC Cancer., (2018), vol. 18.

Chu et al. Inhibition of miR-21 regulates mutant KRas effector pathways and intercepts pancreatic ductal adenocarcinoma development., Cancer Preventation Research., (2020). models of human and mouse ductal pancreatic cancer., Cell., (2015), pp. 324-338, vol. 160.

Dweep et al. MiRWalk—database: prediction of possible miRNA binding sites by walking the genes of three genomes., J Biomed Informatics., (2011), pp. 839-847, vol. 44.

Dweep et al. MiRWalk2.0: a comprehensive atlas of microRNA-target interactions., Nature Methods., (2015), vol. 12.

Jiang et al. Role of programmed cell death 4 in diseases: a double-edged sword., Cell Mol Immunology., (2017), pp. 884-886, vol. 14.

Koutsioumpa et al. MKAD-21 Suppresses the Oncogenic Activity of the miR-21/PPP2R2A/ERK Molecular Network in Bladder Cancer., Molecular Cancer Therapeutics, 17(7), pp. 1430-1440 (Jul. 2018).

\* cited by examiner

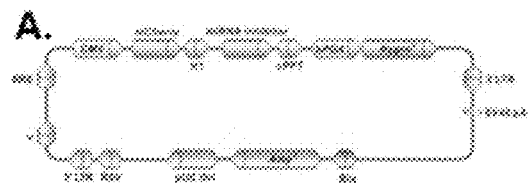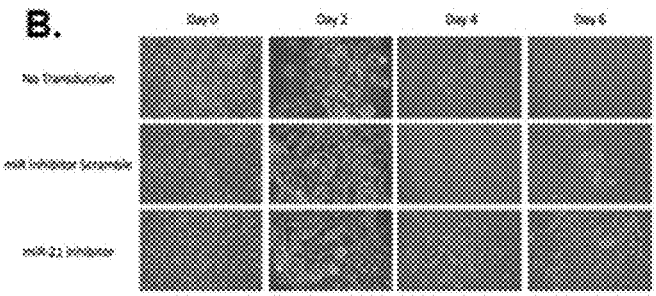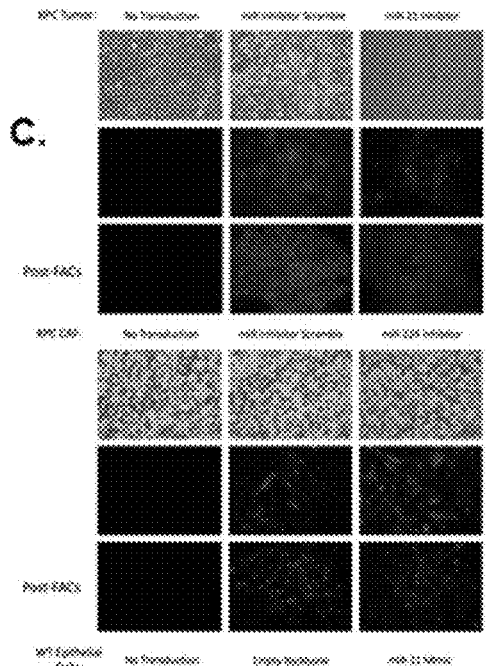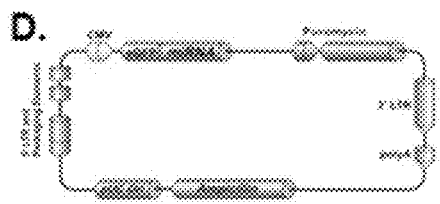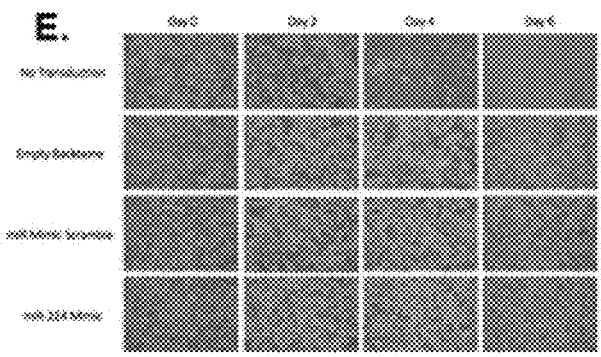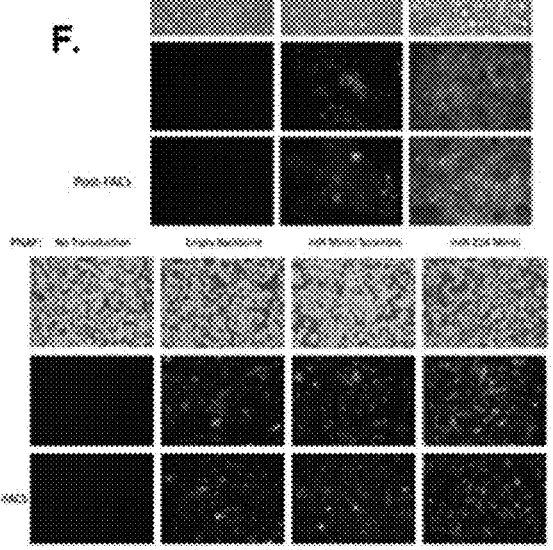
FIGS. 9A-9G

MICRORNA AND INHIBITORS THEREOF AND METHODS OF TREATMENT

CROSS-REFERENCE TO RELATED APPLICATION

This application claims priority to, and the benefit under 35 U.S.C. § 119(e) of U.S. Provisional Application No. 63/011,225, filed Apr. 16, 2020. The entire contents of which are incorporated herein by reference in their entirety.

STATEMENT REGARDING FEDERALLY SPONSORED RESEARCH

This invention was made with government support under grant R01CA184926 awarded by the National Institutes of Health. The government has certain rights in the invention.

FIELD

The present disclosure relates in general to compositions of microRNAs and inhibitors thereof and uses in the treatment of cancer. The disclosure relates in particular to the early intervention and treatment of Pancreatic ductal adenocarcinoma (PDA) and other pancreatic cancers by these microRNAs and inhibitors thereof.

BACKGROUND

Pancreatic ductal adenocarcinoma (PDA) is increasing in incidence, and remains among the deadliest cancers with an overall median survival of 4-6 months[1]. Along with factors such as late diagnosis, poor prognosis results from its complex tumor microenvironment (TME) composed of transformed epithelial cells and tumor-promoting stromal cells that renders PDA refractory to radiation, chemotherapies and immunotherapies[2,3]. The stromal compartment consists of PDA-recruited cancer-associated fibroblasts (CAFs), pancreatic stellate cells, immune cells and extracellular matrix proteins that drive disease progression from the earliest premalignant pancreatic intraepithelial neoplasias (PanINs) to PDA[4].

PDA tumorigenesis is initiated, propagated and maintained by the expression of the driver mutation KRAS (mKRAS)[2,5]. mKRAS is one of the earliest catalytic events and most highly expressed mutation in over 90% of human PanIN1 lesions and PDA[6]. mKRAS persistently activates downstream signaling pathways resulting in increased cell proliferation, survival and metabolic reprogramming[7]. Concurrent to the initiation of PanIN development, mKRAS also triggers the formation of the cancer-supportive microenvironment via recruitment of fibro-inflammatory stroma[2]. These cancer-associated cell populations express additional signals that support PDA development, progression, and metastasis[8,9].

Attempts to develop therapies that directly target mKRAS have been met with challenges[10]. Most strategies have focused on inhibiting mKRAS directly or downstream effectors of mKRAS signaling[10]. However, the clinical benefit of these downstream therapeutics has been limited by compensatory mechanisms, narrow therapeutic windows with associated drug toxicities, the accumulation of additional genetic alterations in tumor cells, and the complexity of signaling by cancer-associated stromal cells[10,11]. Although it is difficult to target mKRAS therapeutically, it may be possible to develop strategies that intercept mKRAS in early premalignancies, before additional genetic and regulatory mechanisms occur[12].

SUMMARY

We now provide new compositions and methods of treatment of cancer in a patient, including a pancreatic cancer.

In particular aspects, we provide compositions for treatment or prevention and early intervention in the treatment of Pancreatic ductal adenocarcinoma (PDA). Methods include the administration of these compositions to a subject.

Accordingly, in certain embodiments, a composition comprises a therapeutically effective amount of a microRNA-21 (miR-21) inhibitor, a miR-224 inhibitor or a combination thereof.

In certain embodiments, a method of preventing or treating pancreatic ductal adenocarcinoma (PDA) in a subject comprises diagnosing the subject as being at a pre-malignant stage or early stages of developing PDA, administering to the subject a composition comprising a therapeutically effective amount of a microRNA-21 (miR-21) inhibitor, a miR-224 inhibitor or a combination thereof, thereby preventing or treating pancreatic ductal adenocarcinoma.

In certain embodiments, dysregulated expression of one or more microRNAs (miRNAs) is detected in a subject at a pre-malignant stage or early stages of developing PDA, as compared to a normal subject. In these and other embodiments, the one or more microRNAs (miRNAs) detected as having a dysregulated expression, comprise: miR-21, miR-16, miR-28, miR-224, miR-28, miR-216b or combinations thereof. In these and other embodiments, detection of dysregulated expression of one or more miRNAs comprising miR-21, miR-16 or miR-28 is diagnostic of a lower-grade premalignant pancreatic intraepithelial neoplasia (PanIN) (P1). In these and other embodiments, detection of dysregulated expression of one or more miRNAs comprising miR-224, miR-28 or miR-216b is diagnostic of higher PanIN grades (P2/3).

The dysregulated or altered expression or function of miR-21 in cells leads to changes in the expression of these key genes and contribute to the development of disease. Introducing miR-21 inhibitors into disease cells or tissues would result in a therapeutic response. In certain embodiments miR-21 inhibitors are used to reduce the activity of miR-21 in a subject, organ, tissue, or cell.

In certain embodiments, the method further comprises detecting in the subject's cells increased expression of KRAS mutations (mKRAS) and/or KRAS activation as compared to a normal control.

In these and other embodiments, a subject is administered a therapeutically effective amount of an miR-21 inhibitor and/or miR-224 inhibitor.

In certain embodiments, the miR-21 inhibitor or the miR-224 inhibitor comprises antibodies, antibody fragments, microRNA mimics, oligonucleotides, polynucleotides, antisense oligonucleotides, siRNAs, enzymes, gene editing agents, nucleases, peptides, polypeptides, small molecules, synthetic compounds, natural compounds or combinations thereof. In certain embodiments, the miR-21 and/or miR-224 inhibitors comprise: microRNA mimics, antisense oligonucleotides, gene editing agents, oligonucleotides, polynucleotides or combinations thereof. In certain embodiments, the oligonucleotides comprise one or more modifications. In certain embodiments, the oligonucleotides comprise a locked nucleic acid (LNA) ribose ring structure and phosphorothioate backbone. In certain embodiments, the miR-21 and/or miR-224 inhibitors are expressed by an expression vector.

In these and other embodiments, the miR-21 and/or miR-224 inhibitors are administered systemically.

In certain embodiments, the method of preventing or treating PDA further comprises administering one or more chemotherapeutic agents to the subject.

In certain embodiments, a vector encodes a microRNA-21 or microRNA-224 inhibitor.

In certain embodiments, an isolated cell comprises a vector encoding a microRNA-21 or microRNA-224 inhibitor.

In certain embodiments, an isolated cell comprises an oligonucleotide encoding a microRNA-21 or microRNA-224 inhibitor.

In certain embodiments, the present compositions and methods are used to treat cancer, including pancreatic cancers and dysplasias. In certain aspects, the pancreatic cancer or dysplasia comprises: ductal adenocarcinoma, pancreatic acinar cell carcinoma, neuroendocrine cell carcinoma, sarcoma of the pancreas, metastatic cancer involving the pancreas, pancreaticoblastoma, or bile duct carcinoma (cholangiocarcinoma). In certain aspects, the pre-cancerous pancreatic state comprises: mucinous cystadenoma, serous cystadenoma, islet cell tumor, mucinous duct ectasia, intraductal papillary mucinous neoplasm, pancreatic intraepithelial neoplasia (PanIN grades 1-3), solid and cystic papillary tumor of the pancreas. In certain aspects, the non-neoplastic condition comprises: pancreatitis, pancreatic pseudocyst, mesothelial cyst, lymphoepithelial cyst of the pancreas, or ischemic necrosis of the pancreas In certain aspects, the present compositions and methods are used to treat an exocrine pancreatic cancer, a pancreatic cystic neoplasm and/or a pancreatic endocrine cancer. In particular, an exocrine pancreatic cancer for treatment may be or instance pancreatic ductal adenocarcinoma (PDAC), adenosquamous carcinoma, squamous cell carcinoma, giant cell carcinoma, acinar cell carcinoma and/pr small cell carcinoma. A pancreatic endocrine cancer for treatment may be for instance insulinomas, glucagonomas, somatostatinomas, gastrinomas, VIPomas and/or non-secreting islet tumors of the pancreas.

Other aspects are described infra.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, certain materials and methods are described herein. In describing and claiming the present invention, the following terminology will be used.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type. Furthermore, to the extent that the terms "including", "includes", "having", "has", "with", or variants thereof are used in either the detailed description and/or the claims, such terms are intended to be inclusive in a manner similar to the term "comprising."

"About" as used herein when referring to a measurable value such as an amount, a temporal duration, and the like, is meant to encompass variations of +/−20%, +/−10%, +/−5%, +/−1%, or +/−0.1% from the specified value, as such variations are appropriate to perform the disclosed methods. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, "biological samples" include solid and body fluid samples. The biological samples used in the present invention can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils, thymus and skin, or samples taken from tumors. Examples of "body fluid samples" include, but are not limited to blood, serum, semen, prostate fluid, seminal fluid, urine, feces, saliva, sputum, mucus, bone marrow, lymph, and tears.

As used herein, "cancer" refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a subject, or may be a non-tumorigenic cancer cell, such as a leukemia cell. Examples of cancer include but are not limited to colon cancer, colorectal cancer, breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

In certain embodiments, the term "cancer", refers to pancreatic associated cancer or anomalies. The pancreatic anomaly may be a pancreatic cancer or dysplasia, pre-cancerous pancreatic state, or non-neoplastic condition. The pancreatic cancer or dysplasia may be pancreatic ductal adenocarcinoma, pancreatic acinar cell carcinoma, neuroendocrine cell carcinoma, sarcoma of the pancreas, metastatic cancer involving the pancreas, pancreaticoblastoma, and bile duct carcinoma (cholangiocarcinoma). The pre-cancerous pancreatic state may be mucinous cystadenoma, serous cystadenoma, islet cell tumor, mucinous duct ectasia, intraductal papillary mucinous neoplasm, pancreatic intraepithelial neoplasia (PanIN grades 1-3), and solid and cystic papillary tumor of the pancreas. The non-neoplastic condition may be pancreatitis, pancreatic pseudocyst, mesothelial cyst, lymphoepithelial cyst of the pancreas, and ischemic necrosis of the pancreas.

As used herein, the term "cancer cells" refer to cells that acquire a characteristic set of functional capabilities during their development, including the ability to evade apoptosis, self-sufficiency in growth signals, insensitivity to anti-growth signals, tissue invasion/metastasis, significant growth potential, and/or sustained angiogenesis. The term "cancer cell" is meant to encompass both pre-malignant and malignant cancer cells.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound tire complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art. Percent homology, sequence identity or complementarity, can be determined by, for example, the Gap program.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above. Diagnosis of a disease according to the present invention can be effected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

As used herein, "dysregulation" or "modulation" means either an increase (stimulation) or a decrease (inhibition) in the expression of a gene or gene product. Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15 M) of salts with inorganic cations such as $Na^{++}$ or $K^{++}$ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1.times. sodium chloride-sodium citrate buffer (SSC)/0.1% (w/v) SDS at 60° C. for 30 minutes.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes: a recombinant DNA which is part of a hybrid gene encoding additional polypeptide sequence, complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like.

The isolated nucleic acid sequences may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

As used in this specification and the appended claims, the term "or" is generally employed in its sense including "and/or" unless the content clearly dictates otherwise.

"Parenteral" administration of an immunogenic composition includes, e.g., subcutaneous (s.c.), intravenous (i.v.), intramuscular (i.m.), or intrasternal injection, or infusion techniques.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

The term "percent sequence identity" or having "a sequence identity" refers to the degree of identity between any given query sequence and a subject sequence.

As used herein, a "pharmaceutically acceptable" component/carrier etc. is one that is suitable for use with humans and/or animals without undue adverse side effects (such as toxicity, irritation, and allergic response) commensurate with a reasonable benefit/risk ratio.

The term "polynucleotide" is a chain of nucleotides, also known as a "nucleic acid" or "nucleic acid sequence" and include, but are not limited to, all nucleic acid sequences which are obtained by any means available in the art, both naturally occurring and synthetic nucleic acids, complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. The nucleic acid sequences may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

As used herein, the term "prevent" refers to the prophylactic treatment of a subject who is at risk of developing a condition resulting in a decrease in the probability that the subject will develop the disorder, and to the inhibition of further development of an already established disorder.

The term "target nucleic acid" sequence refers to a nucleic acid (often derived from a biological sample), to which the oligonucleotide is designed to specifically hybridize. The target nucleic acid has a sequence that is complementary to the nucleic acid sequence of the corresponding oligonucleotide directed to the target. The term target nucleic acid may refer to the specific subsequence of a larger nucleic acid to which the oligonucleotide is directed or to the overall sequence (e.g., gene or mRNA). The difference in usage will be apparent from context.

To "treat" a disease as the term is used herein, means to reduce the frequency or severity of at least one sign or symptom of a disease or disorder experienced by a subject. Treatment of a disease or disorders includes the eradication of cancer.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) eradicating the disease, e.g. cancer; (2) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (3) inhibiting the state, disorder or condition, i.e., arresting, reducing or delaying the development of the disease or a relapse thereof (in case of maintenance treatment) or at least one clinical or subclinical symptom thereof; or (4) relieving the disease, i.e., causing regression of the state, disorder or condition or at least one of its clinical or subclinical symptoms. The benefit to an individual to be treated is either statistically significant or at least perceptible to the patient or to the physician. In some embodiments, with respect to cancer, "treat" means causing remission of the cancer, slowing the course of cancer progression, slowing or inhibiting tumor growth, and/or slowing or inhibiting tumor metastasis. In some embodiments, "treat" means slowing progression of symptoms (e.g., symptoms of pancreatic cancer) or reversing the course of the disease (e.g., the course of pancreatic cancer).

As defined herein, a "therapeutically effective" amount of a compound or agent (i.e., an effective dosage) means an amount sufficient to produce a therapeutically (e.g., clinically) desirable result. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

A "vector" is a composition of matter which comprises an isolated nucleic acid and which can be used to deliver the isolated nucleic acid to the interior of a cell. Examples of vectors include but are not limited to, linear polynucleotides, polynucleotides associated with ionic or amphiphilic compounds, plasmids, and viruses. Thus, the term "vector" includes an autonomously replicating plasmid or a virus. The term is also construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Where any sequence is specifically referred to by an accession number, the sequence is incorporated herein by reference. Information associated with the accession number, such as identification of signal peptide, extracellular domain, transmembrane domain, promoter sequence and translation start, is also incorporated herein in its entirety by reference.

"Genes": All genes, gene names, and gene products disclosed herein are intended to correspond to homologs from any species for which the compositions and methods disclosed herein are applicable. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, are intended to encompass homologous and/or orthologous genes and gene products from other species.

"Ranges": throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Other aspects are disclosed infra.

BRIEF DESCRIPTION OF THE DRAWINGS

FIG. 1A: Schematic of miR-FISH, which detects endogenous miRNA in tissue sections. FIG. 1B: Representative fluorescent images of sections of pancreas stained with either no probe, non-specific scramble-miRNA probe, or U6 positive control probe. No fluorescent signal was observed with no probe or scramble-miRNA probe staining, however strong ubiquitous fluorescent signal was observed upon staining with U6 positive control probe. FIG. 1C: Representative fluorescent images of normal ducts, increasing grades of PanIN lesions, and PDA tissue stained with miR-21. Expression of miR-21 is concentrated in ductal epithelial cells. Displayed below is the quantified image analysis of miR-21 fluorescent signal. FIG. 1D: Representative fluorescent images of normal ducts, increasing grades of PanIN lesions, and PDA tissue stained with miR-224. Expression of miR-224 is concentrated in the stromal compartment surrounding high-grade PanIN2/3 lesions and PDA. Below is the quantified image analysis of miR-224 fluorescent signal. Raw fluorescent signals were quantified by FITC intensity/nuclei. PanIN1, PanIN2/3, and PDA raw signals were normalized to that of normal pancreatic ducts of WT C57BL/6 mice to generate relative signal intensities. (n=4-6 experiments).

FIG. 2A: Relative miR-21 expression in WT pancreatic epithelial cells (WT Ep) and KPC tumor cells transduced with either miR-scramble inhibitor (KPC T Scri) or miR-21 inhibitor (KPC T 21i) compared to expression in non-transduced KPC tumor cells. Relative fold change of miR-21 was quantified using the ΔΔCt method in which all Ct values were first normalized to endogenous control U6 snRNA and all experimental groups were normalized to non-transduced KPC tumor cells (n=3 samples/group, significance was determined by one-way ANOVA). FIG. 2B: Proliferation of non-transduced KPC tumor cells, KPC tumor cells transduced with either miR-scramble inhibitor or miR-21 inhibitor, and media alone (n=3 experiments, significance was determined by two-way ANOVA). FIG. 2C: Migration and FIG. 2D: Invasion of WT pancreatic epithelial cells (WT Ep), non-transduced KPC tumor cells, and KPC tumor cells transduced with either miR-scramble inhibitor or miR-21 inhibitor (n=3 experiments).

FIG. 3A: Relative miR-224 expression in PNAFs and CAFs transduced with either miR-scramble inhibitor (KPC CAF Scri) or miR-224 inhibitor (KPC CAF 224i) compared to expression in non-transduced CAFs. Relative fold change of miR-224 was quantified using the ΔΔCt method in which all Ct values were first normalized to endogenous control U6 snRNA and all experimental groups were normalized to non-transduced KPC CAFs (n=3 samples/group, significance was determined by one-way ANOVA). FIG. 3B: Proliferation assay of non-transduced KPC CAFs, KPC CAFs transduced with either miR-scramble inhibitor or miR-224 inhibitor, and media alone (n=3 experiments, significance was determined by two-way ANOVA). FIG. 3C: Migration and FIG. 3D: Invasion of PNAFs, non-transduced KPC CAFs, and KPC CAFs transduced with either miR-scramble inhibitor or miR-224 inhibitor (n=3 experiments). FIG. 3E: Proliferation assay of non-transduced PNAFs, PNAFs transduced with either empty backbone or miR-224 mimic, and media alone (n=3 samples/group, significance was determined by two-way ANOVA). FIG. 3F: Cell migration was quantified by relative % wound closure after 24 hours for all groups (n=3 experiments, significance was determined by one-way ANOVA). FIG. 3G: Invasion assay of KPC CAFs, non-transduced PNAFs, and PNAFs transduced with either empty backbone (PNAF E.B.) or miR-224 mimic (PNAF+224) (n=5 samples/group).

FIG. 4A: Tumor growth (n=10 mice/group, significance was determined by two-way ANOVA) and FIG. 4B. Percent survival of mice that received subcutaneous tumors of various combinations of KPC tumor cells and CAFs (n=10 mice/group, significance was determined by the log-rank (Mantel-Cox) test). FIG. 4C: % Ki67 positive cells in sections of resected tumors as determined by IHC analysis (n=5 mice/group, significance was determined by one-way ANOVA). Ki67 staining was unsuccessful for the scramble-inhibited tumors (T Scri/CAF Scri) due to necrotic tissue in that treatment group.

FIG. 5A: Red lines indicate the average PanIN stage that was detected in the pancreata of each treatment group (n=at least 7 mice/group, significance was determined by one-way ANOVA). FIG. 5B: Relative fold changes of miR-21 expression and FIG. 5C: miR-224 expression compared to levels in untreated mice. Relative fold changes of miR-21 and miR-224 were quantified using the ΔΔCt method in which all Ct values were first normalized to endogenous control U6 snRNA and all experimental groups were normalized to untreated KPC mice (n=5 mice/group).

FIG. 6A: miR-21 expression is significantly associated with tumor epithelial cell content. P-value for epithelial cell content for hsa-miR-21-3p=8.7e-7; hsa-miR-21-5p=2.1e-13. There is not a significant association between miR-21 expression and tumor fibroblast content. FIG. 6B: miR-224 expression is inversely associated with tumor fibroblast content and associated with epithelial cell content. P-value for fibroblast content for hsa-224-3p=0.022; hsa-224-5p=0.00015. P-value for epithelial content for hsa-224-3p=2.0e-5; hsa-224-5p=0.00021. Plotted miR expression values are variance stabilized.

FIG. 7A: Sorting of PNAFs isolated from a WT C57BL/6 pancreas using PDGFRα. Classic spindle-shaped morphology of fibroblasts is observed post-sort. FIG. 7B: Sorting of KPC CAFs isolated from a primary KPC tumor using FAP. Classic spindle-shaped morphology of fibroblasts is observed post-sort. FIG. 7C: WT C57BL/6 pancreatic epithelial cells from Cell Biologics exhibited a classic cuboidal-shaped morphology. FIG. 7D: Sorting of KPC tumor cells isolated from a primary KPC tumor using EpCAM. Classic cuboidal-shaped morphology of epithelial cells is observed post-sort. FIG. 7E: Representative blots and quantified protein expression of epithelial markers vimentin and E-cadherin in WT pancreatic epithelial cells (WT Ep) and KPC tumor cells (n=4-5 experiments, significance was determined by an unpaired Student t test). FIG. 7F: Representative blots and quantified protein expression of activated fibroblast markers α-SMA and FAP in PNAFs and KPC CAFs (n=4-5 experiments, significance was determined by an unpaired Student t test). FIG. 7G: Cell proliferation was quantified by absorbance at 450 nm using CCK8 every 24 hours up to 72 hrs (n=3 experiments, significance was determined by two-way ANOVA). FIG. 7H: Cell migration was quantified by relative % wound closure after 24 hours (n=2 experiments, significance was determined by one-way ANOVA). All data are mean values±SEM. Statistically significant P values are shown as *, $P<0.05$; , $P<0.01$; * $P<0.001$; **** $P<0.0001$.

FIGS. 9A-9G are a series of fluorescent images, schematic representations and a table. Lentiviral stable transduction of primary cell lines with miR-21 and miR-224 inhibitors and mimics. FIG. 9A: miRNA inhibitor construct for miR-21 and miR-224. FIG. 9B: Hygromycin selection of stably transduced cells achieved at day 6 and onward. Non-transduced KPC tumor cells and CAFs did not survive past day 6. However, cells transduced with scramble and miRNA inhibitor constructs possess hygromycin resistance and remain viable beyond day 6 under selection pressure. FIG. 9C: Transduction efficiency of KPC tumor cells and KPC CAFs post-hygromycin selection visualized by mCherry fluorescence. Sorting further enriched for stably transduced KPC tumor cells evidenced by increased mCherry fluorescence. Sorting maintained high populations of stably transduced KPC CAFs. FIG. 9D: miRNA mimic construct for miR-21 and miR-224. FIG. 9E: Puromycin selection of stably transduced cells achieved at day 6 and onward. Non-transduced WT epithelial cells and PNAFs did not survive past day 6. However, cells transduced with empty backbone, scramble, and miRNA mimic constructs possess puromycin resistance and remain viable beyond day 6 under selection pressure. FIG. 9F: Transduction efficiency of WT epithelial cells and PNAFs post-puromycin selection visualized by eGFP fluorescence. Sorting further enriched for stably transduced WT epithelial cells while maintaining high population of stably transduced PNAFs. FIG. 9G: Summary of lentiviral stable transduction of primary cell lines.

FIG. 10A: Heatmaps of gene expression of biologically relevant and significantly downregulated pathways in miR-21 inhibited KPC tumor cells compared to scramble inhibited KPC tumor cells. FIG. 10B: Heatmaps of gene expression of significantly downregulated pathways in miR-224 inhibited KPC CAFs compared to scramble inhibited KPC CAFs. Red indicates upregulation; blue indicates downregulation. (n=2 samples/group).

FIG. 11B: 5 representative genes of the RAS pathway. FIG. 11C: 5 representative genes of the MAPK pathway. FIG. 11D: 5 representative genes of the mTOR pathway. FIG. 11E: 5 representative genes of the regulation of actin cytoskeleton pathway. FIG. 11F: 5 genes that were significantly dysregulated with miR-224 inhibition in KPC CAFs. FIGS. 11B-11E display genes that were significantly downregulated by miR-21 inhibition in KPC tumor cells. All qPCR fold changes were quantified using the $\Delta\Delta Ct$ method in which all Ct values were first normalized to endogenous control 18S and then to either KPC tumor cells or CAFs transduced with scramble inhibitor (n=2 samples/group).

FIG. 12A: Weights of male and female KPC mice systemically dosed with LNA-scramble inhibitor, LNA-miR-224 inhibitor, or LNA-miR-21 inhibitor. Weights were measured every 5 days over the 6 week treatment regimen (n=5-7 mice/group). FIG. 12B: Table summarizing organ specific toxicities for each inhibitor. Livers, lungs, and kidneys from systemically treated KPC mice were H&E stained and histopathologically assessed by a pathologist for cytotoxicity (n=5 mice/group).

FIG. 13A. Endogenous miR-21 expression in 6 PDOs. FIG. 13B. mCherry reporter in PDOs transduced with a miR-21 inhibitor (miR-21i) or non-specific scramble inhibitor (Scr-i). FIG. 13C. qPCR validation of knockdown efficiency using lentiviral miR inhibitors, date is date of transduction. FIG. 13D. Computational analysis of miR-21 targets. PDCD4 expression is decreased with increased miR-21 expression in TCGA PDAC cohort. x-axis: miR-21 expression; y-axis: target expression.

DETAILED DESCRIPTION

Figures 1A, 1B, 1C, 1D:
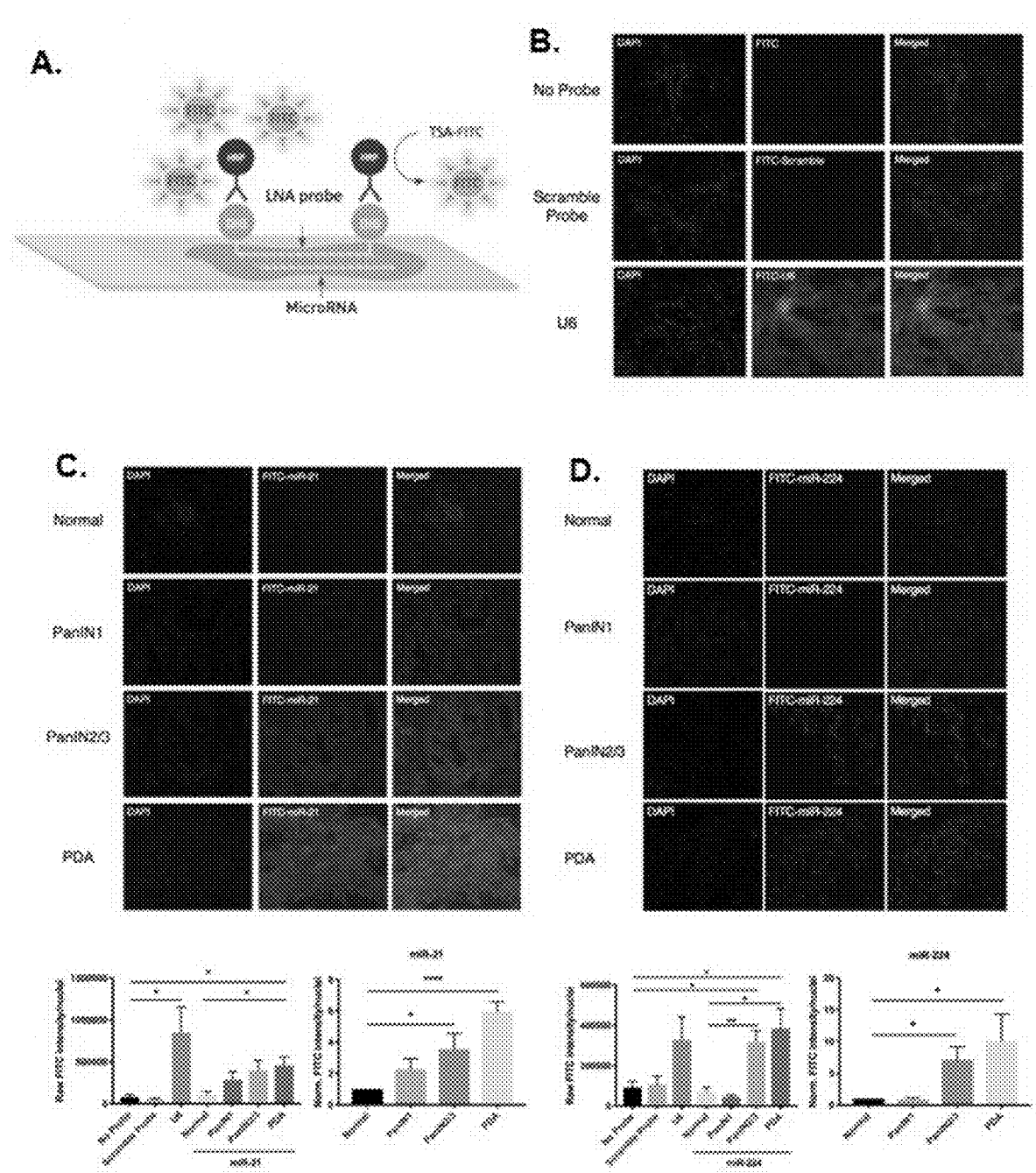
FIGS. 1A-1D are a series of immunofluorescent images, graphs and a schematic representation showing that the miR-FISH analysis quantifies endogenous spatial-temporal expression of miR-21 and miR-224 throughout premalignant progression.

MicroRNAs (miRNAs) are cellular regulators that have been associated with the etiology of many cancers at various stages of development and progression[13,14]. miRNAs are an emerging class of novel therapeutic targets being tested in clinical trials for cancer and other diseases. miRNAs are short non-coding RNAs (ncRNAs), 19-25 nucleotides in length, that post-transcriptionally regulate gene expression by binding to complementary 3' untranslated regions (3'UTR) of target mRNAs resulting in their degradation or translational repression[13,15].

The invention is based, in part, on the discovery that miR-21 and miR-224 are cell-specific and compartment-specific regulators in both PanINs and PDA. In the examples which follow, the results demonstrated that miR-21 is overexpressed in tumor epithelial cells of premalignant ducts, while miR-224 is overexpressed in cancer-associated fibroblasts in PDA stroma. Inhibition of miR-21 reverted pro-tumorigenic functionalities to baseline levels. Overexpression of miR-224 induced activated phenotypes in normal fibroblasts. In vivo miR-21 inhibition improved survival in established PDA. Importantly, early systemic miR-21 inhibition completely intercepted premalignant progression. Finally, an evaluation of miR-21 expression in the PDA cohort of The Cancer Genome Atlas (TCGA) identified a correlation between tumor epithelial cell content and miR-21 expression in human tumors.

Accordingly, in certain embodiments, a method of preventing or treating cancer, for example, pancreatic ductal adenocarcinoma (PDA) in a subject comprises diagnosing the subject as being at a pre-malignant stage or early stages of developing PDA, administering to the subject a composition comprising a therapeutically effective amount of a microRNA-21 (miR-21) inhibitor, a miR-224 inhibitor or a combination thereof, thereby preventing or treating pancreatic ductal adenocarcinoma. The subject or patient may be selected for treatment based on expression and/or dysregulation of expression of one or more miRNAs. In a further aspect, a subject or patient may be selected for treatment based on aberrations in one or more biologic or physiologic pathway(s), including aberrant expression of one or more genes associated with a pathway, or the aberrant expression of one or more protein encoded by one or more gene associated with a pathway. As shown by the results obtained in the examples which follow, inhibition of miR-21 in tumor cells simultaneously downregulated multiple tumorigenic pathways downstream of activated mKRAS. In still a further aspect, a subject or patient may be selected based on aberrations in miRNA expression, or biologic or physiologic pathway(s). A subject may be assessed for sensitivity, resistance, and/or efficacy of a therapy or treatment regime based on the evaluation and/or analysis of miRNA or mRNA expression or lack thereof. Typically, evaluation or assessment may be done by analysis of miRNA and/or mRNA, as well as combination of other assessment methods that include but are not limited to histology, immunohistochemistry, blood work, etc.

In other embodiments, the compositions are used in the treatment of cancer. The subjects can be diagnosed at the early stages by detection of dysregulated miRNAs in the subject as compared to a normal control. The subject or patient may be selected for treatment based on expression and/or dysregulation of expression of one or more miRNAs. In a further aspect, a subject or patient may be selected for treatment based on aberrations in one or more biologic or physiologic pathway(s), including aberrant expression of one or more genes associated with a pathway, or the aberrant expression of one or more protein encoded by one or more gene associated with a pathway. The compositions for use in the treatment of the particular cancer would then include inhibitors or modulators of the dysregulated microRNAs. In the context of this disclosure, pancreatic cancers, in particular, PDAs will be referred to as an example only and is not meant to limit the scope of the invention.

Embodiments of the invention include methods of modulating gene expression, or biologic or physiologic pathways in a cell, a tissue, or a subject comprising administering to the cell, tissue, or subject an amount of an isolated nucleic acid or mimetic thereof comprising an miR-21, miR-21 inhibitor, miR-224 and/or miR-224 inhibitor in an amount sufficient to modulate the expression of a gene positively or negatively modulated by a miR-21 miRNA. A "miR-21 nucleic acid sequence" or "miR-21 inhibitor" includes the full length precursor of miR-21 or complement thereof and related sequences. A "miR-224 nucleic acid sequence" or "miR-224 inhibitor" includes the full length precursor of miR-224 or complement thereof and related sequences.

In certain embodiments, the miR-21 inhibitor or the miR-224 inhibitor comprises antibodies, antibody fragments, microRNA mimics, oligonucleotides, polynucleotides, antisense oligonucleotides, siRNAs, enzymes, gene editing agents, nucleases, peptides, polypeptides, small molecules, synthetic compounds, natural compounds or combinations thereof. In certain embodiments, the miR-21 and/or miR-224 inhibitors comprise: microRNA mimics, antisense oligonucleotides, gene editing agents, oligonucleotides, polynucleotides or combinations thereof. In certain embodiments, the oligonucleotides comprise one or more modifications. In certain embodiments, the oligonucleotides comprise a locked nucleic acid (LNA) ribose ring structure and phosphorothioate backbone. In certain embodiments, the miR-21 and/or miR-224 inhibitors are expressed by an expression vector.

The microRNA inhibitors and microRNA can be purchased commercially or are otherwise available. For example, miR-21 mimic, hsa-miR-21-5p Accession No.: MIMAT0000076, hsa-miR-21-3p Accession No.: MIMAT0004494; The microRNA 21 (*Homo sapiens*; Gene ID: 406991; HGNC:HGNC:31586) The miR-224 (Accession No.: MI0000301); hsa-miR-224-5p (Accession No.: MIMAT0000281) can be purchased from Sigma-Aldrich, LLC. The below table provides various miR-21 oligonucleotides from various species and their accession numbers. An example of an miR-21 inhibitor is miR-21i.

| ID | Accession | RPM | Chromosome | Start | End |
|---|---|---|---|---|---|
| hsa-mir-21 | MI0000077 | 99440 | chr17 | 59841266 | 59841337 |
| mmu-mir-21a | MI0000569 | 38429 | chr11 | 86584067 | 86584158 |
| rno-mir-21 | MI0000850 | 8274 | chr10 | 73902210 | 73902301 |
| dre-mir-21-1 | MI0001908 | 185245 | chr10 | 28198894 | 28199041 |
| dre-mir-21-2 | MI0001909 | 184709 | chr15 | 17373789 | 17373915 |
| ssc-mir-21 | MI0002459 | 77199 | chr12 | 37340385 | 37340476 |
| mml-mir-21 | MI0002621 | 17533 | chr16 | 53341909 | 53341980 |
| ptr-mir-21 | MI0002622 | — | chr17 | 59181943 | 59182014 |
| ggo-mir-21 | MI0002623 | — | chr5 | 23505237 | 23505308 |
| ppy-mir-21 | MI0002624 | — | NW_002962513.1 | 1757121 | 1757192 |
| mne-mir-21 | MI0002625 | — | | | |
| age-mir-21 | MI0002626 | — | | | |
| ppa-mir-21 | MI0002627 | — | chr17 | 58747205 | 58747276 |
| fru-mir-21 | MI0003325 | — | HE602549.1 | 1136596 | 1136668 |
| tni-mir-21 | MI0003326 | — | 7 | 1044906 | 1045027 |
| bta-mir-21 | MI0004742 | 20474 | chr19 | 11138471 | 11138542 |
| gga-mir-21 | MI0004994 | 39260 | chr19 | 7376247 | 7376343 |
| mdo-mir-21 | MI0005275 | 8220 | chr2 | 172169920 | 172169993 |
| cgr-mir-21 | MI0005725 | 115683 | JH000425.1 | 1284121 | 1284212 |
| oan-mir-21 | MI0006883 | 39760 | Ultra324 | 945547 | 945660 |
| cfa-mir-21 | MI0008165 | — | chr9 | 34340550 | 34340609 |
| eca-mir-21 | MI0012776 | 5200 | chr11 | 33863745 | 33863816 |
| tgu-mir-21 | MI0013739 | — | chr19 | 8993795 | 8993866 |
| oar-mir-21 | MI0014116 | 62976 | chr11 | 10336498 | 10336569 |
| aca-mir-21 | MI0018814 | — | GL343470.1 | 228465 | 228531 |
| ola-mir-21-1 | MI0019497 | — | 13 | 24451854 | 24451948 |
| ola-mir-21-2 | MI0019502 | — | 14 | 22568052 | 22568138 |
| sha-mir-21 | MI0019641 | — | GL856812.1 | 2094225 | 2094374 |
| pol-mir-21 | MI0022195 | — | | | |
| ccr-mir-21 | MI0023368 | — | | | |
| aja-mir-21 | MI0024362 | — | | | |
| ipu-mir-21-1 | MI0024567 | — | | | |
| ipu-mir-21-2 | MI0024568 | — | | | |
| hhi-mir-21 | MI0025437 | — | | | |

| ID | Accession | RPM | Chromosome | Start | End |
|---|---|---|---|---|---|
| ssa-mir-21a-1 | MI0026626 | — | | | |
| ssa-mir-21a-2 | MI0026627 | — | | | |
| ssa-mir-21b | MI0026628 | — | | | |
| efu-mir-21 | MI0028851 | — | JH977664.1 | 7640732 | 7640811 |
| chi-mir-21 | MI0030691 | — | chr19 | 10841436 | 10841527 |
| tch-mir-21 | MI0031258 | — | KB320868.1 | 206782 | 206841 |
| oha-mir-21 | MI0031411 | — | AZIM01005944.1 | 49865 | 49945 |

Additional miRNA inhibitors are disclosed for example in U.S. Pat. No. 9,970,009 (inhibitors of miR-21 activity) and US20120270928 (compositions and methods for the inhibition of miR-21 activity). Both U.S. Pat. No. 9,970,009 and US20120270928 are incorporated herein by reference in their entirety.

In certain embodiments, there are synthetic nucleic acids that are miRNA inhibitors. A miRNA inhibitor is between about 17 to 25 nucleotides in length and comprises a 5' to 3' sequence that is at least 90% complementary to the 5' to 3' sequence of a mature miRNA. In certain embodiments, a miRNA inhibitor molecule is 17, 18, 19, 20, 21, 22, 23, 24, or 25 nucleotides in length, or any range derivable therein. Moreover, a miRNA inhibitor may have a sequence (from 5' to 3') that is or is at least 70, 75, 80, 85, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA. One of skill in the art could use a portion of the miRNA sequence that is complementary to the sequence of a mature miRNA as the sequence for a miRNA inhibitor. Moreover, that portion of the nucleic acid sequence can be altered so that it is still comprises the appropriate percentage of complementarity to the sequence of a mature miRNA.

In some embodiments, of the invention, a synthetic miRNA or inhibitor contains one or more design element(s). These design elements include, but are not limited to: (i) a replacement group for the phosphate or hydroxyl of the nucleotide at the 5' terminus of the complementary region; (ii) one or more sugar modifications in the first or last 1 to 6 residues of the complementary region; or, (iii) noncomplementarity between one or more nucleotides in the last 1 to 5 residues at the 3' end of the complementary region and the corresponding nucleotides of the miRNA region. A variety of design modifications are known in the art.

Modified or Mutated Nucleic Acid Sequences: In some embodiments, any of the nucleic acid sequences e.g. microRNAs, microRNA mimics, microRNA inhibitors, antisense oligonucleotides, etc., may be modified or derived from a native nucleic acid sequence, for example, by introduction of mutations, deletions, substitutions, modification of nucleobases, backbones and the like. Examples of some modified nucleic acid sequences envisioned for this disclosure include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N ($CH_3$)—N($CH_3$)—$CH_2$ and O—N($CH_3$)—$CH_2$—$CH_2$ backbones, wherein the native phosphodiester backbone is represented as O—P—O—$CH_2$,). The amide backbones disclosed by De Mesmaeker et al. Acc. Chem. Res. 1995, 28:366-374) are also embodied herein. In some embodiments, the nucleic acid sequences having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. Science 1991, 254, 1497). The nucleic acid sequences may also comprise one or more substituted sugar moieties. The nucleic acid sequences may also have sugar mimetics such as cyclobutyls in place of the pentofuranosyl group.

The nucleic acid sequences may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N^6$ (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278).

Another modification of the nucleic acid sequences of the invention involves chemically linking to the nucleic acid sequences one or more moieties or conjugates which enhance the activity or cellular uptake of the oligonucleotide. Such moieties include but are not limited to lipid moieties such as a cholesterol moiety, a cholesteryl moiety (Letsinger et al., Proc. Natl. Acad. Sci. USA 1989, 86, 6553), cholic acid (Manoharan et al. Bioorg. Med. Chem. Let. 1994, 4, 1053), a thioether, e.g., hexyl-S-tritylthiol (Manoharan et al. Ann. N.Y. Acad. Sci. 1992, 660, 306; Manoharan et al. Bioorg. Med. Chem. Let. 1993, 3, 2765), a thiocholesterol (Oberhauser et al., Nucl. Acids Res. 1992, 20, 533), an aliphatic chain, e.g., dodecandiol or undecyl residues (Saison-Behmoaras et al. EMBO J. 1991, 10, 111; Kabanov et al. FEBS Lett. 1990, 259, 327; Svinarchuk et al. Biochimie 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). It is not necessary for all positions in a given nucleic acid sequence to be uniformly modified, and in fact more than one of the aforementioned modifications may be incorporated in a single nucleic acid sequence or even at within a single nucleoside within a nucleic acid sequence.

In some embodiments, the microRNA molecules or inhibitors thereof, are engineered to comprise one or more modified nucleobases. For example, known modifications of RNA molecules can be found, for example, in Genes VI, Chapter 9 ("Interpreting the Genetic Code"), Lewis, ed. (1997, Oxford University Press, New York), and Modification and Editing of RNA, Grosjean and Benne, eds. (1998, ASM Press, Washington D.C.). Modified RNA components include the following: 2'-O-methylcytidine; $N^4$-methylcytidine; $N^4$-2'-O-dimethylcytidine; $N^4$-acetylcytidine; 5-methylcytidine; 5,2'-O-dimethylcytidine; 5-hydroxymethylcytidine; 5-formylcytidine; 2'-O-methyl-5-formaylcytidine; 3-methylcytidine; 2-thiocytidine; lysidine; 2'-O-methyluridine; 2-thiouridine; 2-thio-2'-O-methyluridine; 3,2'-O-dimethyluridine; 3-(3-amino-3-carboxypropyl)uridine; 4-thiouridine; ribosylthymine; 5,2'-O-dimethyluridine; 5-methyl-2-thiouridine; 5-hydroxyuridine; 5-methoxyuridine; uridine 5-oxyacetic acid; uridine 5-oxyacetic acid methyl ester; 5-carboxymethyluridine; 5-methoxycarbonylmethyluridine; 5-methoxycarbonylmethyl-2'-O-methyluridine; 5-methoxycarbonylmethyl-2'-thiouridine; 5-carbamoylmethyluridine; 5-carbamoylmethyl-2'-O-methyluridine; 5-(carboxyhydroxymethyl)uridine; 5-(carboxyhydroxymethyl) uridinemethyl ester; 5-aminomethyl-2-thiouridine; 5-methylaminomethyluridine; 5-methylaminomethyl-2-thiouridine; 5-methylaminomethyl-2-selenouridine; 5-carboxymethylaminomethyluridine; 5-carboxymethylaminomethyl-2'-O-methyl-uridine; 5-carboxymethylaminomethy 1-2-thiouridine; dihydrouridine; dihydroribosylthymine; 2'-methyladenosine; 2-methyladenosine; $N^6$Nmethyladenosine; $N^6$, $N^6$-dimethyladenosine; $N^6$,2'-O-trimethyladenosine; 2 methylthio-$N^6$Nisopentenyladenosine; $N^6$-(cis-hydroxyisopentenyl)-adenosine; 2-methylthio-$N^6$-(cis-hydroxyisopentenyl)-adenosine; $N^6$-glycinylcarbamoyl)adenosine; $N^6$ threonylcarbamoyl adenosine; $N^6$-methyl-$N^6$-threonylcarbamoyl adenosine; 2-methylthio-$N^6$-methyl-$N^6$-threonylcarbamoyl adenosine; $N^6$-hydroxynorvalylcarbamoyl adenosine; 2-methylthio-$N^6$-hydroxnorvalylcarbamoyl adenosine; 2'-O-ribosyladenosine (phosphate); inosine; 2'O-methyl inosine; 1-methyl inosine; 1,2'-O-dimethyl inosine; 2'-O-methyl guanosine; 1-methyl guanosine; $N^2$-methyl guanosine; $N^2$, $N^2$-dimethyl guanosine; $N^2$, 2'-O-dimethyl guanosine; $N^2$, $N^2$, 2'-O-trimethyl guanosine; 2'-O-ribosyl guanosine (phosphate); 7-methyl guanosine; $N^2$, 7-dimethyl guanosine; $N^2$, $N^2$; 7-trimethyl guanosine; wyosine; methylwyosine; under-modified hydroxywybutosine; wybutosine; hydroxywybutosine; peroxywybutosine; queuosine; epoxyqueuosine; galactosyl-queuosine; mannosyl-queuosine; 7-cyano-7-deazaguanosine; arachaeosine [also called 7-formamido-7-deazaguanosine]; and 7-aminomethyl-7-deazaguanosine.

In another embodiment, the miRNA or miRNA inhibitor nucleic acid sequences comprise one or more nucleotides substituted with locked nucleic acids (LNA). The LNA modified nucleic acid sequences may have a size similar to the parent or native sequence or may be larger or smaller. Such LNA-modified oligonucleotides may contain less than about 70%, or less than about 60%, or less than about 50% LNA monomers and that their sizes are between about 1 and 25 nucleotides.

In one embodiment, an oligonucleotide comprises at least five consecutive bases complementary to a nucleic acid sequence, wherein the oligonucleotide specifically hybridizes to and modulates expression of miR-21 or miR-224 in vivo or in vitro. In another embodiment, the oligonucleotide compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the oligonucleotide. These compounds are then tested using the methods described herein to determine their ability to inhibit expression of a target nucleic acid.

In some embodiments, homology, sequence identity or complementarity, between the oligonucleotide and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another embodiment, an oligonucleotide e.g. microRNA and mimics or inhibitors thereof, comprises combinations of phosphorothioate internucleotide linkages and at least one internucleotide linkage selected from the group consisting of: alkylphosphonate, phosphorodithioate, alkylphosphonothioate, phosphoramidate, carbamate, carbonate, phosphate triester, acetamidate, carboxymethyl ester, and/or combinations thereof.

In another embodiment, an oligonucleotide optionally comprises at least one modified nucleobase comprising, peptide nucleic acids, locked nucleic acid (LNA) molecules, analogues, derivatives and/or combinations thereof.

An oligonucleotide is specifically hybridizable when binding of the compound to the target nucleic acid interferes with the normal function of the target nucleic acid to cause a loss of activity, and there is a sufficient degree of complementarity to avoid non-specific binding of the oligonucleotide to non-target nucleic acid sequences under conditions in which specific binding is desired. Such conditions include, i.e., physiological conditions in the case of in vivo assays or therapeutic treatment, and conditions in which assays are performed in the case of in vitro assays.

An oligonucleotide, whether DNA, RNA, chimeric, substituted etc., is specifically hybridizable when binding of the compound to the target DNA or RNA molecule interferes with the normal function of the target DNA or RNA to cause a loss of utility, and there is a sufficient degree of complementarily to avoid non-specific binding of the oligonucleotide to non-target sequences under conditions in which specific binding is desired, i.e., under physiological conditions in the case of in vivo assays or therapeutic treatment, and in the case of in vitro assays, under conditions in which the assays are performed.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimens for treatment of cells, tissues and animals, especially humans.

In embodiments, oligomeric oligonucleotides, particularly oligonucleotides, bind to target nucleic acid molecules and modulate the expression of molecules encoded by a miR-21 or miR-224 gene comprising one or more variants that would either benefit from a decrease in in miR-21 or miR-224, or whether deletion, substitution or some other mechanism wherein the agent used would be therapeutically beneficial to that particular subject. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The oligonucleotides, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an oligonucleotide to a particular nucleic acid molecule, in the context of this disclosure, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In another embodiment, the antisense oligonucleotides bind to coding and/or non-coding regions of a target polynucleotide and modulate the expression and/or function of the target molecule.

In another embodiment, the antisense oligonucleotides bind to natural antisense polynucleotides and modulate the expression and/or function of the target molecule. In another embodiment, the antisense oligonucleotides bind to sense polynucleotides and modulate the expression and/or function of the target molecule.

In other embodiments, the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non-coding regions.

According to the present disclosure, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleobase positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in certain embodiments, the gene expression is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

In another embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs).

In some embodiments, the ribonucleic acid sequence is specific for regulatory segments of the genome that control the transcription of microRNAs, e.g. miR-21. Thus a candidate therapeutic agent can be a dsRNA that inhibits the expression of miR-21 in a cell and is administered to a patient in need of treatment.

The nucleic acid molecules of the present disclosure can be produced by standard techniques. For example, polymerase chain reaction (PCR) techniques can be used to obtain an isolated nucleic acid containing a nucleotide sequence described herein. Various PCR methods are described in, for example, *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Methods of the disclosure include reducing or eliminating activity of one or more miRNAs in a cell comprising introducing into a cell a miRNA inhibitor (which may be described generally herein as a miRNA, so that a description of miRNA, where appropriate, also will refer to a miRNA inhibitor). The particular nucleic acid molecule provided to the cell is understood to correspond to a particular miRNA in the cell, and thus, the miRNA in the cell is referred to as the "corresponding miRNA." In situations in which a named miRNA molecule is introduced into a cell, the corresponding miRNA will be understood to be the induced or inhibited miRNA or induced or inhibited miRNA function. In cases in which a particular corresponding miRNA is being inhibited by a miRNA inhibitor, the particular miRNA will be referred to as the "targeted miRNA." It is contemplated that multiple corresponding miRNAs may be involved. In particular embodiments, more than one miRNA molecule is introduced into a cell. Moreover, in other embodiments, more than one miRNA inhibitor is introduced into a cell. Furthermore, a combination of miRNA molecule(s) and miRNA inhibitor(s) may be introduced in a cell.

Typically, an endogenous gene, miRNA or mRNA is modulated in the cell. In particular embodiments, the nucleic acid sequence comprises at least one segment that is at least 70, 75, 80, 85, 90, 95, or 100% identical in nucleic acid sequence to one or more miRNA or gene sequence. Modulation of the expression or processing of an endogenous gene, miRNA, or mRNA can be through modulation of the processing of a mRNA, such processing including transcription, transportation and/or translation within a cell. Modulation may also be effected by the inhibition or enhancement of miRNA activity with a cell, tissue, or organ. Such processing may affect the expression of an encoded product or the stability of the mRNA. In still other embodiments, a nucleic acid sequence can comprise a modified nucleic acid sequence. In certain aspects, one or more miRNA sequence may include or comprise a modified nucleobase or nucleic acid sequence.

Identification of microRNA Inhibitors

Various assays can be used to identify inhibitors of specific miRs. Several plasmid and/or viral vectors expressing antagomirs, sponges, eraser and Tough Decoy (TuD) RNA molecules have been reported (Scherr, M. et al. Lentivirus-mediated antagomir expression for specific inhibition of miRNA function. *Nuc. Acid Res.* 35, e149 (2007); Sayed, D. et al. MicroRNA-21 targets Sprouty2 and promotes cellular outgrowths. *Mol. Biol. Cell* 19, 3272-3282 (2008); Ebert, M. S., Neilson, J. R. & Sharp, P. A. microRNAs ponges: competitive inhibitors of small RNAs in mammalian cells. *Nature Methods* 4, 721-726 (2007); Haraguchi, T., Ozaki, Y. & Iba, H. Vectors expressing efficient RNA decoys achieve the long-term suppression of specific microRNA activity in mammalian cells. *Nuc. Acid Res.* 37, e43(2009)). Other examples, also include, pulldown-seq, involving streptavidin pull-down and sequencing of RNAs bound to a transfected biotinylated miRNA mimic, IMPACT-seq (Identification of MREs by Pull-down and Alignment of Captive Transcripts—sequencing) which combines Pulldown-seq with RNase digestion.

In certain embodiments, a method of identifying a candidate inhibitor of a specific miRNA comprises contacting a cell that expresses the miRNA of interest, with a candidate agent and determining whether the miRNA has been inhibited. Any type of assay to determine miRNA inhibition can be conducted, e.g. blots, sequencing, pull-down assays etc.

For instance, identification methods may include (a) contacting a cell with a candidate miRNA-modulating compound; (b) determining the amount of activity of the miRNA of interest (e.g. miR-21 and/or miR-224) in the cell; and (c) comparing the amount of activity determined for the miRNA of interest (e.g. miR-21 and/or miR-224) with a control amount of activity of the miRNA of interest (e.g. miR-21 and/or miR-224), wherein a decrease in the amount of activity of the miRNA of interest (e.g. miR-21 and/or miR-224) in the contacted cell compared to the control amount of activity of the miRNA of interest (e.g. miR-21 and/or miR-224), respectively identifies the candidate miRNA-modulating compound as an miRNA-inhibiting compound for example as a miR-21 inhibitor (where miR-21 had been inhibited) or miR-224 inhibitor (where miR-224 had been inhibited). In certain aspects, a candidate compound or agent being designated as a miRNA-inhibiting compound, particularly designated as a miR-21 inhibitor and/or miR-224 inhibitor will exhibit at least a 5, 10, 20, 30, 40, 50, 60, 70, 80, 90 or 100 percent greater inhibition of activity of an assessed miRNA (e.g. miR-21 or miR-224) relative to a control.

Candidate Agents: Candidate compounds can be isolated, from microorganisms, animals or plants, for example, and can be produced recombinantly, or synthesized by chemical methods known in the art. The methods can be practiced with any test compounds as candidate agents. Test compounds useful in practicing the inventive method may be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection.

Examples of methods for the synthesis of molecular libraries may be found in the art, for example, in: DeWitt et al., 1993, Proc. Natl. Acad. Sci. USA 90:6909-6913; Erb et al., 1994, Proc. Natl. Acad. Sci. USA 91:11422-11426; Zuckermann et al., 1994, J. Med. Chem. 37:2678-2685; Cho et al., 1992, Science 261:1303-1305; Carell et al., 1994, Angew. Chem. Int. Ed. Engl. 33:2059-2061; Carell et al., 1994, Angew. Chem. Int. Ed. Engl. 33:2061-2064; and Gallop et al., 1994, J. Med. Chem. 37:1233-1251.

Libraries of compounds may be presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869), or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J Mol. Biol. 222:301-310).

Commercially available libraries that may be screened include, but are not limited to, the TimTec Natural Product Library (NPL), NPL-640, and TimTec NDL-3000 library. Libraries comprising compounds modeled on polyamines (i.e., polyamine analogs) may also be screened.

In certain embodiments, the candidate agent is a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule is meant a ligand ranging in size from about 10,000 daltons or greater in molecular weight.

The method may be practiced iteratively using different concentrations of a test candidate and/or different testing conditions, such as duration of reaction time. Test candidates that are identified by the method can be further tested by conventional methods in the art to verify specificity, dose dependency, efficacy in vivo, and the like. Test candidates may serve as lead compounds for developing additional test candidates.

The present disclosure finds use in monitoring miRNA inhibition in an assay wherein the test is conducted using cells. In these embodiments, the cells are cultured under specific user-defined conditions (e.g., in the presence or absence of a cytokine, nutrient and/or candidate therapeutic agent), and monitored for emitted light.

A prototype compound or agent may be believed to have therapeutic activity on the basis of any information available to the artisan. For example, a prototype agent may be believed to have therapeutic activity on the basis of information contained in the Physician's Desk Reference. In addition, by way of non-limiting example, a compound may be believed to have therapeutic activity on the basis of experience of a clinician, structure of the compound, structural activity relationship data, $EC_{50}$, assay data, $IC_{50}$ assay data, animal or clinical studies, or any other basis, or combination of such bases.

A therapeutically-active miRNA inhibitor or agent is an agent that has therapeutic activity, including for example, the ability of the agent to induce a specified response when administered to a subject or tested in vitro. Therapeutic activity includes treatment of a disease or condition, including both prophylactic and ameliorative treatment. Treatment of a disease or condition can include improvement of a disease or condition by any amount, including prevention, amelioration, and elimination of the disease or condition. Therapeutic activity may be conducted against any disease or condition, including in a preferred embodiment against any disease or disorder associated with damage by reactive oxygen intermediates. In order to determine therapeutic activity any method by which therapeutic activity of a compound may be evaluated can be used. For example, both in vivo and in vitro methods can be used, including for example, clinical evaluation, $EC_{50}$, and $IC_{50}$ assays, and dose response curves.

Candidate compounds for use with an assay of the present invention or identified by assays of the present invention as useful pharmacological agents can be pharmacological agents already known in the art or variations thereof or can be compounds previously unknown to have any pharmacological activity. The candidate compounds can be naturally occurring or designed in the laboratory. Candidate compounds can comprise a single diastereomer, more than one diastereomer, or a single enantiomer, or more than one enantiomer.

In an embodiment, the present disclosure provides a method of identifying a candidate compound as a suitable prodrug. A suitable prodrug includes any prodrug that may be identified by the methods of the present invention. Any method apparent to the artisan may be used to identify a candidate compound as a suitable prodrug.

In another aspect, the present disclosure provides methods of screening candidate compounds for suitability as therapeutic agents. Screening for suitability of therapeutic agents may include assessment of one, some or many criteria relating to the compound that may affect the ability of the compound as a therapeutic agent. Factors such as, for example, efficacy, safety, efficiency, retention, localization, tissue selectivity, degradation, or intracellular persistence may be considered. In an embodiment, a method of screening candidate compounds for suitability as therapeutic agents is provided, where the method comprises providing a candidate compound identified as a suitable prodrug, determining the therapeutic activity of the candidate compound, and determining the intracellular persistence of the candidate compound. Intracellular persistence can be measured by any technique apparent to the skilled artisan, such as for example by radioactive tracer, heavy isotope labeling, or LCMS.

In screening compounds for suitability as therapeutic agents, intracellular persistence of the candidate compound is evaluated. In a preferred embodiment, the agents are evaluated for their ability to modulate the translation of compositions embodied herein, over a period of time in response to a candidate therapeutic agent.

In another embodiment, soluble and/or membrane-bound forms of compositions, e.g. proteins, mutants or biologically active portions thereof, can be used in the assays for screening candidate agents. Cell-free assays can also be used and involve preparing a reaction mixture which includes miRNA molecules comprising a bioluminescent moiety and the test compound under conditions and time periods to allow the measurement of the translational and/or transcriptional activity over time, and concentrations of test agents.

In other embodiments, a candidate agent is an antisense oligonucleotide. In embodiments, the specific miRNA in a sample (e.g., cells or tissues in vivo or in vitro) treated using an antisense oligonucleotide of the invention is evaluated by comparison with miRNA in a control sample. For example, the miRNA is monitored by the signal emitted by the detectable moiety and compared with that in a mock-treated or untreated sample. Alternatively, comparison with a sample treated with a control antisense oligonucleotide (e.g., one having an altered or different sequence) can be made depending on the information desired. In another embodiment, a difference in the activity in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In some embodiments, the level of the desired miRNA molecule to be inhibited in a sample treated with an antisense oligonucleotide, is increased or decreased by about 1.25-fold to about 100-fold or more relative to an untreated sample or a sample treated with a control nucleic acid.

Preferably, the level or amount of the miRNA is decreased. In embodiments, the level of miRNA is i decreased by at least about 1.25-fold, at least about 2-fold, at least about 5-fold, at least about 10-fold, at least about 20-fold, at least about 30-fold, at least about 40-fold, at least about 50-fold, at least about 60-fold, at least about 70-fold, at least about 75-fold, at least about 80-fold, at least about 85-fold, at least about 90-fold, at least about 91-fold, at least about 92-fold, at least about 93-fold, at least about 94-fold, at least about 95-fold, at least about 96-fold, at least about 97-fold, at least about 98-fold, at least about 99-fold, or at least about 99.9-fold or more. In embodiments, it is preferable that the level or amount of the miRNA is decreased.

Microarrays: Identification of a nucleic acid sequence capable of binding to a target molecule can be achieved by immobilizing a library of nucleic acids onto the substrate surface so that each unique nucleic acid is located at a defined position to form an array. In general, the immobilized library of nucleic acids are exposed to a biomolecule or candidate agent under conditions which favored binding of the biomolecule to the nucleic acids. The nucleic acid array would then be analyzed by the methods embodied herein to determine which nucleic acid sequences bound to the biomolecule. Preferably the biomolecules would carry a pre-determined label for use in detection of the location of the bound nucleic acids.

In further embodiments, oligonucleotides or longer fragments derived from any of the miRNA polynucleotide sequences, may be used as targets in a microarray. The microarray can be used to monitor the identity and/or expression level of large numbers of miRNAs simultaneously to identify candidate oligonucleotides which interact with specific miRNAs.

Microarrays may be prepared, used, and analyzed using methods known in the art (see, e.g., Brennan et al., 1995, U.S. Pat. No. 5,474,796; Schena et al., 1996, Proc. Natl. Acad. Sci. U.S.A. 93: 10614-10619; Heller et al., 1997, Proc. Natl. Acad. Sci. U.S.A. 94: 2150-2155; and Heller et al., 1997, U.S. Pat. No. 5,605,662). In other embodiments, a microarray comprises miRNAs or other desired molecules which can be assayed to identify a candidate agent.

In another embodiment a method for screening candidate agents for the inhibition of a specific miRNA comprises contacting a sample with a candidate therapeutic agent and measuring the effects the agent has on a target.

Chemical Libraries: Developments in combinatorial chemistry allow the rapid and economical synthesis of hundreds to thousands of discrete compounds. These compounds are typically arrayed in moderate-sized libraries of small molecules designed for efficient screening. Combinatorial methods, can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, Chem Rev 96:555-600, 1996; Kenan et al., Exploring molecular diversity with combinatorial shape libraries, Trends Biochem Sci 19:57-64, 1994; Janda, Tagged versus untagged libraries: methods for the generation and screening of combinatorial chemical libraries, Proc Natl Acad Sci USA. 91:10779-85, 1994; Lebl et al., One-bead-one-structure combinatorial libraries, Biopolymers 37:177-98, 1995; Eichler et al., Peptide, peptidomimetic, and organic synthetic combinatorial libraries, Med Res Rev. 15:481-96, 1995; Chabala, Solid-phase combinatorial chemistry and novel tagging methods for identifying leads, Curr Opin Biotechnol. 6:632-9, 1995; Dolle, Discovery of enzyme inhibitors through combinatorial chemistry, Mol Divers. 2:223-36, 1997; Fauchere et al., Peptide and non-peptide lead discovery using robotically synthesized soluble libraries, Can J. Physiol Pharmacol. 75:683-9, 1997; Eichler et al., Generation and utilization of synthetic combinatorial libraries, Mol Med Today 1: 174-80, 1995; and Kay et al., Identification of enzyme inhibitors from phage-displayed combinatorial peptide libraries, Comb Chem High Throughput Screen 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., Proc. Nat. Acad. Sci. USA, 90:6909-6913 (1993)); vinylogous polypeptides (Hagihara, et al., J. Amer. Chem. Soc. 114:6568 (1992)); nonpeptidal peptidomimetics with .beta.-D-glucose scaffolding (Hirschmann, et al., J. Amer. Chem. Soc., 114:9217-9218 (1992)); analogous organic syntheses of small compound libraries (Chen, et al., J. Amer. Chem. Soc., 116:2661 (1994)); oligocarbamates (Cho, et al., Science, 261:1303 (1993)); and/or peptidyl phosphonates (Campbell, et al., J. Org. Chem. 59:658 (1994)); nucleic acid libraries (see, Ausubel, Berger and Sambrook, all supra); peptide nucleic acid libraries (see, e.g., U.S. Pat. No. 5,539, 083); antibody libraries (see, e.g., Vaughn, et al., Nature Biotechnology, 14(3):309-314 (1996) and PCT/US96/ 10287); carbohydrate libraries (see, e.g., Liang, et al., Science, 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

High throughput screening can be used to measure the effects of drugs on complex molecular events such as signal transduction pathways, as well as cell functions including, but not limited to, cell function, apoptosis, cell division, cell adhesion, locomotion, exocytosis, and cell-cell communication. Multicolor fluorescence permits multiple targets and cell processes to be assayed in a single screen. Cross-correlation of cellular responses will yield a wealth of information required for target validation and lead optimization.

In another aspect, the present disclosure provides a method for analyzing cells comprising providing an array of locations which contain multiple cells wherein the cells contain one or more fluorescent reporter molecules; scanning multiple cells in each of the locations containing cells to obtain fluorescent signals from the fluorescent reporter molecule in the cells; converting the fluorescent signals into digital data; and utilizing the digital data to determine the distribution, environment or activity of the fluorescent reporter molecule within the cells.

A major component of the new drug discovery paradigm is a continually growing family of fluorescent and luminescent reagents that are used to measure the temporal and spatial distribution, content, and activity of intracellular ions, metabolites, macromolecules, and organelles. Classes of these reagents include labeling reagents that measure the distribution and amount of molecules in living and fixed cells, environmental indicators to report signal transduction events in time and space, and fluorescent protein biosensors to measure target molecular activities within living cells. A multiparameter approach that combines several reagents in a single cell is a powerful new tool for drug discovery.

This method relies on the high affinity of fluorescent or luminescent molecules for specific cellular components. The affinity for specific components is governed by physical forces such as ionic interactions, covalent bonding (which includes chimeric fusion with protein-based chromophores, fluorophores, and lumiphores), as well as hydrophobic interactions, electrical potential, and, in some cases, simple entrapment within a cellular component. The luminescent probes can be small molecules, labeled macromolecules, or genetically engineered proteins, including, but not limited to green fluorescent protein chimeras.

Those skilled in this art will recognize a wide variety of fluorescent reporter molecules that can be used in the present invention, including, but not limited to, fluorescently labeled biomolecules such as proteins, phospholipids, RNA and DNA hybridizing probes. Similarly, fluorescent reagents specifically synthesized with particular chemical properties of binding or association have been used as fluorescent reporter molecules (Barak et al., (1997), *J. Biol. Chem.* 272:27497-27500; Southwick et al., (1990), *Cytometry* 11:418-430; Tsien (1989) in *Methods in Cell Biology*, Vol. 29 Taylor and Wang (eds.), pp. 127-156). Fluorescently labeled antibodies are particularly useful reporter molecules due to their high degree of specificity for attaching to a single molecular target in a mixture of molecules as complex as a cell or tissue.

The luminescent probes can be synthesized within the living cell or can be transported into the cell via several non-mechanical modes including diffusion, facilitated or active transport, signal-sequence-mediated transport, and endocytotic or pinocytotic uptake. Mechanical bulk loading methods, which are well known in the art, can also be used to load luminescent probes into living cells (Barber et al. (1996), *Neuroscience Letters* 207:17-20; Bright et al. (1996), *Cytometry* 24:226-233; McNeil (1989) in *Methods in Cell Biology*, Vol. 29, Taylor and Wang (eds.), pp. 153-173). These methods include electroporation and other mechanical methods such as scrape-loading, bead-loading, impact-loading, syringe-loading, hypertonic and hypotonic loading. Additionally, cells can be genetically engineered to express reporter molecules, such as GFP, coupled to a protein of interest as previously described (Chalfie and Prasher U.S. Pat. No. 5,491,084; Cubitt et al. (1995), *Trends in Biochemical Science* 20:448-455).

Once in the cell, the luminescent probes accumulate at their target domain as a result of specific and high affinity interactions with the target domain or other modes of molecular targeting such as signal-sequence-mediated transport. Fluorescently labeled reporter molecules are useful for determining the location, amount and chemical environment of the reporter. For example, whether the reporter is in a lipophilic membrane environment or in a more aqueous environment can be determined (Giuliano et al. (1995), *Ann. Rev. of Biophysics and Biomolecular Structure* 24:405-434; Giuliano and Taylor (1995), *Methods in Neuroscience* 27.1-16). The pH environment of the reporter can be determined (Bright et al. (1989), *J. Cell Biology* 104:1019-1033; Giuliano et al. (1987), *Anal. Biochem.* 167:362-371; Thomas et al. (1979), *Biochemistry* 18:2210-2218). It can be determined whether a reporter having a chelating group is bound to an ion, such as $Ca^{++}$, or not (Bright et al. (1989), In *Methods in Cell Biology*, Vol. 30, Taylor and Wang (eds.), pp. 157-192; Shimoura et al. (1988), *J of Biochemistry* (Tokyo) 251:405-410; Tsien (1989) In *Methods in Cell Biology*, Vol. 30, Taylor and Wang (eds.), pp. 127-156).

Furthermore, certain cell types within an organism may contain components that can be specifically labeled that may not occur in other cell types. For example, neural cells often contain polarized membrane components. That is, these cells asymmetrically distribute macromolecules along their plasma membrane. Connective or supporting tissue cells often contain granules in which are trapped molecules specific to that cell type (e.g., heparin, histamine, serotonin, etc.). Most muscular tissue cells contain a sarcoplasmic reticulum, a specialized organelle whose function is to regulate the concentration of calcium ions within the cell cytoplasm. Many nervous tissue cells contain secretory granules and vesicles in which are trapped neurohormones or neurotransmitters. Therefore, fluorescent molecules can be designed to label not only specific components within specific cells, but also specific cells within a population of mixed cell types.

Those skilled in the art will recognize a wide variety of ways to measure fluorescence. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements (Giuliano et al. (1995), *Ann. Rev. of Biophysics and Biomol. Structure* 24:405-434; Giuliano et al. (1995), *Methods in Neuroscience* 27:1-16).

The whole procedure can be fully automated. For example, sampling of sample materials may be accomplished with a plurality of steps, which include withdrawing a sample from a sample container and delivering at least a portion of the withdrawn sample to test cell culture (e.g., a cell culture wherein gene expression is regulated). Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system, in a fully automated manner—for example, with an auto-sampler.

Labels: The particular label or detectable moiety or tag used in the assay is not a critical aspect of the invention, as long as it does not significantly interfere with the specific binding of the ORF phage to their ligands. The detectable group can be any material having a detectable physical or chemical property. Such detectable labels have been well developed in the field of immunoassays and, in general, most labels useful in such methods can be applied to the present invention. Thus, a label is any composition detectable by spectroscopic, photochemical, biochemical, immunochemical, electrical, optical, or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Delivery Vehicles

If desired, the nucleic acid sequences, e.g. miRNAs or inhibitors thereof, may also be used with a microdelivery vehicle such as cationic liposomes, lentiviral and adenoviral vectors. For a review of the procedures for liposome preparation, targeting and delivery of contents, see Mannino and Gould-Fogerite, *BioTechniques,* 6:682 (1988). See also, Felgner and Holm, *Bethesda Res. Lab. Focus,* 11(2):21 (1989) and Maurer, R. A., *Bethesda Res. Lab. Focus,* 11(2): 25 (1989).

The nucleic acid sequences of the disclsoure can be delivered to an appropriate cell of a subject. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 m in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 m and preferably larger than 20 m). Another way to achieve uptake of the nucleic acid is using liposomes, prepared by standard methods. The nucleic acids can be incorporated alone into these delivery vehicles or co-incorporated with tissue-specific antibodies, for example antibodies that target specific cell types. Alternatively, one can prepare a molecular complex composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression. In the relevant polynucleotides (e.g., expression vectors) the nucleic acid sequence encoding the an isolated nucleic acid sequence comprising, for example, a sequence encoding an miRNA inhibitor is operatively linked to a promoter or enhancer-promoter combination.

In some embodiments, the compositions embodied herein, can be formulated as a nanoparticle, for example, nanoparticles comprised of a core of high molecular weight linear polyethylenimine (LPEI) complexed with DNA and surrounded by a shell of polyethyleneglycol-modified (PEGylated) low molecular weight LPEI.

The nucleic acids and vectors may also be applied to a surface of a device (e.g., a catheter) or contained within a pump, patch, or other drug delivery device. The nucleic acids and vectors of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E. W. Martin), a well-known reference text in this field, and in the USP/NF (United States Pharmacopeia and the National Formulary).

Treatments may include various "unit doses." A unit dose is defined as containing a predetermined quantity of a therapeutic composition(s). The quantity to be administered, and the particular route and formulation, are within the skill of those in the clinical arts. A unit dose need not be administered as a single injection but may comprise continuous infusion over a set period of time. With respect to a viral component of the present invention, a unit dose may conveniently be described in terms of μg or mg of miRNA or miRNA mimetic. Alternatively, the amount specified may be the amount administered as the average daily, average weekly, or average monthly dose.

The oligonucleotides, e.g. miRNA inhibitors can be administered to the patient in a dose or doses of about or of at least about 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 μg or mg, or more, or any range derivable therein. Alternatively, the amount specified may be the amount administered as the average daily, average weekly, or average monthly dose, or it may be expressed in terms of mg/kg, where kg refers to the weight of the patient and the mg is specified above. In other embodiments, the amount specified is any number discussed above but expressed as mg/m$^2$ (with respect to tumor size or patient surface area).

Pharmaceutical Compositions

Pharmaceutical compositions according to the present disclosure can be prepared in a variety of ways known to one of ordinary skill in the art. For example, the nucleic acids and vectors described above can be formulated in compositions for application to cells in tissue culture or for administration to a patient or subject. These compositions can be prepared in a manner well known in the pharmaceutical art, and can be administered by a variety of routes, depending upon whether local or systemic treatment is desired and upon the area to be treated.

In certain embodiments, the compositions are administered systemically to the subject. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This disclosure also includes pharmaceutical compositions which contain, as the active ingredient, nucleic acids and vectors described herein, in combination with one or more pharmaceutically acceptable carriers. The terms "pharmaceutically acceptable" (or "pharmacologically acceptable") refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In some embodiments, the method for the delivery of a miRNA or an expression construct encoding such or combinations thereof is via systemic administration. However, the pharmaceutical compositions disclosed herein may also be administered parenterally, subcutaneously, directly, intratracheally, intravenously, intradermally, intramuscularly, or even intraperitoneally as described in U.S. Pat. Nos. 5,543,158; 5,641,515 and 5,399,363 (each specifically incorporated herein by reference in its entirety).

Injection of nucleic acids may be delivered by syringe or any other method used for injection of a solution, as long as the nucleic acid and any associated components can pass through the particular gauge of needle required for injection. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In certain formulations, a water-based formulation is employed while in others, it may be lipid-based. In particular embodiments of the invention, a composition comprising a tumor suppressor protein or a nucleic acid encoding the same is in a water-based formulation. In other embodiments, the formulation is lipid based.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral, intralesional, and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The practitioner responsible for administration will, in any event, determine the appropriate dose for the individual subject. Moreover, for human administration, preparations should meet sterility, pyrogenicity, general safety and purity standards as required by FDA Office of Biologics standards.

As used herein, a "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human.

The nucleic acid(s) are administered in a manner compatible with the dosage formulation, and in such amount as will be therapeutically effective. The quantity to be administered depends on the subject to be treated, including, e.g., the aggressiveness of the disease or cancer, the size of any tumor(s) or lesions, the previous or other courses of treatment. Precise amounts of active ingredient required to be administered depend on the judgment of the practitioner. Suitable regimes for initial administration and subsequent administration are also variable, but are typified by an initial administration followed by other administrations. Such administration may be systemic, as a single dose, continuous over a period of time spanning 10, 20, 30, 40, 50, 60 minutes, and/or 1, 2, 3, 4, 5, 6, 7, 8, 9, 10, 11, 12, 13, 14, 15, 16, 17, 18, 19, 20, 21, 22, 23, 24 or more hours, and/or 1, 2, 3, 4, 5, 6, 7, days or more. Moreover, administration may be through a time release or sustained release mechanism, implemented by formulation and/or mode of administration.

Combination Therapies

Furthermore, it is contemplated that the miRNA compositions may be provided as part of a therapy to a patient, in conjunction with traditional therapies or preventative agents. Moreover, it is contemplated that any method discussed in the context of therapy may be applied preventatively, particularly in a patient identified to be potentially in need of the therapy or at risk of the condition or disease for which a therapy is needed. In specific aspects, it is contemplated that a second therapy, such as chemotherapy, radiotherapy, immunotherapy, surgical therapy or other gene therapy, is employed in combination with the miRNA therapy, as described herein.

Accordingly, in certain embodiments, the methods embodied herein include one or more nucleic acids corresponding to, for example, an miRNA, miRNA mimic, an miRNA inhibitor and a therapeutic drug. Consequently, in some embodiments, there is a method of treating cancer, for example PDA, in a patient comprising administering to the patient the cancer therapeutic and an effective amount of at least one miRNA molecule.

Cancer therapies also include a variety of combination therapies with both chemical and radiation based treatments as well as immunotherapy protocols. Combination chemotherapies include but are not limited to, for example, 5-fluorouracil, alemtuzumab, amrubicin, bevacizumab, bleomycin, bortezomib, busulfan, camptothecin, capecitabine, carboplatin, cetuximab, chlorambucil, cisplatin (CDDP), COX-2 inhibitors (e.g., celecoxib), cyclophosphamide, cytarabine, dactinomycin, dasatinib, daunorubicin, examethasone, docetaxel, doxorubicin (adriamycin), EGFR inhibitors (gefitinib and cetuximab), erlotinib, estrogen receptor binding agents, etoposide (VP 16), everolimus, farnesyl-protein transferase inhibitors, gefitinib, gemcitabine, gemtuzumab, ibritumomab, ifosfamide, imatinibmesylate, larotaxel, lapatinib, lonafarnib, mechlorethamine, melphalan, methotrexate, mitomycin, navelbine, nitrosurea, nocodazole, oxaliplatin, paclitaxel, plicomycin, procarbazine, raloxifene, rituximab, sirolimus, sorafenib, sunitinib, tamoxifen, taxol, taxotere, temsirolimus, tipifarnib, tositumomab, transplatinum, trastuzumab, vinblastin, vincristin, or vinorelbine or any analog or derivative variant of the foregoing.

Immunotherapy protocols may include for example treatment with an agent such as one or more checkpoint inhibitors (e.g. pembrolizumab (Keytruda), nivolumab (Opdivo), cemiplimab (Libtayo), ipilimumab (Yervoy), atezolizumab (Tecentriq), avelumab (Bavencio), durvalumab (imfinizi)), one or more immunomodulators, cytokine-expressing cells, or CAR T-cell therapy, and the like.

EXAMPLES

Example 1: Inhibition of miR-21 Regulates Mutant KRAS Effector Pathways and Intercepts Pancreatic Ductal Adenocarcinoma Development To study miRNA regulation of early PanIN development and progression, transgenic Kras$^{G12D/+}$; Trp53$^{R172H/+}$; Pdx-1-Cre (KPC) mice were used that exhibit stepwise progression through multiple stages of PanINs (PanIN1-3) to invasive PDA[17]. KPC mice resemble human PDA by genetic instability and histology, including desmoplastic TME[17]. Endogenous inhibition of miR-21 in primary KPC tumor cells decreased pro-tumorigenic functionalities relative to baseline levels, while overexpression of miR-224 in normal pancreatic fibroblasts conferred activated phenotypes. Inhibition of miR-21 in tumor cells simultaneously downregulated multiple tumorigenic pathways downstream of activated mKRAS. In vivo studies demonstrated that miR-21 inhibition increased survival in mice with established PDA, while early administration of a miR-21 inhibitor intercepted tumorigenesis and delayed premalignant progression. Collectively the studies, herein, identify miR-21 as a novel target for interception of mKRAS-driven PDA development.

Materials and Methods

KPC Mice. All animal studies were approved by the Institutional Animal Care and Use Committee of Johns Hopkins University. Lox-STOP-Lox-Trp53$^{R172H/+}$; Lox-STOP-Lox-Kras$^{G12D/+}$; and Pdx-1-Cre strains on a mixed C57BL/6 background, were gifted from Dr. David Tuveson (Cold Spring Harbor Laboratory, Cold Spring, NY.). These mice were backcrossed to the C57BL/6 genetic background for 12 generations and interbred to obtain KPC mice. All WT C57BL/6 mice were purchased from The Jackson Laboratories. All animals were kept in pathogen-free conditions and treated in accordance with the Institutional Animal Care and Use Committee of the Johns Hopkins University and American Association of Laboratory Animal Care approved guidelines. Animals were fed Teklad Global 18% Protein Extruded Rodent Diet. The Allentown Individually Ventilated Caging System (IVC) is used to house animals with Tek-Fresh paper bedding that is also an acceptable enrichment modality. Interventions were performed during light cycle.

Laser Capture Microdissection (LCM). Pancreata were isolated from aged KPC (4-20 weeks) or WT C57BL/6 mice and fresh-frozen in Tissue-Tek OCT (Sakura Finetek USA) or formalin-fixed and paraffin-embedded (FFPE) by the Johns Hopkins University Oncology Tissue Services. Guide slides were sectioned and stained with H&E by the Johns Hopkins University Oncology Tissue Services. Guide slides containing various grades of PanINs were identified by a pathologist. 10, 10 um frozen sections adjacent to guide sections were mounted on membrane slides (Zeiss) and stained with Cresyl Violet (Ambion). FFPE sections were stained with the Arcturus Paradise Plus Reagent System Staining kit (Thermo Fisher Scientific). Normal, low grade PanIN1, high grade PanIN2/3, and PDA tissue were microdissected using LCM (Leica LMD7000).

miRNA Profiling Using miRNA Microarray. RNA was extracted from fresh-frozen LCM samples using the RNAqueous-Micro Total RNA Isolation Kit (Thermo Fisher Scientific), quantified with a NanoDrop 1000 Spectrophotometer (Thermo Fisher Scientific), and converted to cDNA using the TaqMan MicroRNA Reverse Transcription Kit (Thermo Fisher Scientific) with Megaplex RT Primers Rodent Pool A and B (Thermo Fisher Scientific). cDNA was preamplified 18 cycles using the TaqMan PreAmp Master Mix (Thermo Fisher Scientific) and Megaplex PreAmp Primers Rodent Pool A and B (Thermo Fisher Scientific). miRNA microarray was performed by the Johns Hopkins School of Medicine Genetic Resources Core Facility using the TaqMan OpenArray Rodent MicroRNA Panel (Thermo Fisher Scientific) and TaqMan OpenArray Real-Time PCR Master Mix (Thermo Fisher Scientific). All Ct values were normalized to endogenous levels of U6 snRNA. Fold changes were quantified utilizing the ΔΔCt method in which all PanIN groups were normalized to the normal group (normal ducts isolated from WT C57BL/6 mice). P-values for differential expression statistics were generated and adjusted for multiple hypothesis testing using ExpressionSuite (Thermo Fisher Scientific).

Quantitative RT-PCR (qPCR). To quantify expression of select miRNAs, RNA was extracted from fresh-frozen LCM samples, primary cell lines, or whole pancreata using the RNAqueous™-Micro Total RNA Isolation Kit (Thermo Fisher Scientific). RNA concentration was quantified with a NanoDrop 1000 Spectrophotometer (Thermo Fisher Scientific) and cDNA was generated using the TAQMAN™ MicroRNA Reverse Transcription Kit (Thermo Fisher Scientific) with Taqman miRNA RT Assays (Thermo Fisher Scientific). cDNA was preamplified 12 cycles using the TAQMAN™ PreAmp Master Mix (Thermo Fisher Scientific) and Taqman miRNA™ Assays (Thermo Fisher Scientific). qPCR was performed using the Taqman Universal Master Mix II (Thermo Fisher Scientific) on the StepOnePlus Real-Time PCR System (Life Technologies) and analyzed by ExpressionSuite Software (Thermo Fisher Scientific). All miRNA targets and primers used are listed in Table 2. All Ct values were normalized to endogenous levels of U6 snRNA.

To quantify expression of mRNA gene targets, RNA was extracted from primary cell lines using the RNAQUEOUS™-Micro Total RNA Isolation Kit (Thermo Fisher Scientific). RNA was extracted from FFPE LCM samples using the High Pure RNA Paraffin Kit (Roche) and RNA integrity was determined using the Agilent RNA 6000 Pico Kit (Agilent Technologies) with an Agilent 2100 Bioanalyzer (Agilent Technologies). RNA was converted to cDNA using the SuperScript III First-Strand Synthesis SuperMix (Thermo Fisher Scientific). qPCR was performed using the Tagman Fast Advanced Master Mix (Thermo Fisher Scientific) on the StepOnePlus Real-Time PCR System (Life Technologies) and analyzed by ExpressionSuite Software (Thermo Fisher Scientific). All mRNA gene targets and primers used are listed in Table 3. All Ct values were normalized to endogenous levels of 18S RNA. All fold changes for qPCR were quantified using the ΔΔCt method.

Primary Cell Lines and Cell Culture. Primary KPC tumor epithelial cell line, KPC CAF, and C57BL/6 pancreatic normal associated fibroblasts (PNAF) were gifted from Dr. Lei Zheng (Johns Hopkins University School of Medicine, Baltimore, Md.), established in accordance with the Johns Hopkins Medical Institution Institutional Review Board-approved protocols, and developed and authenticated by DNA and gene expression profiling as previously described[51,52]. KPC tumor cells were sequenced to ensure that they have the KRAS$^{G12D}$ mutation. Fluorescent activated cell sorting (FACS) was performed to further purify and enrich for each cell line. KPC tumor cells were surface stained and sorted using anti-CD326 (EpCAM)-FITC (eBioscience). KPC CAFs were stained with primary antibody anti-FAP (Abcam) and secondary antibody Brilliant Violet 421 Donkey anti-rabbit IgG (BioLegend). PNAFs were stained with anti-PDGFRα-APC (Biolegend). All cell lines were dissociated with Cell Dissociation Buffer, enzyme free (Thermo Fisher Scientific), washed with sterile sorting buffer (PBS with 2% FBS), stained with primary antibody for 1 hour at 4 degrees in the dark, stained with secondary antibody for 30 minutes at 4 degrees in the dark, and then sorted using FACSAria Fusion SORP cell sorter (Becton Dickinson) by the Sidney Kimmel Comprehensive Cancer Center (SKCCC) Flow Cytometry Core. KPC Tumor cells, KPC CAFs, and PNAFs were maintained in RPMI 1640 (Life Technologies) supplemented with 10% FBS (Gemini Bio-products), 1 mM sodium pyruvate (Sigma), 2 mM L-glutamine (Life Technologies), 1% nonessential amino acids (Life Technologies), penicillin (50 U/ml)/streptomycin (50 µg/ml) (Life Technologies), and 0.2 U/ml human insulin (NovoLog) in a humidified incubator (37 degrees, 5% $CO_2$). C57BL/6 Mouse Primary Pancreatic Epithelial Cells (WT epithelial cells) were purchased from CellBiologics. WT epithelial cells were maintained in Complete Epithelial Cell Medium with Kit (CellBiologics).

Western Analysis of Phenotypic Markers. Cells were lysed with RIPA buffer (Thermo Fisher Scientific) supplemented with Halt Protease and Phosphatase Inhibitor Cocktail (Thermo Fisher Scientific). Protein was quantified using the Pierce BCA Protein Assay Kit (Thermo Fisher Scientific) according to the manufacturer's instructions. For Western Blotting, SDS PAGE was performed using the BioRad gel electrophoresis system. Protein lysate samples were mixed with XT Reducing Agent (BioRad) and XT Sample Buffer (BioRad), run on 4-12% bis-tris Criterion XT gels (BioRad) at 150V, and transferred to nitrocellulose membrane (GE Healthcare). Membranes were blocked using Odyssey Blocking Buffer, TBS (LI-COR) for 1 hour at room temperature or overnight at 4 degrees with gentle shaking. Primary antibodies anti-Vimentin (Abcam), anti-E-cadherin (Abcam), anti-α-smooth muscle actin (α-SMA) (Abcam), and anti-FAP (Abcam) were stained with secondary antibody IRDye® 800CW Donkey anti-Rabbit IgG (H+L) (LI-COR). Endogenous control primary antibody anti-β-Actin (Abcam) was stained with secondary antibody IRDye® 680RD Donkey anti-Chicken IgG (H+L) (LI-COR). Membranes were stained with primary antibodies diluted in Odyssey Blocking Buffer+0.2% Tween20 for 2 hours at room temperature with gentle shaking, washed with TBST (TBS with 0.1% Tween20), stained with secondary antibodies diluted in Odyssey Blocking Buffer+0.2% Tween20 for 1 hour at room temperature with gentle shaking in the dark, washed with TBST, then visualized with an Odyssey Infrared Imaging System scanner (LI-COR). Signal intensities were measured using FIJI software (ImageJ)[53].

Proliferation, Invasion, and Migration Assays. Cell Counting Kit-8 (CCK8) (Dojindo Molecular Technologies) was used for proliferation assays for all cell lines. Cells were seeded on 96-well plates and after a 90-minute incubation with CCK8 solution in a humidified incubator (37 degrees, 5% $CO_2$) the absorbance was measured at 450 nm. The colorimetric detection of the formazan dye at 450 nm directly correlates with cell viability. This procedure was repeated every 24 hours starting on day 0 to day 4. Invasion and migration assays were performed using Cultrex 96 Well BME Cell Invasion Assay kit (Trevigen) according to the manufacturer's instructions. Transwells were coated overnight with 1× basal membrane extract (BME) for invasion assays, while no BME coating was performed for migration assays. For both assays, cells were serum-starved for 24 hours before plating. Invasion and/or migration was measured 48 hours after plating cells using CCK8. Scratch assay or wound healing assay to quantify migratory capacities was performed by seeding 24-well plates at high density to produce immediate confluency. Once confluent, wells were scratched with a p200 pipet tip to produce a clear vertical partition and images were taken at 20× magnification using an Eos Rebel T2i camera (Canon) attached to a phase-contrast microscope. After a 24-48 hour incubation (depending on cell line used) in a humidified incubator, another image was taken and migration was measured by quantifying the percent partition closure relative to the 0 hour time point. Area of partition at each time point was quantified using FIJI software (ImageJ).

miRNA Fluorescence In Situ Hybridization (miR-FISH). In situ detection of miR-21, miR-224 and U6 snRNA was performed using miRCURY LNA microRNA ISH Optimization Kit (Exiqon) as per the manufacturer's instruction with modifications for frozen tissue sections (FIG. 1A). H&E slides of aged KPC pancreata prepared by the Johns Hopkins University Oncology Tissue Services were examined by a pathologist and PanINs of various grades were identified. Subsequent 10 pin frozen sections from histologically analyzed pancreata were fixed in 10% neutral buffered formalin overnight at room temperature. All washes were done with DEPC-PBS. Proteinase K (20 µg/ml) digestion was carried out in an ACD HybEZ hybridization oven (Advanced Cell Diagnostics) at 38 degrees for 15 min. Washes with 3% hydrogen peroxide solution in DEPC-PBS were used to block endogenous peroxidases. All locked-nucleic acid (LNA) miRNA probes (Exiqon) are double digoxigenin (DIG) labeled on the 5' and 3' ends, except for LNA-U6 which is DIG labeled only on the 5' end. Hybridization with each LNA miRNA probe was performed at specific optimal temperatures. LNA-miR-21 (TCAA-CATCAGTCTGATAAGCTA, SEQ ID NO: 1, 40 nM) was hybridized at 54 degrees, LNA-miR-224 (AACGGAAC-CACTAGTGACTT, SEQ ID NO: 2, 40 nM) was hybridized at 52.5 degrees, LNA-miR-Scramble (GTGTAACACGTC-TATACGCCCA, SEQ ID NO: 3, 40 nM) was hybridized at 54 degrees, and LNA-U6 (CACGAATTTGCGTGT-CATCCTT, SEQ ID NO: 4, 1 nM) was hybridized at 54 degrees. All LNA probes were hybridized for 1 hour in a humidified hybridization oven. After decreasing concentrations of saline-sodium citrate washes at probe hybridization temperatures, tissue sections were blocked at room temperature in a humidified chamber using the In Situ Hybridization (ISH) Blocking Solution (Vector Laboratories). Sections were stained with HRP-labeled anti-DIG primary antibody (*Gallus* Immunotech) diluted in blocking solution for 60 min at room temperature in a humidified chamber. TSA Plus Fluorescein (Perkin Elmer) detection substrate was applied to sections in the dark in order to produce an amplified fluorescent signal. Sections were then stained with nuclear dye Hoechst (Thermo Fisher Scientific). Slides were mounted with Prolong Diamond Antifade Mountant (Thermo Fisher Scientific) and cured overnight in the dark with proper ventilation. Slides were imaged the next day on Eclipse E800 fluorescence microscope (Nikon) at 20× magnification using the DAPI filter to capture nuclear staining and the FITC filter to capture miRNA staining. In situ miRNA expression was quantified by FITC intensity/nuclei using FIJI software (ImageJ).

Lentiviral Stable Transduction of Primary Cell Lines with miRNA Mimics and Inhibitors. All miRNA lentiviral particles were purchased from GeneCopoeia. The GeneCopoeia third generation self-inactivating HIV-based lentiviral vector system meets Biosafety Level 2 (BSL-2) requirements based on the criteria outlined by the Centers for Disease Control. Transduction of primary cell lines was performed according to the manufacturer's protocol. Viral suspension containing 8 µg/ml of Polybrene (Sigma) and 10 µl of lentivirus was diluted in complete media appropriate for each cell line to be transduced. Plates containing cells and viral suspension were placed in 4 degrees for 1.5 hours prior to overnight incubation in a humidified incubator (37 degrees, 5% $CO_2$) to increase transduction efficiency. Successfully transduced cells were selected via antibiotic selection using either 4 µg/ml puromycin (Sigma) or 400 µg/ml hygromycin B (Thermo Fisher Scientific). Transduced cells after selection were viewed at 20× magnification under Eclipse TE200 inverted fluorescence microscope (Nikon) to assess transduction efficiency. Cells were FACS sorted by eGFP or mCherry expression using FACSAria Fusion SORP cell sorter (Becton Dickinson) by the SKCCC Flow Cytometry Core to further enrich for successfully transduced cells.

RNA-Sequencing (RNA-Seq). RNA-Seq was performed on RNA isolated from KPC tumor cells stably transduced with either scramble inhibitor or miR-21 inhibitor and KPC CAFs stably transduced with either scramble inhibitor or miR-224 inhibitor. Eight total RNA samples were submitted; 2 RNA samples were submitted per treatment group. Quality control, library preparation, sequencing, and analyses were performed by the SKCCC Experimental and Computational Genomics Core. After RNA quantity and quality was assessed using an Agilent 2100 Bioanalyzer (Agilent Technologies), RNA libraries were generated using Illumina's TruSeq Stranded Total RNA Sample Prep Kit. 100 base pair (bp) paired end sequencing was performed on the RNA libraries to a depth of approximately 50 million reads per sample on an Illumina HiSeq2500. The reads were aligned to the mouse (mm10) reference genome using RSEM[54] version 1.3.0. Differential gene expression was computed with EBSeq[55]. Raw expected counts were normalized with upper quantile normalization.

Two comparisons were performed: (1) scramble-inhibited KPC tumor cells vs. miR-21 inhibited KPC tumor cells and (2) scramble-inhibited KPC CAFs vs. miR-224 inhibited KPC CAFs. Fold changes in gene expression between groups are calculated using the $\log_2$ (normalized expected counts of scramble group/normalized expected counts of miRNA-inhibited group). All RNA-Seq data are available on NCBI's public Gene Expression Omnibus (GEO) database under the accession number GSE143326.

Pathway Analysis. Of the 24,054 genes analyzed with RNA-Seq, a list of treatment-regulated genes was produced including all genes that have a high probability of differential expression (0.999<), greater than 4-fold increase or decrease in expression compared to the scramble group, and counts greater than 10. Generally Applicable Gene-set Enrichment (GAGE) package was performed in R to assess which KEGG and GO pathways were differentially expressed with treatment that possessed a q-value of <0.1[56].

In vivo Experiments and Drug Dosing. For in vivo PDA studies, subcutaneous flank tumors in WT C57BL/6 mice were established using a 2 CAF:1 tumor cell ratio composed of varying combinations of miRNA-inhibited or normal KPC tumor cells or CAFs. Each mouse received a subcutaneous injection of $5 \times 10^4$ total cells in a 100 µl suspension of 50% PBS, 50% Matrigel Basement Membrane Matrix Growth Factor Reduced, Phenol Red Free (Corning) by volume. Tumors were palpable 6 days after implantation and measured by digital calipers every two days. Tumor volume was calculated using tumor dimensions (Length×Width$^2$)/2. Survival experiments continued until mice were euthanized according to protocol due to tumor ulceration or when tumors reached 2 cm in diameter.

To investigate systemic miRNA inhibition on premalignant progression, we dosed 4-5 weeks old KPC mice intravenously (I.V.) with 25 mg/kg of miR-21 inhibitor, miR-224 inhibitor, or negative control scramble inhibitor in 0.2 mL PBS once every 5 days for 6 weeks[57]. All systemically administered in vivo inhibitors are miRCURY LNA miRNA Power Inhibitors (Qiagen) synthesized with a locked-nucleic acid (LNA) ribose ring modification and a phosphorothioate-linked nucleotide backbone. When the treated and untreated KPC mice were 10-11 weeks old, mice were sacrificed and pancreata, livers, lungs, and kidneys were harvested.

Immunohistochemistry (IHC). FFPE blocks of resected subcutaneous tumors from in vivo PDA experiments were sectioned and immunostained with anti-Ki67 antibody (Abcam) according to standard IHC protocols by the Johns Hopkins University Oncology Tissue Services. Stained slides were scanned using the ScanScope AT Turbo (Aperio) at 20× magnification by the Johns Hopkins University Oncology Tissue Services. Quantification of percent Ki67 positive cells on each slide was performed using HALO (Indica Labs).

Histologic Analysis of PanIN Lesions. Upon conclusion of the early-stage in vivo experiments, the pancreata of KPC mice systemically dosed with miRNA inhibitors were formalin-fixed and paraffin-embedded, sectioned, and stained using routine H&E protocols by the Johns Hopkins University Oncology Tissue Services. To assess the effect of various miRNA inhibitors on premalignant progression, 2 slides from each pancreas spaced 400 µm apart were graded based on the highest PanIN stage (or PDA) present by a pathologist blinded to the treatment group.

Analysis of The Cancer Genome Atlas (TCGA). MiRNA expression data from TCGA was interrogated to evaluate for a cell type correlation with miR expression[58,59]. The xCell Cell Types Enrichment Analysis pre-calculated values for TCGA was used to obtain TCGA cellular composition[60]. MicroRNA expression data from TCGA was obtained from the National Cancer Institute Genome Data Commons[58]. R version 3.6.1 (2019 Jul. 5) was used to subset both data frames to isolate the PDA cohort. MicroRNA expression data was subject to variance stabilization transformation prior to statistical analysis. DESeq2 version 1.24.0 was used to correlate miRNA expression values with the fibroblast and epithelial cell content estimated from xCell. In addition to correlation analysis, a linear model generated a best fit line associated with each comparison using variance stabilized miRNA expression values from DESeq2.

Statistical Analysis. Statistical analysis was performed using GraphPad Prism v7.0b (GraphPad Software). The data are presented as the means±SEM. Comparisons between groups were made using two-tailed unpaired Student t tests and one-way or two-way ANOVA. Survival data were plotted using a Kaplan-Meier curve and differences in treatment groups were tested using the log-rank (Mantel-Cox) test. For all analyses, statistical significance is defined and shown as *, $P<0.05$; , $P<0.01$; *, $P<0.001$; ****, $P<0.0001$. Statistical analyses for RNA-seq and TCGA are performed using R as described above.

Results

Comprehensive Profiling Identifies miRNAs Expressed in Early and Late Stage PanINs in KPC Mice.

A comprehensive miRNA profiling study of multiple PanIN stages and PDA was conducted using KPC mice. Microdissections were performed on increasing grades of PanINs from sections of KPC pancreata followed by a miRNA microarray analysis utilizing the Taqman OpenArray platform to quantify the levels of 750 known murine miRNAs. miRNA candidates were selected using specific criteria. First, candidate miRNAs had cycle threshold (Ct) values <30 and within the detection limits of the assay. Second, candidate miRNAs had large fold changes in expression that were consistently increasing or decreasing with PanIN progression to PDA. Third, miRNAs with significant fold changes (adjusted P-value<0.05) in each PanIN stage relative to normal ducts of wildtype (WT) C56BL/6 mice, were chosen. Confirmatory qPCR was completed to validate all miRNAs identified by OpenArray. Lastly, the miRNAs had to have either putative or proven roles in cancer promoting pathways.

These selection criteria resulted in 14 miRNA candidates. Table 1 summarizes the fold changes observed with increasing stages of PanIN development to PDA of the top 14 candidates. Significant dysregulation of some miRNAs (miR-21, miR-16, and miR-28) was found as early as low-grade PanIN1 (P1), while dysregulation of others (miR-224, miR-28 and miR-216b) began at higher PanIN grades (P2/3). All 14 candidate miRNAs have significantly dysregulated expression in PDA compared to expression levels in normal ducts of WT mice.

Figure 8:
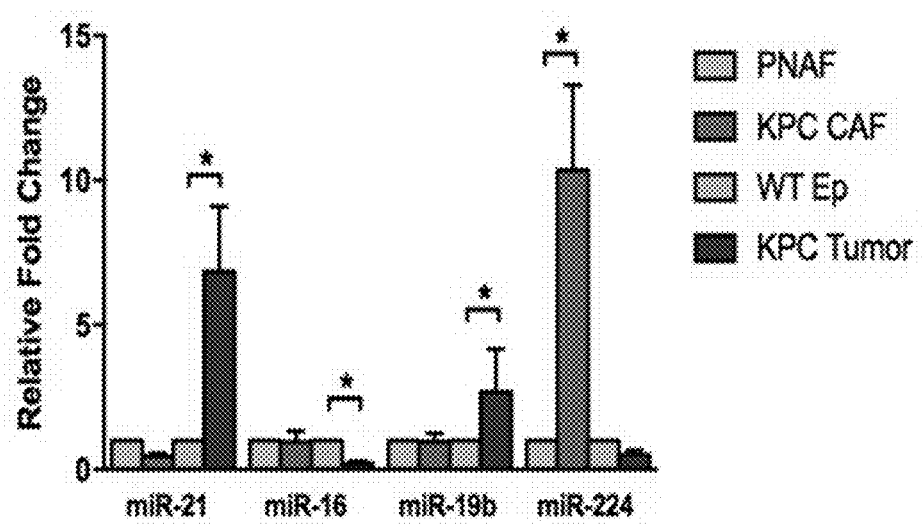
FIG. 8 is a graph showing the expression of the top 4 miRNAs in primary cell lines of the PDA TME. Relative fold changes of all 4 miRNAs were quantified using the ΔΔCt method in which all Ct values were first normalized to endogenous control U6 snRNA and KPC tumor and CAF groups were normalized to WT pancreatic epithelial cells (WT Ep) and PNAFs respectively (n=4 samples/group, significance was determined by an unpaired Student t test between groups). All data are mean values±SEM. Statistically significant P values are shown as * $P<0.05$

Increased Spatial-Temporal Expression of miR-21 and miR-224 with PanIN Progression to PDA Development miR-21 and miR-224 were chosen for further evaluation because these two miRNAs have regulate targets in cancer-promoting inflammatory pathways and epithelial-mesenchymal transition, respectively. miRNA fluorescence was performed in situ hybridization (miR-FISH) to examine the endogenous expression of miR-21 and miR-224 in specific cell populations in early and late PanINs and in PDA. miR-FISH allows the fluorescent visualization of miRNAs in sections of whole tissue. The intensity of the fluorescent signal directly correlates with levels of endogenous miRNA expression. Modified bicyclic locked-nucleic acid (LNA) probes were used, that are complimentary in sequence and therefore will stably and accurately hybridize to miRNAs of interest at specific hybridization temperatures in situ.

miR-FISH staining of WT ducts, increasing grades of KPC PanINs, and PDA tissue demonstrated that spatial-temporal expression of miR-21 is specifically concentrated in the ductal epithelial cells of PanIN lesions and increases in expression with progression to PDA (FIG. 1C). The quantified raw fluorescent intensities of miR-21 in PDA tissue is significantly increased compared to normal WT ducts, while the normalized fluorescent signal indicates that high grade PanIN2/3 lesions have a significant 3.5-fold increase and PDAs have a significant 6-fold increase of miR-21 expression compared to normal ducts (FIG. 1C), which correlates closely to the 7-fold increase of miR-21 expression in KPC tumor cells relative to WT pancreatic epithelial cells quantified by qPCR (FIG. 8). In contrast, miR-224 expression localized in the invading stromal compartment surrounding high grade PanIN2/3 lesions and persists with progression to PDA (FIG. 1D). These data are consistent with the findings in KPC CAFs that miR-224 expression is upregulated relative to normal pancreatic associated fibroblasts (PNAFs) early in the premalignant stromal cell compartment of developing PDAs. Moreover, the normalized fluorescent signal of miR-224 produced by miR-FISH (FIG. 1D) demonstrates that the significant 10-fold upregulation of miR-224 in PDA stroma equals the 10-fold increase of miR-224 expression in KPC CAFs as compared to PNAFs (FIG. 8). The miR-FISH results qualitatively and quantitatively confirm qPCR results and further informs the compartmental-specific expression of miR-21 and miR-224 throughout early PDA development.

miR-21 Inhibition Decreased Tumor Cell Proliferation, Migration, and Invasion, Whereas miR-224 Inhibition Increased CAF Cell Migration To investigate the functional roles of miR-21 and miR-224 in regulating early PDA development, the primary cell lines were stably transduced with miRNA inhibitors and mimics. Since KPC tumor cells express higher levels of miR-21 than WT epithelial cells and KPC CAFs express higher levels of miR-224 than PNAFs, lentiviral vectors were used to stably inhibit endogenous levels of miR-21 in KPC tumor cells and miR-224 in KPC CAFs. The inhibition occurs through expression of miRNA inhibitors that bind to target miRNAs via sequence complementation to prevent the loading of target miRNAs onto the RNA-induced silencing complex (RISC). Conversely, WT pancreatic epithelial cells and PNAFs were transduced with lentivirus overexpressing miR-21 and miR-224, respectively. Successfully transduced cells were selected using antibiotics specific to each construct, and further enriched using FACs sorting (FIGS. 9A-9F). FIG. 9G summarizes the lentiviral vectors, target cell lines, fluorescent markers, and antibiotic selection used to generate stable cell lines expressing their associated miRNA mimic or inhibitor.

Figure 2A:
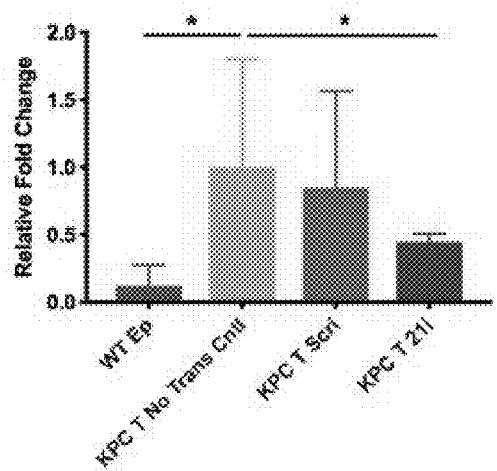
FIGS. 2A-2D are a series of graphs demonstrating that inhibition of miR-21 in KPC tumor cells decreases cell proliferation, migration, and invasion.

The degree of miRNA inhibition was measured by qPCR. miRNA inhibitors significantly reduced the expression of miR-21 in KPC tumor cells and miR-224 in KPC CAFs about 2-fold compared to non-transduced cells. However, inhibition was incomplete due to residual miR-21 and miR-224 expression being higher than in WT epithelial cells (FIG. 2A) and PNAFs (FIG. 3A), respectively.

Figure 2B:
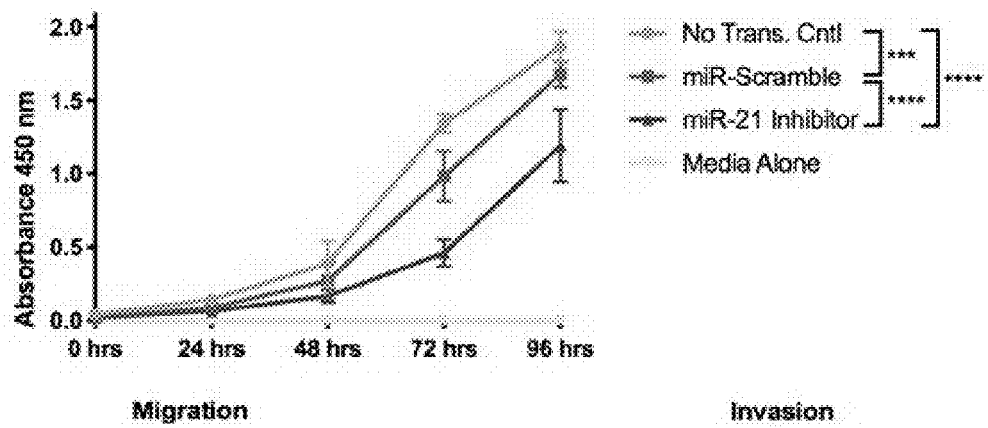
Figure 2C:
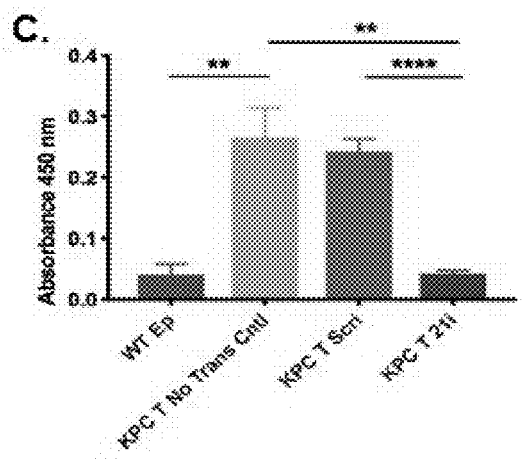
Figure 2D:
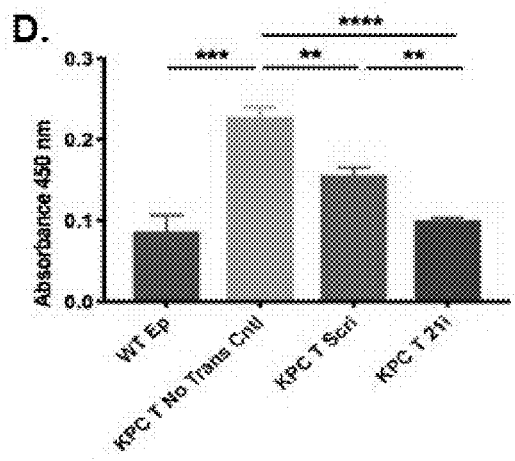

Next, functional changes in KPC tumor cells following reduced expression of miR-21 were investigated. miR-21 inhibition significantly reduced proliferation by 2-fold relative to non-transduced KPC tumor cells (FIG. 2B). More importantly, downregulation of miR-21 significantly reduced both migration and invasion to levels comparable to that of WT pancreatic epithelial cells (FIGS. 2C-D), demonstrating that reduction of miR-21 levels in KPC tumor cells can revert the cell's migratory and invasive capacities to that of normal un-transformed epithelial cells. Interestingly, downregulation of miR-224 in KPC CAFs did not affect cell proliferation (FIG. 3B) or invasion (FIG. 3D) as compared to non-transduced or scramble inhibitor-transduced CAFs. However, the migratory capacity of KPC CAFs was significantly increased by 1.7-fold in miR-224 inhibited CAFs compared to non-transduced CAFs (FIG. 3C).

Figures 3A, 3B, 3C, 3D, 3E, 3F, 3G:
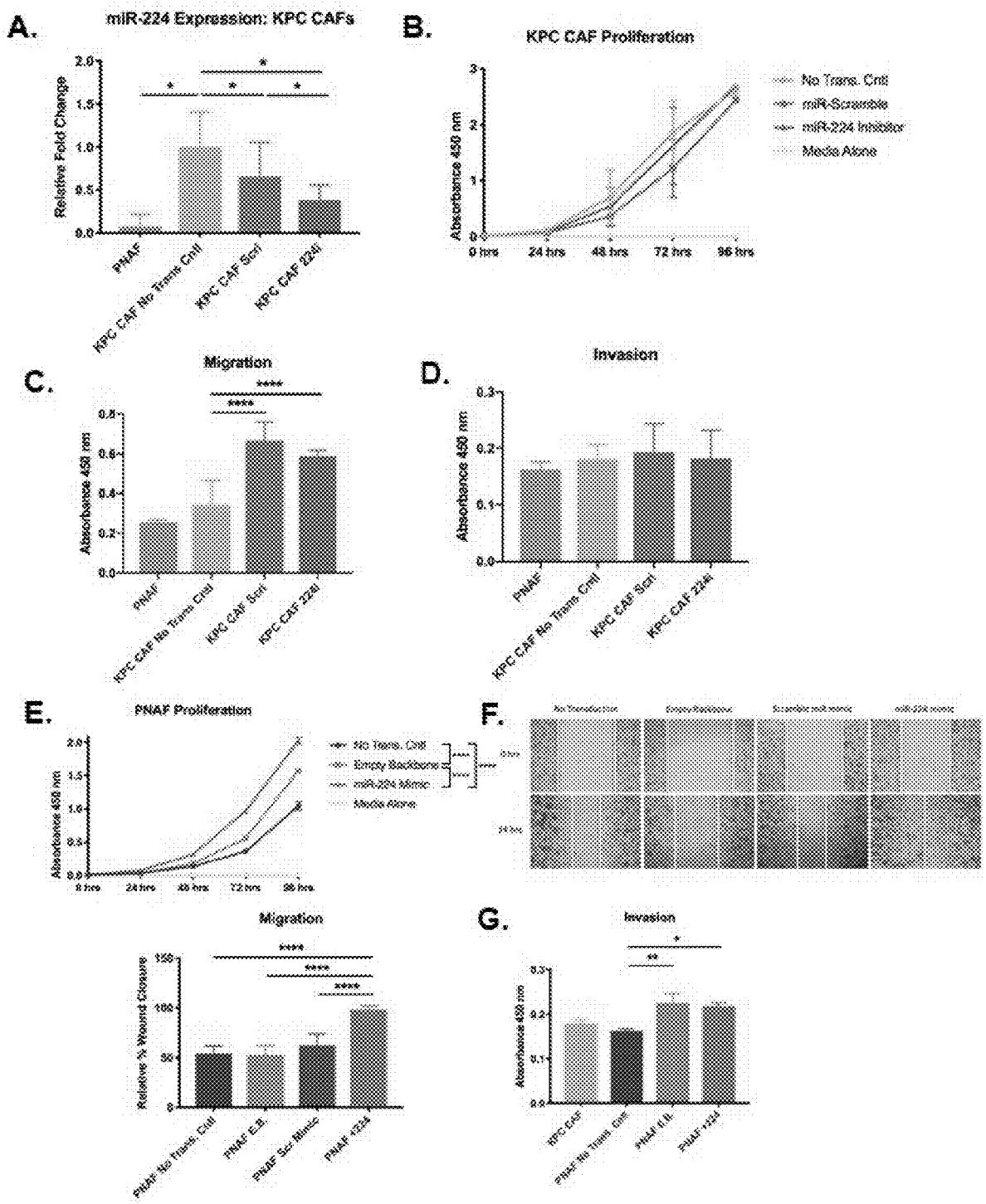
FIGS. 3A-3G are a series of graphs and images demonstrating that inhibition of miR-224 in KPC CAFs increases migration, and overexpression of miR-224 in normal fibroblasts increases cell proliferation, migration, and invasion.

PNAF miR-224 Overexpression Increased Cell Proliferation, Migration and Invasion PNAFs overexpressing miR-224 have a significant 2-fold increase in cell proliferation compared to non-transduced PNAFs (FIG. 3E). Scratch assay demonstrated upregulation of miR-224 expression significantly increased PNAF migratory capacity by 2-fold compared to all other control groups to achieve 100% wound closure (FIG. 3F). This migratory capacity is comparable to KPC CAFs (FIG. 7H), indicating that miR-224 overexpression can confer activated phenotypes like migration to PNAFs. Additionally, PNAFs overexpressing miR-224 have significantly increased cell invasion compared to non-transduced PNAFs (FIG. 3G). Collectively, this demonstrated that increased expression of miR-224 in normal fibroblasts produces CAF-liked activated cellular functions.

Stable Inhibition of miR-21 in KPC Tumor Cells Downregulates Pro-Tumorigenic Pathways Downstream of mKRAS Activation RNA-seq was employed to investigate global miRNA-mediated modulation of key genes and pathways regulated by miR-21 in tumor cells and miR-224 in CAFs. Log fold changes for all gene transcripts were compared between (1) miR-21-inhibited and scramble-inhibited KPC tumor cells and (2) miR-224-inhibited and scramble-inhibited KPC CAFs. GAGE[20] pathway analyses on the differentially expressed gene sets produced by miR-21 and miR-224 inhibition revealed miR-21 inhibition significantly downregulated the MAPK, mTOR and actin cytoskeleton KEGG pathways in tumor cells (FIG. 10A), while miR-224 inhibition significantly downregulated the DNA replication, cell cycle and p53 signaling KEGG pathways in CAFs (FIG. 10B).

Figures 10A, 10B:
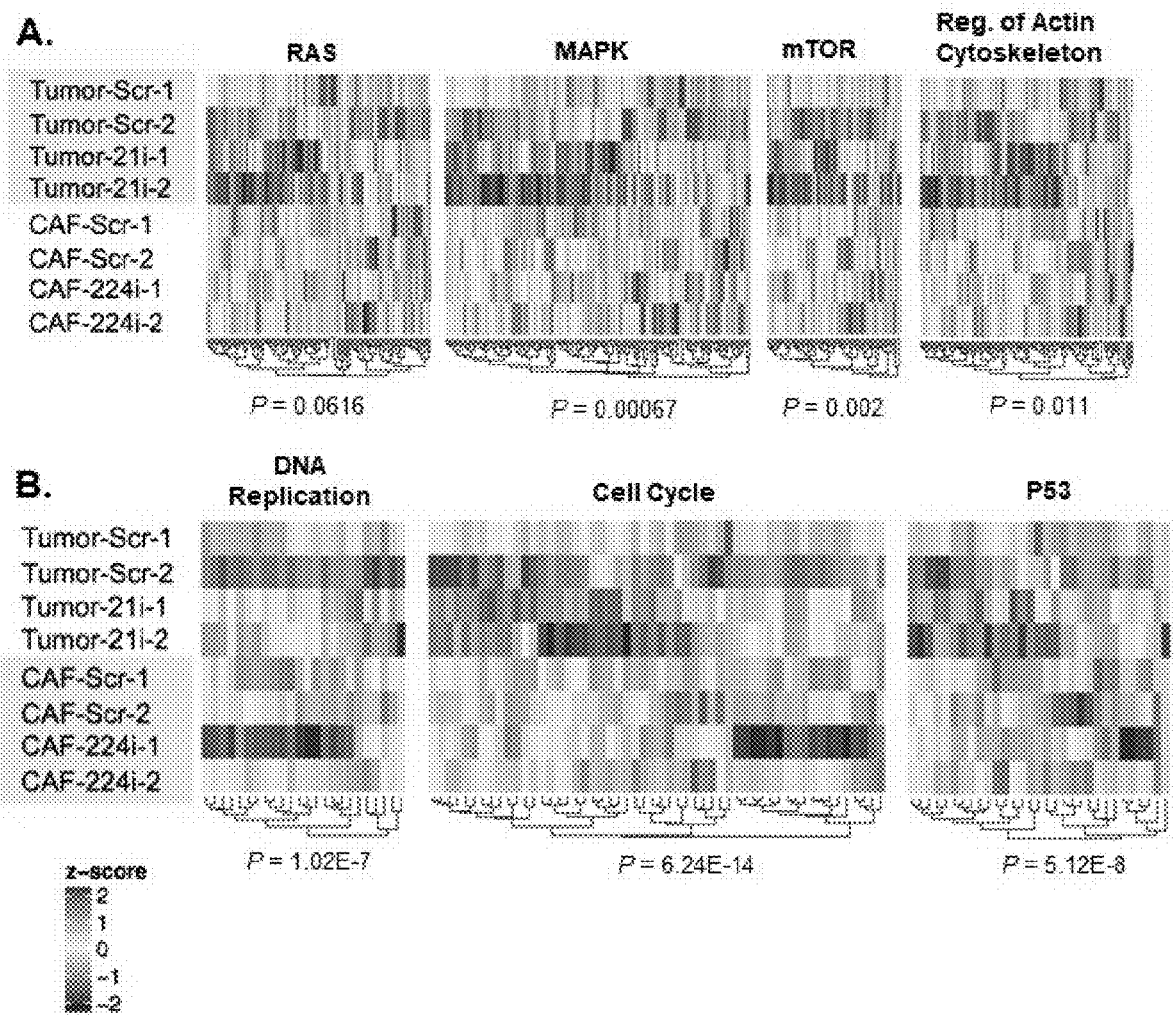
FIGS. 10A and 10B are heatmaps demonstrating miRNA modulation of the transcriptome.

The heatmaps for the three KEGG pathways significantly downregulated by miR-21 inhibition in KPC tumor cells (highlighted top 4 rows) are shown in FIG. 10A. Although not statistically significant (P=0.06), the RAS pathway was included for analysis due to the biological importance and relevance of the pathway to both early PanIN progression and PDA development. All 4 heatmaps display downregulation in all 4 pathways (in blue) for the two miR-21-inhibited tumor samples compared to the two scramble-inhibited tumor samples which have higher gene expression. In contrast, there is less consistent downregulation in the CAF samples (bottom 4 rows), indicating that the regulation of these 4 KEGG pathways are specific to miR-21's role in PDA cells. The significant downregulation of MAPK, mTOR and actin cytoskeleton pathways by miR-21 inhibition in tumor cells is in accordance with the reduced proliferation, migration and invasion observed with stable miR-21 inhibition. 5 differentially expressed genes were selected from each pathway for qPCR validation of fold changes (FIGS. 11B-11E).

Figures 4A, 4B, 4C:
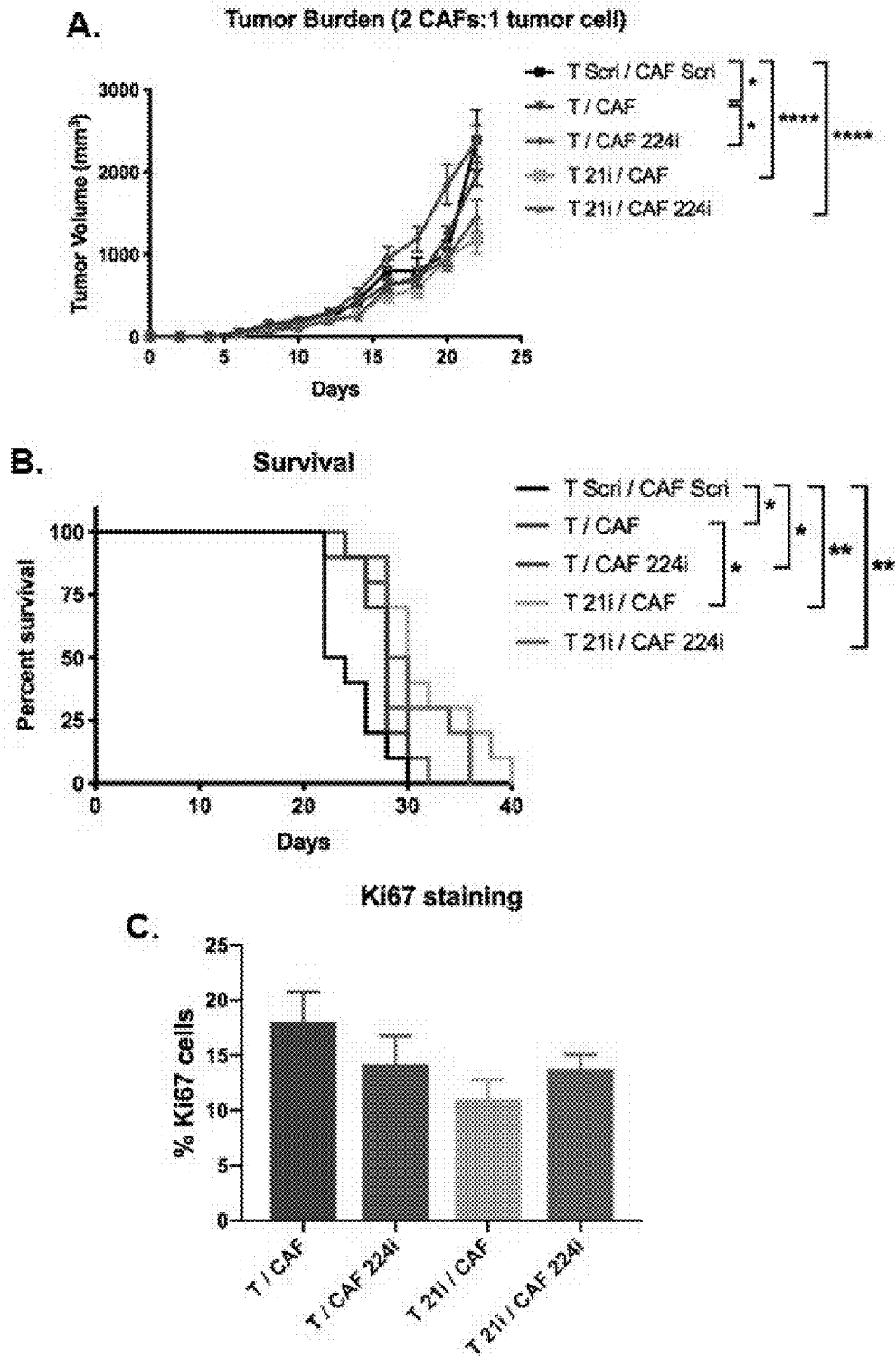
FIGS. 4A-4C are a series of graphs showing the effects of in vivo miR-21 and miR-224 inhibition on tumor burden and survival. Subcutaneous tumors composed of 2 CAF:1 tumor cell ratio of various combinations of scramble-inhibited, miRNA-inhibited, or normal KPC cells were implanted into the flanks of immunocompetent WT C57BL/6 mice.
Figure 11A:
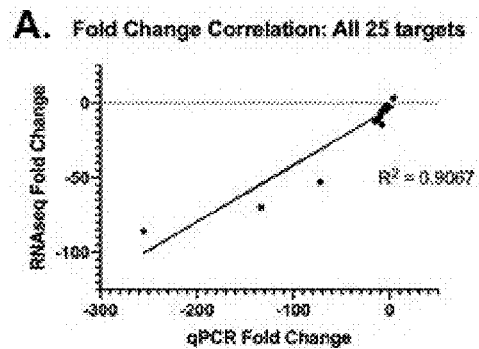
FIGS. 11A-11F are a series of plots demonstrating the qPCR validation of RNA-seq pathways. Confirmatory qPCR of pathway targets strongly correlate with RNAseq expressional changes. Fold changes generated by qPCR was plotted against fold changes generated by RNA-seq. Fold change correlation plots of FIG. 11A all 25 genes.
Figure 11B:
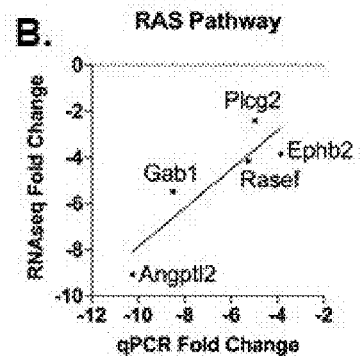
Figure 11C:
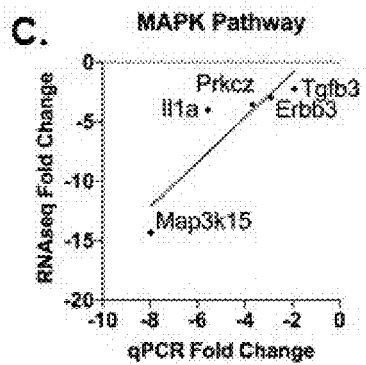
Figure 11D:
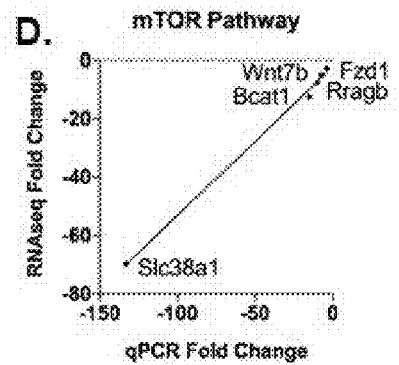
Figure 11E:
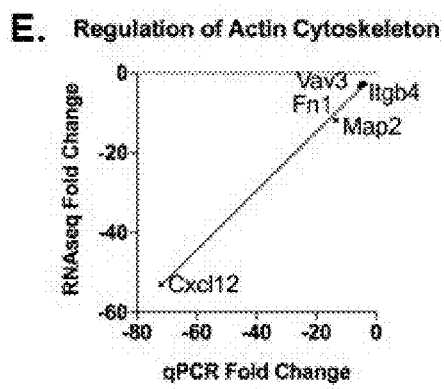
Figure 11F:
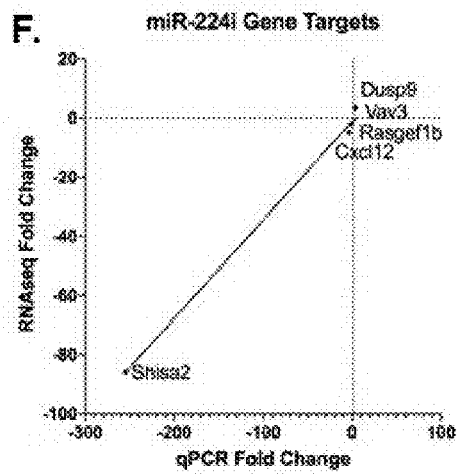

The heatmaps for the three KEGG pathways that were significantly downregulated by miR-224 inhibition in KPC CAFs (highlighted bottom 4 rows) are shown in FIG. 10B. Despite being statistically significant, the heatmaps of all three pathways lack consistent gene expression changes between samples within each treatment group. Additionally, there is minimal clustering within the two samples of scramble-inhibited KPC CAFs. The transcriptional variability between biological replicates may indicate that there is greater heterogeneity of expressed genetic pathways following miR-224 inhibition in CAFs than can be adequately measured by this approach. 5 genes (Shisa2, Cxcl12, Rasgef1b, Vav3, Dusp9) were chosen, regardless of pathway classification, that were significantly regulated by miR-224 inhibition for qPCR validation of fold changes (FIG. 11F). Of the genes screened, Shisa2 was most significantly downregulated by miR-224 inhibition in CAFs, with a 255-fold reduction by qPCR (greater than 86-fold reduction by RNA-seq) when compared to the expression in CAFs transduced with scramble inhibitor. Shisa2, a regulatory endoplasmic reticulum (ER) protein, inhibits fibroblast growth factor (FGF) signaling by preventing the maturation and cell-surface expression of FGF receptors (FGFRs)[21]. FGF signaling through FGFRs have been shown to promote cell migration in many cancer types and embryogenesis[22,23]. Therefore, the significant reduction in Shisa2 levels by miR-224 inhibition and potential increase in FGFR may explain the increased migration of miR-224-inhibited CAFs in vitro (FIG. 3C).

miR-21 Inhibition In Vivo Increases Overall Survival in Established PDA The effects of inhibiting miR-21 in vivo were investigated next. Between 60 and 90% of primary PDA tumor volume is fibrotic stroma[8,24]. Therefore, to more accurately recapitulate the major components of the PDA TME, w subcutaneous tumors were established in C57BL/6 mice with a 2 CAF:1 KPC tumor cell ratio of different combinations of miRNA-inhibited or normal KPC tumor cells or CAFs. Mice with tumors composed of miR-21-inhibited KPC tumor cells and normal KPC CAFs (T 21i/CAF) had the lowest tumor burden and longest survival compared to all other groups (FIGS. 4A, 4B). IHC staining of resected tumors with the proliferation marker Ki67, demonstrated that T 21i/CAF tumors had the lowest percentage of actively proliferating Ki67$^+$ cells (FIG. 4C), suggesting that reduced tumor size is due to decreased proliferative capacity of miR-21-inhibited tumor cells. Tumors composed of normal KPC tumor cells and miR-224-inhibited CAFs (T/CAF 224i) were comparable in size with scramble-inhibited tumors (T Scri/CAF Scri) and larger than normal non-transduced tumors (T/CAF). Collectively, these data show that only miR-21 inhibition of tumor cells reduces tumor burden and confers survival benefit in established PDA.

Figures 5A, 5B, 5C:
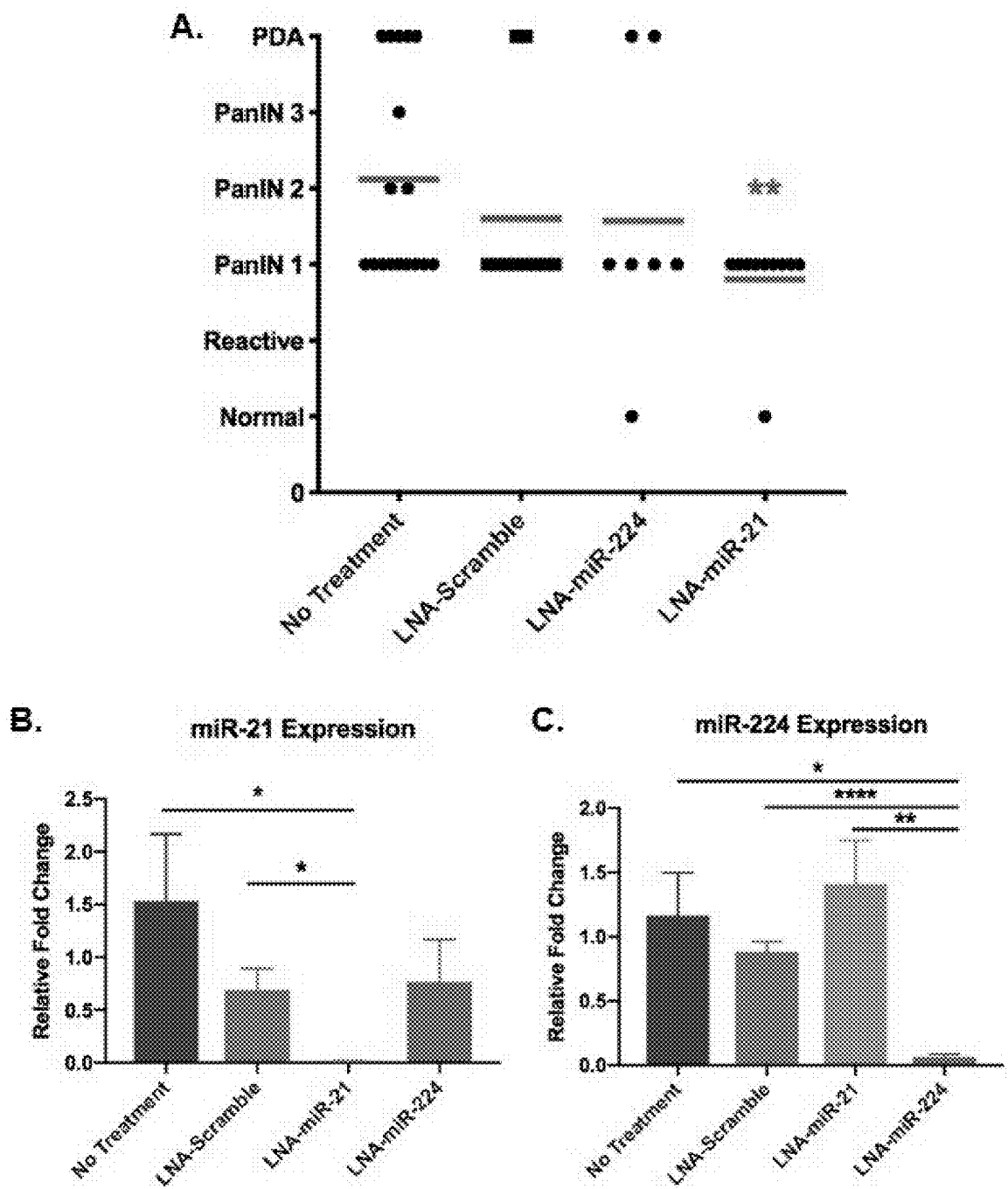
FIGS. 5A-5C are a series of graphs showing the effect of systemic miRNA inhibition on progression of PanIN lesions in KPC mice. KPC mice at 4-5 weeks of age were left untreated or I.V. dosed with 25 mg/kg of LNA-scramble inhibitor, LNA-miR-224 inhibitor, or LNA-miR-21 inhibitor every 5 days for 6 weeks. RNA was isolated from whole pancreata and qPCR quantified miR-21 and miR-224 levels in each treatment group.

Systemic Administration of LNA-miR-21 Inhibitor Intercepts Early PanIN Progression Systemic administration of miR-21 and miR-224 inhibitors delayed progression of PanIN lesions to PDA in KPC mice. To deliver miR-21 and miR-224 inhibitors, oligonucleotides were chemically modified with a LNA ribose ring structure and phosphorothioate backbone for enhanced pharmacokinetic stability in vivo[25]. 4-5 week old KPC mice, which are expected to already have low-grade PanIN1 lesions, were dosed with negative control LNA-scramble inhibitor, LNA-miR-21 inhibitor, or LNA-miR-224 inhibitor once every 5 days for 6 weeks. At the end of the dosing regimen, the pancreas, liver, lung and kidney from treated and untreated mice were collected and analyzed for drug efficacy and toxicity. Each pancreas was pathologically evaluated for the highest-grade lesion present. KPC mice receiving early systemic administration of LNA-miR-21 inhibitor developed the fewest advanced PanINs compared to other treatment groups (FIG. 5A). The average grade of premalignant lesions in the pancreas of mice dosed with LNA-miR-21 inhibitor was significantly lower than that of untreated mice. Furthermore, mice that received LNA-miR-21 inhibitor did not develop any lesions beyond the low-grade PanIN1 stage, demonstrating that early systemic miR-21 inhibition successfully delays premalignant progression. Additionally, our studies show that as a monotherapy, LNA-miR-21 inhibitor effectively intercepts PDA tumorigenesis when administered early at the time of mKRAS activation.

qPCR quantification of miRNA levels in the whole pancreas of dosed KPC mice showed that LNA-miR-21 inhibitor-treated mice had a significant 112-fold decrease and 50-fold decrease of miR-21 levels in their pancreas compared to untreated mice and LNA-scramble inhibitor-treated mice, respectively (FIG. 5B). Mice that received LNA-miR-224 inhibitor had a significant 19-fold decrease and 14-fold decrease of miR-224 levels in their pancreas as compared to untreated mice and LNA-scramble inhibitor-treated mice, respectively (FIG. 5C). Additionally, the data demonstrated that systemic miR-224 inhibition did not affect localized expression of miR-21 and vice versa, thereby demonstrating the specificity of each miRNA inhibitor. Collectively, these data show that systemically administered miRNA inhibitors successfully localized to the pancreas and inhibited their targets with a high degree of specificity.

Figures 6A, 6B:
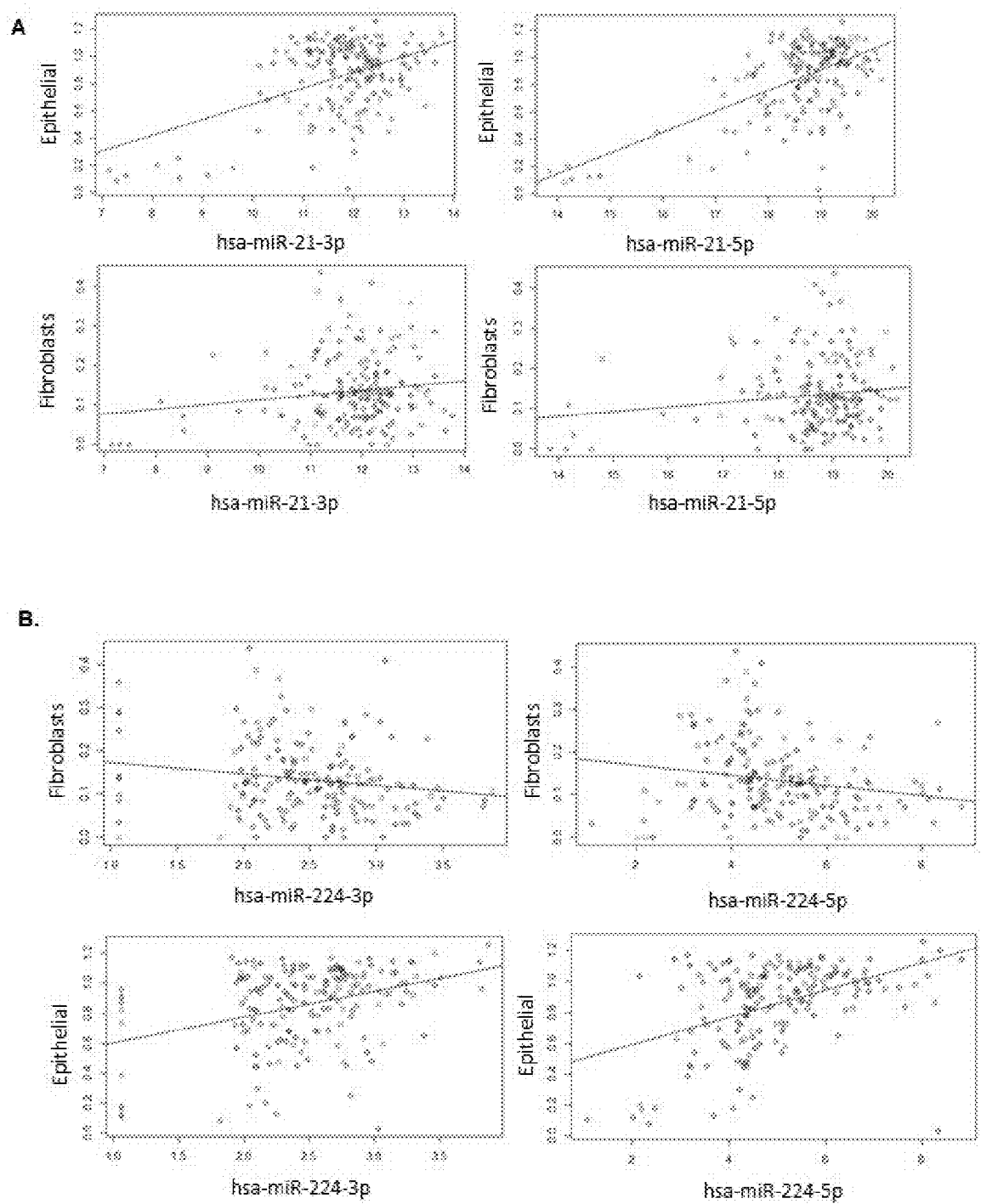
FIGS. 6A and 6B are a series of plots showing an analysis from TCGA which examines miR expression with tumor cellular content. The PDA cohort of TCGA was used to correlate miR expression in relation to tumor cellular composition estimated from computational microdissection with xCell.

Correlation of miR-21 and miR-224 Expression in TCGA Recapitulates Cellular Specificity in Human Tumors To examine translation of these findings to human PDA, miR-21 and miR-224 expression was investigated in the PDA cohort of TCGA. Specifically, a correlation was sought between miR-21 expression and epithelial cell content as well as miR-224 expression and fibroblast content. This corresponds to the murine findings providing evidence for miR-21 and miR-224 cellular and compartmental specificity. Using the publicly available xCell quantification for TCGA[26], epithelial and fibroblast content was compared to miR-21 and miR-224 expression in 177 patients in the PDA cohort. Correlation analysis revealed a significant direct relationship between miR-21 expression and tumor epithelial cell content with p-values of 8.7e-7 and 2.1e-13 for miR-21-3p and miR-21-5p, respectively (FIG. 6A). This relationship was not seen with comparison between miR-21 expression and tumor fibroblast content and is consistent with the findings in the KPC model.

Similar comparison for miR-224 expression revealed an inverse relationship between miR-224 expression and tumor fibroblast content and a direct relationship between miR-224 expression and tumor epithelial cell content (FIG. 6B). Though the miR-224 findings were not consistent with the in vitro and in vivo murine findings, the broad classification of fibroblasts in the dataset may not be limited to CAFs, which would impact this analysis.

TABLE 1

Fold changes of the top 14 dysregulated miRNAs over early PDA development.

| miRNA | Normal | P1 | P2/3 | PDA |
|---|---|---|---|---|
| Increasing Fold Change | | | | |
| hsa-miR-21 | 1 | 55* | 27 | 333* |
| hsa-miR-16 | 1 | 7* | 7 | 148* |
| hsa-miR-224 | 1 | 6 | 8* | 98* |
| hsa-miR-19b | 1 | 8 | 4 | 75* |
| hsa-miR-106b | 1 | 4 | 2 | 37* |
| hsa-miR-29a | 1 | 4 | 3 | 31* |
| hsa-miR-20a | 1 | 6 | 4 | 68* |
| hsa-miR-28 | 1 | 6* | 4* | 36* |
| hsa-miR-142-3p | 1 | 5 | 7 | 50 |
| hsa-miR-15b | 1 | 4 | 4 | 39* |
| mmu-miR-301b | 1 | 5 | 4 | 111* |
| hsa-miR-222 | 1 | 2 | 3 | 26* |
| hsa-miR-221 | 1 | 3 | 3 | 42* |
| Decreasing Fold Change | | | | |
| hsa-miR-216b | 1 | 1 | −29* | −100* |

Quantified fold changes of miRNA expression, either increasing or decreasing, over developmental groups low-grade PanIN1 (P1), high-grade PanIN2/3 (P2/3), and PDA. Fold changes were quantified via qPCR utilizing the ΔΔCt method in which all Ct values were first normalized to endogenous control U6 snRNA and all developmental groups were normalized to the normal group (normal ducts isolated from WT C57BL/6 mice) (n=4-5 samples per group). The hsa prefix denotes miRNAs found in both mice and humans due to sequence conservation.

TABLE 2

Taqman miRNA primers for qPCR (Thermo Fisher Scientific).

| Target miRNA | Primer ID |
|---|---|
| hsa-raiR-21 | 000397 |
| hsa-miR-16 | 000391 |
| hsa-rniR-224 | 000599 |
| hsa-miR-19b | 000396 |
| hsa-miR-106b | 000442 |
| hsa-miR-29a | 002112 |
| hsa-rniR-20a | 000580 |
| hsa-miR-28 | 000411 |
| hsa-miR-142-3b | 000464 |
| hsa-miR-15b | 000390 |
| mmu-miR-301b | 002600 |
| hsa-rniR-222 | 002276 |
| hsa-rniR-221 | 000524 |
| hsa-miR-2161, | 002326 |
| U6 rRNA | 001973 |

TABLE 3

Taqman mRNA primers for qPCR (Thermo Fisher Scientific).

| Target Gene | Primer ID |
|---|---|
| Rasef | Mm01257908_m1 |
| Angptl2 | Mm00507897_m1 |
| Ephb2 | Mm01181021_m1 |
| Gab1 | Mm00491216_m1 |
| Plcg2 | Mm01242530_m1 |
| Prkcz | Mm00776345_g1 |
| Tgfb3 | Mm00436960_m1 |
| Erbb3 | Mm01159999_m1 |
| Map3k15 | Mm01156835_m1 |
| IL1a | Mm00439620_m1 |
| Slc38a1 | Mm00506391_m1 |
| Rragb | Mm01348407_m1 |
| Wnt7b | Mm01301717_m1 |
| Fzd1 | Mm00445405_s1 |
| Bcat1 | Mm00500289_m1 |
| Map2 | Mm00485230_m1 |
| Cxcl12 | Mm00445553_m1 |
| Fn1 | Mm01256744_m1 |
| Itgb4 | Mm01266840_m1 |
| Vav3 | Mm01206062_m1 |
| Shisa2 | Mm00520925_m1 |
| Rasqef1b | Mm00521410_m1 |
| Dusp9 | Mm00512648_g1 |
| 18S | Mm04277571_s1 |

Discussion

MiRNAs are regulatory non-coding RNAs controlling signaling pathways in both normal and tumor cells. miR-21 and miR-224 were identified as regulators of specific cell types within developing mKRAS-driven PDAs. It was demonstrated that miR-21 is a potent regulator of epithelial to mesenchymal transition (EMT), modulating transformed epithelial cell invasion and migration. For the first time, it was shown that miR-21 can serve as a target for intercepting PDA development following mKRAS activation in early PanIN lesions. miR-224 was also identified as a key regulator of TME fibroblasts, activating normal fibroblasts to exhibit CAF activity. Finally, findings were extrapolated to the PDA cohort of TCGA and demonstrated a correlation between miR-21 expression and tumor epithelial cell content.

Since mKRAS targeting remains a challenge in the clinical setting, inhibiting downstream effector pathways is a leading strategy for developing mKRAS therapeutics. This study demonstrates miR-21 inhibition simultaneously downregulates pro-tumorigenic effector pathways including MAPK, mTOR and actin cytoskeleton pathways, downstream of mKRAS in KPC tumor cells. Previous studies demonstrated miR-21 directly inhibits individual tumor suppressor gene targets such as phosphatase and tensin homolog (PTEN)[27,28], programmed cell death protein 4 (PDCD4)[29], Sprouty2 (Spry2)[30], tropomyosin (TPM1)[31] and RAS p21 protein activator 1 (RASA1)[32,33] to modulate cell proliferation, migration, invasion, and apoptosis in various cancer types. However, it is shown herein that miR-21 inhibition is capable of simultaneously downregulating multiple mKRAS-activated biologic pathways responsible for tumor cell growth, metabolism, and EMT, indicating that miR-21 is a more potent regulator of mKRAS signaling than previously realized. Additionally, miR-21 has been identified as a downstream transcriptional target of KRAS activation via transcription factor ELK1, which directly binds to miR-21's proximal promoter region, leading to increased miR-21 expression[32]. Thus, miR-21 is a ncRNA effector of KRAS activation, providing additional rationale for its inhibition in mKRAS-driven PDA. Studies have shown that targeting individual downstream KRAS effectors such as MEK1/2, Erk1/2, or Akt has limited clinical efficacy due to compensatory mechanisms swiftly leading to acquired resistance, coupled with substantial toxicities[10,11]. It was also demonstrated herein, that miR-21 expression is directly related to tumor epithelial cell content for the PDA cohort of TCGA. miR-21 is a promising therapeutic target because its inhibition can block oncogenic KRAS signaling through the regulation of multiple signaling proteins in multiple key pro-tumorigenic pathways, thereby potentially reducing mechanisms of acquired resistance and toxicities associated with combination drug treatments.

The study herein, shows for the first time that miR-224 is specifically upregulated in activated KPC CAFs compared to normal fibroblasts, and its increased spatial-temporal expression in the developing TME is specifically localized in the stromal compartment surrounding high grade PanIN2/3 lesions and PDA. The in situ localization of miR-224 contrasts that of miR-21's, whose expression is concentrated in transformed ductal epithelial cells. Moreover, endogenous overexpression of miR-224 in normal pancreatic fibroblasts significantly increased cell proliferation, migration, and invasion, indicating that overexpression of miR-224 may generate CAFs by conferring activated phenotypes to normal fibroblasts.

It was postulated that the early upregulation of miR-224 may be due to the increased expression of hypoxia-inducible factor 1 alpha (HIF-1α) and NFκB in the developing TME[8,34]. Both HIF-1α in gastric cancer and NFκB in hepatocellular carcinoma (HCC) transcriptionally regulate miR-224 by binding directly to its promoter region[35,36]. Although only demonstrated in tumor cells, this same mechanism of action may lead to increased miR-224 expression and potential miR-224-mediated activation of normal resident fibroblasts in the premalignant and PDA microenvironment. Conversely, endogenous inhibition of miR-224 in KPC CAFs did not affect cell proliferation or invasion, but rather increased cell migration, an effect possibly mediated by significant downregulation of Shisa2 in miR-224-inhibited CAFs quantified by RNA-seq. Shisa2, a negative regulator of FGF signaling[21], may promote cell migration upon downregulation in KPC CAFs. Although miR-224 inhibition has been shown to reduce pro-tumorigenic functionalities of tumor cells in many cancer types[35,37] the effects of miR-224 inhibition in CAFs have not been reported. Future studies are warranted to determine how best to regulate miR-224 activity in CAFs to revert or reduce their activated phenotype, and to determine if such reversion contributes to reduced tumorigenicity of PDA, either through reduced tumor cell growth and metastasis or through improved anticancer therapy access to the PDA TME, or both.

The in vivo studies herein, demonstrate that miR-21 inhibition produces therapeutic effects at multiple stages of PDA development. It was found that early systemic administration of the LNA-miR-21 inhibitor significantly decreased the occurrence of high-grade PanINs and PDA in KPC mice. The study also shows that inhibiting miR-21 may be a promising strategy to prevent or slow the development of other KRAS-driven cancers. The data are consistent that miR-21 is an oncogenic miRNA (oncomir) and that its inhibition impedes tumorigenesis in vivo. Utilizing a doxycycline-inducible miR-21$^{LSL\text{-}Tetoff}$ mouse model, induction of miR-21 produced pre-B-cell lymphoma, while miR-21 inactivation led to complete tumor regression[38]. Additionally, in a spontaneous transgenic mouse model of KRAS-driven NSCLC, overexpression of miR-21 enhanced tumorigenesis while knock-out of miR-21 reduced tumor formation in KRAS$^{LA2}$ mice[39]. In the study herein, it is reported that early systemic miR-21 inhibition can specifically impede early mKRAS-driven PDA tumorigenesis.

The data herein, demonstrate that miR-21 is a potential diagnostic marker for the presence of PanINs and PDA due to miR-21's increased expression throughout premalignant to PDA development[40,41]. Stable exosome encapsulated miR-21 is also elevated in the serum of patients with premalignancies and PDA, demonstrating that miR-21 is a potential circulating diagnostic marker for noninvasive early and established PDA screening reflective of increased in-tissue expression[42,43]. Therefore, elevated levels of miR-21 may indicate when miR-21 inhibition treatment should be initiated during early disease development.

The studies herein, also demonstrate that miR-21 is an important regulator of KPC tumor cell function both in vitro and in vivo. However, increasing evidence supports that miR-21 is also a regulator of fibroblast activation and CAF functionality. miR-21 expression is increased in CAFs compared to normal fibroblasts and miR-21 overexpression in normal fibroblasts enhances levels of CAF-specific markers, cell motility, and proliferation, indicating that miR-21, like miR-224, may induce CAF formation[44,45]. Moreover, inhibition of miR-21 reduces CAF migration, invasion, and proliferation[44]. miR-21 achieves this regulation in fibroblasts by directly targeting and downregulating SMAD7, an inhibitor of the TGFβ pathway, thereby sensitizing fibroblasts to TGFβ-mediated CAF formation and fibrosis[46]. In addition to cancer models, fibroblast activation in models of diabetic nephropathy and pulmonary fibrosis has been shown to occur via the same TGFβ/miR-21/SMAD7 regulatory axis[46,47]. In fact, in vivo inhibition of miR-21 attenuated fibrosis in a mouse model of fibrotic lung disease[47], a finding that is highly applicable to PDA intervention because the fibrotic stroma is an integral component of the TME that propagates PDA. Furthermore, the findings that miR-21 inhibition reduces fibrosis provides another mechanism of action for the PanIN-intercepting efficacy of the early systemic miR-21 inhibitor treatment reported in this study. Systemic dosing of LNA-miR-21 inhibitor exposed the entire premalignant microenvironment to miR-21 inhibition which inhibited transformed epithelial cells and possibly the activation of fibroblasts.

In addition to CAFs in the stromal compartment, miR-21 has also been shown to promote pro-tumorigenic immune populations. miR-21 has been shown to induce the polarization of tumor-supportive anti-inflammatory M2 macrophages[48], the differentiation of naïve CD4$^+$ T cells to T regulatory cells (Tregs)[49], and the expansion of myeloid-derived suppressor cells (MDSCs) that exhibit augmented suppressive capabilities upon miR-21 overexpression[50]. Inhibition of miR-21 in the premalignant microenvironment may act to simultaneously reduce fibrosis and suppress the generation of immunosuppressive cell populations, which may cumulatively delay premalignant progression and reduce tumor growth. Therefore, miR-21 exerts its oncogenic effects on multiple cell populations, providing abundant evidence for inhibiting this miRNA in early disease progression. miR-21 inhibition shows efficacy as a monotherapy; however, future studies should test miR-21 inhibition in combination with other agents to modulate several components of the TME simultaneously to more effectively impede disease development.

In summary, it is shown herein, that miR-21 and miR-224 are dysregulated throughout early premalignant progression to established PDA, and demonstrate cell-specific overexpression in the developing microenvironment. These data provide new opportunities for intercepting KRAS-driven premalignancy through impeding epithelial cell transformation and by reducing the PDA stromal barrier to therapeutic access.

Example 2: Establishment of Primary Cell Lines from Growing PDAs in KPC Mice to Evaluate the miRNAs Regulatory Functions in Fibroblast and Epithelial Derived Sub-Populations All PanINs and PDAs recruit activated fibroblasts that are a dominant cell type within the dense stroma of the evolving TME. Therefore, as a first step in understanding the role of miRNAs in PDA regulation, fibroblast-derived and epithelial-derived primary cell lines from actively growing PDA tumors in KPC mice. In vivo growing KPC tumors were excised to generate both CAFs and tumor epithelial cell lines. Normal pancreatic associated fibroblasts (PNAFs), the resident fibroblasts of the normal pancreas, were isolated from pancreata of WT mice as the fibroblast control cell line. Normal pancreatic epithelial cells derived from WT mice were purchased from Cell Biologics as the epithelial control cell line.

Figures 7A, 7B, 7C, 7D, 7E, 7F, 7G, 7H:
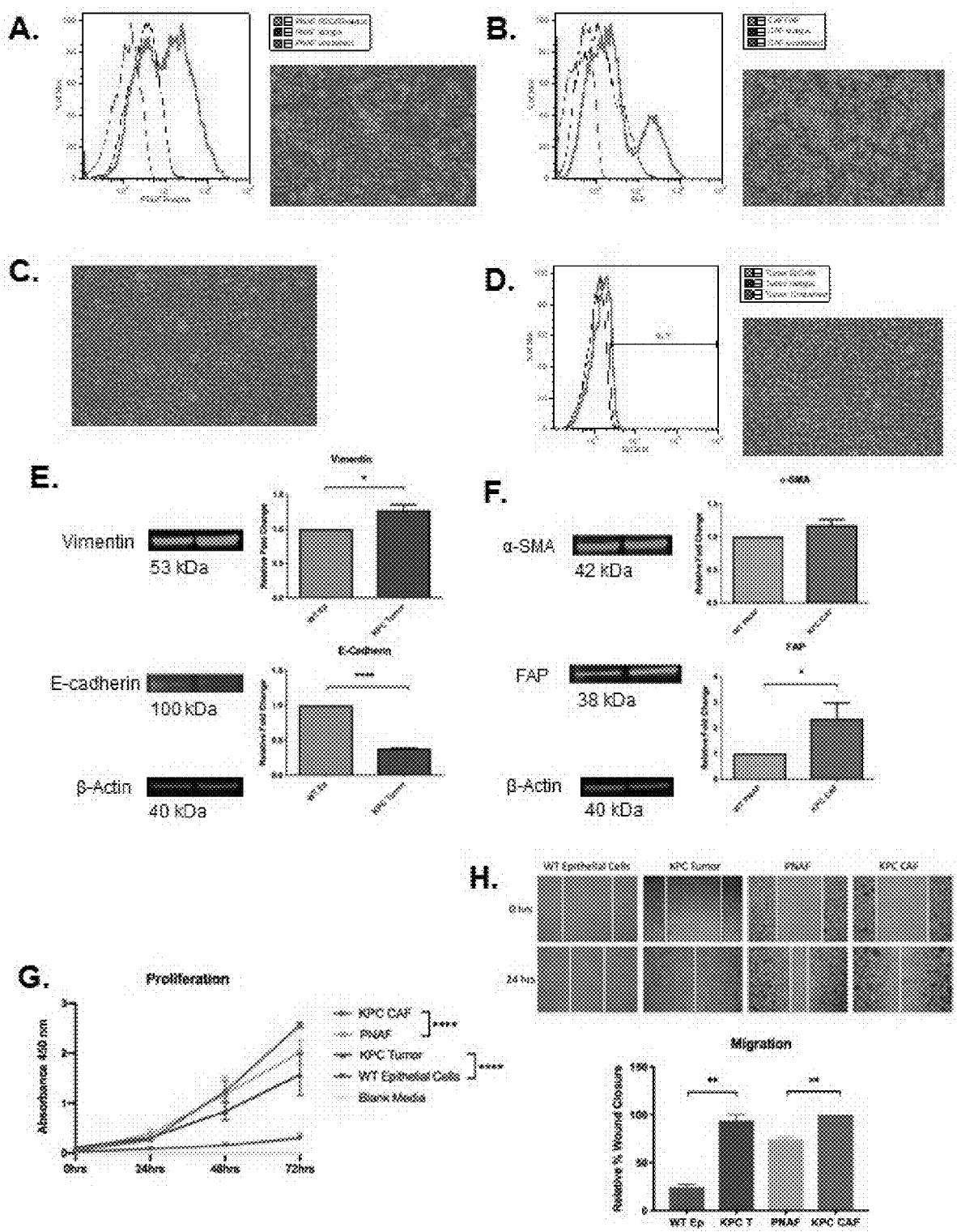
FIGS. 7A-7H are a series of plots, graphs and images demonstrating the establishment of primary cell lines of the TME for in vitro functional studies. FACs sorting was employed to isolate and enrich for each cell type, while Western blot analysis, proliferation and migration assays were used to validate phenotypic differences based on marker expression and cell functionalities.

FACS was performed to further enrich for each population. To isolate a pure population of PNAFs, platelet-derived growth factor receptor alpha (PDGFRα) was utilized as a surface marker for stromal cells of mesenchymal origin[61] (FIG. 7A). For CAFs, sorting was accomplished by using fibroblast activation protein (FAP), which is selectively expressed on activated stromal fibroblasts in epithelial cancers[62] (FIG. 7B). To increase the purity of KPC tumor epithelial cells, sorting was accomplished by using epithelial cell adhesion molecule (EpCAM), a surface glycoprotein exclusively expressed on epithelia and epithelial-derived tumors[63] (FIG. 7D). The post-sort morphology of each cell line is depicted next to the flow cytometric analysis of the marker that was used to establish each primary cell line. The classic spindle shape of fibroblasts is exhibited by PNAFs and KPC CAFs (FIGS. 7A-7B), whereas the classic cuboidal morphology of epithelial cells is exhibited by WT pancreatic epithelial cells and KPC tumor cells (FIG. 7C-7D).

To further validate these cell lines, protein expression of phenotypic markers specific to each cell type by western blot analysis were quantified. To distinguish between WT pancreatic epithelial cells and KPC tumor epithelial cells, the expression of epithelial markers vimentin and E-cadherin were compared. The significant upregulation of vimentin and downregulation of E-cadherin in KPC tumor cells confirms its transformed, mesenchymal phenotype as compared to the untransformed WT epithelial cells (FIG. 7E). To validate PNAFs and CAFs, the expression of α-smooth muscle actin (α-SMA) and FAP was quantified. The increased expression of FAP and upregulation of α-SMA in CAFs confirms its activated state compared to PNAFs (FIG. 7F).

A defining phenotype of fully transformed and activated cells is increased proliferation. The WST-8 based CCK8 proliferation assay was used to compare the proliferation of KPC derived CAFs and tumor cells to PNAFs and WT epithelial cells, respectively. As expected, KPC CAFs and tumor cells proliferate more vigorously than their WT counterparts (PNAFs and WT epithelial cells, respectively) (FIG. 7G).

Increased cell migration is another acquired characteristic of a transformed and activated phenotype. Utilizing the scratch assay or wound-healing assay, the rate at which the primary cell lines migrated to close a partition generated by a scratch made on a confluent cell surface was quantified. After only 24 hours in culture, KPC tumor cells achieved 94% wound closure whereas WT pancreatic epithelial cells achieved only 24% wound closure, demonstrating the significantly increased migratory capacities of transformed KPC tumor cells (FIG. 7H). Similarly, KPC CAFs achieved 100% wound closure compared to PNAFs that only migrated to cover 74% of the partition, indicating that KPC CAFs migrate more rapidly than PNAFs. Thus, the quantified differences in marker expression, cell proliferation, and migration confirm the phenotypes of these primary cell lines.

miR-21 Expression is Increased in KPC Tumor Cells Whereas miR-224 Expression is Increased in KPC CAFs Expression levels of the 4 most dysregulated miRNA candidates (miR-21, miR-16, miR-19b, and miR-224) were further assessed in primary PDA cell lines relative to the WT cells. All 4 sequences are fully conserved between mice and humans, allowing for future human investigation and potential therapeutic targeting. FIG. 8 shows the relative fold changes in expression of miR-21, miR-16, miR-19b, and miR-224 in KPC tumor and CAF cell lines as compared to WT pancreatic epithelial cells and pancreatic normal associated fibroblasts (PNAFs), respectively. miR-21 expression is significantly increased by 7-fold specifically in KPC tumor cells as compared to WT epithelial cells, and miR-224 expression is significantly increased by 10-fold specifically in KPC CAFs as compared to PNAFs. These data demonstrate that the expression of these two miRNAs are each specifically upregulated in a subset of PDA TME cells. Furthermore, the activation state of each cell type may regulate or be regulated by changes in miRNA expression.

LNA-miR-21 and LNA-miR-224 do not Adversely Impact KPC Mouse Growth

Figures 12A, 12B:
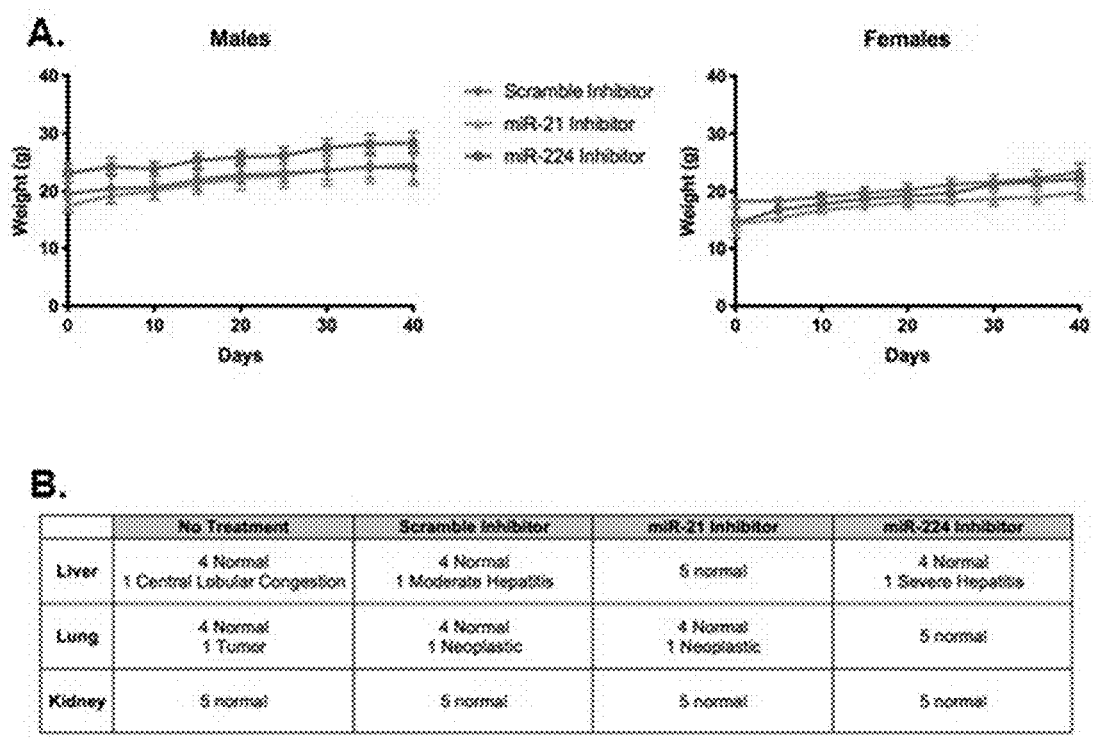
FIGS. 12A and 12B are a series of plots and a table showing the toxicity of systemic miRNA inhibitor dosing in KPC mice.

General assessment of drug toxicity was performed by monitoring mouse weights and examining the histopathology of major organ sites of drug accumulation (FIGS. 12A-12B). Weights of treated male and female mice were measured every 5 days throughout the dosing regimen. All weights, regardless of treatment or gender, increased consistently demonstrating that the inhibitors did not adversely affected male or female growth (FIG. 12A). Livers, lungs and kidneys were isolated at the end of the dosing regimen and histologically assessed for tissue toxicity[64] (FIG. 12B).

REFERENCES

1. Hidalgo M. Pancreatic Cancer. *N Engl J Med.* 2010; 362(17):1605-1622. doi:10.1056/NEJMra0901557
2. Collins M A, Bednar F, Zhang Y, Brisset J C, Galban S, Galban C J, et al. Oncogenic Kras is required for both the initiation and maintenance of pancreatic cancer in mice. *J Clin Invest.* 2012; 122(2):639-653. doi:10.1172/JCI59227
3. di Magliano M P, Logsdon C D. Roles for KRAS in pancreatic tumor development and progression. *Gastroenterology.* 2013; 144(6):1220-1229. doi:10.1053/j.gastro.2013.01.071
4. Lou E, Subramanian S, Steer C J. Pancreatic cancer: modulation of KRAS, MicroRNAs, and intercellular communication in the setting of tumor heterogeneity. *Pancreas.* 2013; 42(8):1218-1226. doi:10.1097/MPA.0000000000000007
5. Hingorani S R, Petricoin E F, Maitra A, Rajapakse V, King C, Jacobetz M A, et al. Preinvasive and invasive ductal pancreatic cancer and its early detection in the mouse. *Cancer Cell.* 2003; 4(6):437-450. doi:10.1016/S1535-6108(03)00309-X
6. Kanda M, Matthaei H, Wu J, Hong S M, Yu J, Borges M, et al. Presence of somatic mutations in most early-stage pancreatic intraepithelial neoplasia. *Gastroenterology.* 2012; 142(4). doi:10.1053/j.gastro.2011.12.042
7. Eser S, Schnieke A, Schneider G, Saur D. Oncogenic KRAS signalling in pancreatic cancer. *Br J Cancer.* 2014; 111(5):817-822. doi:10.1038/bjc.2014.215
8. von Ahrens D, Bhagat T D, Nagrath D, Maitra A, Verma A. The role of stromal cancer-associated fibroblasts in pancreatic cancer. *J Hematol Oncol.* 2017; 10(1):76. doi:10.1186/s13045-017-0448-5
9. Morris J P, Wang S C, Hebrok M. KRAS, Hedgehog, Wnt and the twisted developmental biology of pancreatic ductal adenocarcinoma. *Nat Rev Cancer.* 2010; 10(10): 683-695. doi:10.1038/nrc2899
10. Choi M, Bien H, Mofunanya A, Powers S. Challenges in Ras therapeutics in pancreatic cancer. *Semin Cancer Biol.* 2019; 54:101-108. doi:10.1016/j.semcancer.2017.11.015
11. Bournet B, Buscail C, Muscari F, Cordelier P, Buscail L. Targeting KRAS for diagnosis, prognosis, and treatment of pancreatic cancer: Hopes and realities. *Eur J Cancer.* 2016; 54:75-83. doi:10.1016/j.ejca.2015.11.012
12. Keenan B P, Saenger Y, Kafrouni M I, Leubner A, Lauer P, Maitra A, et al. A listeria vaccine and depletion of t-regulatory cells activate immunity against early stage pancreatic intraepithelial neoplasms and prolong survival of mice. *Gastroenterology.* 2014; 146(7):1784-1794. doi: 10.1053/j.gastro.2014.02.055
13. Rupaimoole R, Slack F J. MicroRNA therapeutics: towards a new era for the management of cancer and other diseases. *Nat Rev Drug Discov.* 2017; 16(3):203-222. doi:10.1038/nrd.2016.246
14. Nana-Sinkam S P, Croce C M. Clinical Applications for microRNAs in Cancer. *Clin Pharmacol Ther.* 2013; 93(1): 98-104. doi:10.1038/clpt.2012.192
15. Taucher V, Mangge H, Haybaeck J. Non-coding RNAs in pancreatic cancer: challenges and opportunities for clinical application. *Cell Oncol.* 2016; 39(4):295-318. doi:10.1007/s13402-016-0275-7
16. Seto A G, Beatty X, Lynch J M, Hermreck M, Tetzlaff M, Duvic M, et al. Cobomarsen, an oligonucleotide inhibitor of miR-155, co-ordinately regulates multiple survival pathways to reduce cellular proliferation and survival in cutaneous T-cell lymphoma. *Br J Haematol.* 2018; 183(3):428-444. doi:10.1111/bjh.15547
17. Hingorani S R, Wang L, Multani A S, Combs C, Deramaudt T B, Hruban R H, et al. Trp53R172H and KrasG12D cooperate to promote chromosomal instability and widely metastatic pancreatic ductal adenocarcinoma in mice. *Cancer Cell.* 2005; 7(5):469-483. doi:10.1016/j.ccr.2005.04.023
18. Sheedy F J. Turning 21: Induction of miR-21 as a key switch in the inflammatory response. *Front Immunol.* 2015; 6(January). doi:10.3389/fimmu.2015.00019
19. Cui R, Meng W, Sun H-L, Kim T, Ye Z, Fassan M, et al. MicroRNA-224 promotes tumor progression in nonsmall cell lung cancer. *Proc Natl Acad Sci USA.* 2015; 112(31): E4288-97. doi:10.1073/pnas.1502068112
20. Luo W, Friedman M S, Shedden K, Hankenson K D, Woolf P J. GAGE: generally applicable gene set enrichment for pathway analysis. *BMC Bioinformatics.* 2009; 10:161. doi:10.1186/1471-2105-10-161
21. Aizawa S, Yamamoto A, Takehara S, Takahashi M, Nagano T. Shisa2 promotes the maturation of somitic precursors and transition to the segmental fate in *Xenopus* embryos. *Development.* 2006; 133(23):4643-4654. doi: 10.1242/dev.02657
22. Stehbens S J, Ju R J, Adams M N, Perry S R, Haass N K, Bryant D M, et al. FGFR2-activating mutations disrupt cell polarity to potentiate migration and invasion in endometrial cancer cell models. *J Cell Sci.* 2018; 131(15). doi:10.1242/jcs.213678
23. Criscitiello C, Esposito A, Curigliano G. Targeting FGFR pathway in breast cancer. *Breast Cancer Innov Res Manag.* 2017; 37:819-822. doi:10.1007/978-3-319-48848-6_70
24. Rucki A A, Foley K, Zhang P, Xiao Q, Kleponis J, Wu A A, et al. Heterogeneous stromal signaling within the tumor microenvironment controls the metastasis of pancreatic cancer. *Cancer Res.* 2017; 77(1):41-52. doi: 10.1158/0008-5472.CAN-16-1383
25. Hagedorn P H, Persson R, Funder E D, Albaek N, Diemer S L, Hansen D J, et al. Locked nucleic acid: modality, diversity, and drug discovery. *Drug Discov Today.* 2018; 23(1):101-114. doi:10.1016/j.drudis.2017.09.018
26. Aran D, Hu Z, Butte A J. xCell: Digitally portraying the tissue cellular heterogeneity landscape. *Genome Biol.* 2017; 18(1). doi:10.1186/s13059-017-1349-1
27. Luo M, Tan X, Mu L, Luo Y, Li R, Deng X, et al. MiRNA-21 mediates the antiangiogenic activity of metformin through targeting PTEN and SMAD7 expression and PI3K/AKT pathway. *Sci Rep.* 2017; 7. doi:10.1038/srep43427
28. Xue X, Liu Y, Wang Y, Meng M, Wang K, Zang X, et al. MiR-21 and MiR-155 promote non-small cell lung cancer progression by downregulating SOCS1, SOCS6, and PTEN. *Oncotarget.* 2016; 7(51):84508-84519. doi: 10.18632/oncotarget.13022
29. Frankel L B, Christoffersen N R, Jacobsen A, Lindow M, Krogh A, Lund A H. Programmed cell death 4 (PDCD4) is an important functional target of the microRNA miR-21 in breast cancer cells. *J Biol Chem.* 2008; 283(2):1026-1033. doi:10.1074/jbc.M707224200
30. Zhao Q, Chen S, Zhu Z, Yu L, Ren Y, Jiang M, et al. miR-21 promotes EGF-induced pancreatic cancer cell proliferation by targeting Spry2. *Cell Death Dis.* 2018; 9(12):1157. doi:10.1038/s41419-018-1182-9
31. Zhu S, Si M L, Wu H, Mo Y Y. MicroRNA-21 targets the tumor suppressor gene tropomyosin 1 (TPM1). *J Biol Chem.* 2007; 282(19):14328-14336. doi:10.1074/jbc.M611393200
32. Shi L, Middleton J, Jeon Y J, Magee P, Veneziano D, Lagana A, et al. KRAS induces lung tumorigenesis through microRNAs modulation article. *Cell Death Dis.* 2018; 9(2). doi:10.1038/s41419-017-0243-9
33. Gong B, Liu W W, Nie W J, Li D F, X Z J, Liu C, et al. MiR-21/RASA1 axis affects malignancy of colon cancer cells via RAS pathways. *World J Gastroenterol.* 2015; 21(5):1488-1497. doi:10.3748/wjg.v21.i5.1488
34. Petrova V, Annicchiarico-Petruzzelli M, Melino G, Amelio I. The hypoxic tumour microenvironment. *Oncogenesis.* 2018; 7(1):10. doi:10.1038/s41389-017-0011-9
35. He C, Wang L, Zhang J, Xu H. Hypoxia-inducible microRNA-224 promotes the cell growth, migration and invasion by directly targeting RASSF8 in gastric cancer. *Mol Cancer.* 2017; 16(1). doi:10.1186/s12943-017-0603-1
36. Scisciani C, Vossio S, Guerrieri F, Schinzari V, De Iaco R, D'Onorio De Meo P, et al. Transcriptional regulation of miR-224 upregulated in human HCCs by NFκB inflammatory pathways. *J Hepatol.* 2012; 56(4):855-861. doi: 10.1016/j.jhep.2011.11.017
37. Zhu G, Zhou L, Liu H, Shan Y, Zhang X. MicroRNA-224 promotes pancreatic cancer cell proliferation and migration by targeting the TXNIP-mediated HIF1α pathway. *Cell Physiol Biochem.* 2018; 48(4):1735-1746. doi: 10.1159/000492309
38. Medina P P, Nolde M, Slack F J. OncomiR addiction in an in vivo model of microRNA-21-induced pre-B-cell lymphoma. *Nature.* 2010; 467(7311):86-90. doi:10.1038/nature09284
39. Hatley M E, Patrick D M, Garcia M R, Richardson J A, Bassel-Duby R, van Rooij E, et al.
Modulation of K-Ras-dependent lung tumorigenesis by MicroRNA-21. *Cancer Cell.* 2010; 18(3):282-293. doi: 10.1016/j.ccr.2010.08.013
40. Yu J, Li A, Hong S-M, Hruban R H, Goggins M. MicroRNA alterations of pancreatic intraepithelial neoplasias. *Clin Cancer Res.* 2012; 18(4):981-992. doi: 10.1158/1078-0432.CCR-11-2347
41. du Rieu M C, Torrisani J, Selves J, Al Saati T, Souque A, Dufresne M, et al. MicroRNA-21 is induced early in pancreatic ductal adenocarcinoma precursor lesions. *Clin Chem.* 2010; 56(4):603-612. doi:10.1373/clinchem.2009.137364
42. Qu K, Zhang X, Lin T, Liu T, Wang Z, Liu S, et al. Circulating miRNA-21-5p as a diagnostic biomarker for pancreatic cancer: Evidence from comprehensive miRNA expression profiling analysis and clinical validation. *Sci Rep.* 2017; 7(1):1-12. doi:10.1038/s41598-017-01904-z
43. Goto T, Fujiya M, Konishi H, Sasajima J, Fujibayashi S, Hayashi A, et al. An elevated expression of serum exosomal microRNA-191, -21, -451a of pancreatic neoplasm is considered to be efficient diagnostic marker. *BMC Cancer.* 2018; 18(1):1-11. doi:10.1186/s12885-018-4006-5
44. Ali S, Suresh R, Banerjee S, Bao B, Xu Z, Wilson J, et al. Contribution of microRNAs in understanding the pancreatic tumor microenvironment involving cancer associated stellate and fibroblast cells. *Am J Cancer Res.* 2015; 5(3):1251-1264. http://www.ncbi.nlm.nih.gov/pubmed/26046003.
45. Kunita A, Morita S, Irisa T U, Goto A, Niki T, Takai D, et al. MicroRNA-21 in cancer-associated fibroblasts supports lung adenocarcinoma progression. *Sci Rep.* 2018; 8(1). doi:10.1038/s41598-018-27128-3
46. Wang J Y, Gao Y B, Zhang N, Zou D W, Wang P, Zhu Z Y, et al. MiR-21 overexpression enhances TGF-β1-induced epithelial-to-mesenchymal transition by target smad7 and aggravates renal damage in diabetic nephropathy. *Mol Cell Endocrinol.* 2014; 392(1-2):163-172. doi: 10.1016/j.mce.2014.05.018
47. Liu G, Friggeri A, Yang Y, Milosevic J, Ding Q, Thannickal V J, et al. miR-21 mediates fibrogenic activation of pulmonary fibroblasts and lung fibrosis. *J Exp Med.* 2010; 207(8):1589-1597. doi:10.1084/jem.20100035
48. Ren W, Hou J, Yang C, Wang H, Wu S, Wu Y, et al. Extracellular vesicles secreted by hypoxia pre-challenged mesenchymal stem cells promote non-small cell lung cancer cell growth and mobility as well as macrophage M2 polarization via miR-21-5p delivery. *J Exp Clin Cancer Res.* 2019; 38(1). doi:10.1186/s13046-019-1027-0
49. Zhou J, Li X, Wu X, Zhang T, Zhu Q, Wang X, et al. Exosomes released from tumor-associated macrophages transfer miRNAs that induce a Treg/Th17 cell imbalance in epithelial ovarian cancer. *Cancer Immunol Res.* 2018; 6(12):1578-1592. doi:10.1158/2326-6066.CIR-17-0479
50. Li L, Zhang J, Diao W, Wang D, Wei Y, Zhang C Y, et al. MicroRNA-155 and MicroRNA-21 Promote the Expansion of Functional Myeloid-Derived Suppressor Cells. *J Immunol.* 2014; 192(3):1034-1043. doi:10.4049/jimmunol.1301309
51. Foley K, Rucki A A, Xiao Q, et al. Semaphorin 3D autocrine signaling mediates the metastatic role of annexin A2 in pancreatic cancer. *Sci Signal.* 2015; 8(388). doi:10.1126/scisignal.aaa5823
52. Walter K, Omura N, Hong S M, Griffith M, Goggins M. Pancreatic cancer associated fibroblasts display normal allelotypes. *Cancer Biol Ther.* 2008; 7(6):882-888. doi: 10.4161/cbt.7.6.5869
53. Schindelin J, Arganda-Carreras I, Frise E, et al. Fiji: An open-source platform for biological-image analysis. *Nat Methods.* 2012; 9(7):676-682. doi:10.1038/nmeth.2019
54. Li B, Dewey C N. RSEM: accurate transcript quantification from RNA-Seq data with or without a reference genome. *BMC Bioinformatics.* 2011; 12(1):323. doi: 10.1186/1471-2105-12-323
55. Leng N, Dawson J A, Thomson J A, et al. EBSeq: An empirical Bayes hierarchical model for inference in RNA-seq experiments. *Bioinformatics.* 2013; 29(8):1035-1043. doi:10.1093/bioinformatics/btt087
56. Luo W, Friedman M S, Shedden K, Hankenson K D, Woolf P J. GAGE: generally applicable gene set enrichment for pathway analysis. *BMC Bioinformatics.* 2009; 10:161. doi:10.1186/1471-2105-10-161
57. Koutsioumpa M, Chen H W, O'Brien N, et al. MKAD-21 Suppresses the Oncogenic Activity of the miR-21/PPP2R2A/ERK Molecular Network in Bladder Cancer. *Mol Cancer Ther.* 2018; 17(7):1430-1440. doi:10.1158/1535-7163.MCT-17-1049
58. Thorsson V, Gibbs D L, Brown S D, et al. The Immune Landscape of Cancer. *Immunity.* 2018; 48(4):812-830.e14. doi:10.1016/j.immuni.2018.03.023
59. Liu J, Lichtenberg T, Hoadley K A, et al. An Integrated TCGA Pan-Cancer Clinical Data Resource to Drive High-Quality Survival Outcome Analytics. *Cell.* 2018; 173(2): 400-416.e11. doi:10.1016/j.cell.2018.02.052
60. Aran D, Hu Z, Butte A J. xCell: Digitally portraying the tissue cellular heterogeneity landscape. *Genome Biol.* 2017; 18(1). doi:10.1186/s13059-017-1349-1
61. Klinkhammer B M, Floege J, Boor P. PDGF in organ fibrosis. *Mol Aspects Med.* 2018; 62:44-62. doi:10.1016/j.mam.2017.11.008
62. Xia Q, Zhang F-F, Geng F, et al. Anti-tumor effects of DNA vaccine targeting human fibroblast activation protein a by producing specific immune responses and altering tumor microenvironment in the 4T1 murine breast cancer model. *Cancer Immunol Immunother.* 2016; 65(5): 613-624. doi:10.1007/s00262-016-1827-4
63. Rhim A D, Mirek E T, Aiello N M, et al. EMT and dissemination precede pancreatic tumor formation. *Cell.* 2012; 148(1-2):349-361. doi:10.1016/j.cell.2011.11.025
64. Straarup E M, Fisker N, Hedtjärn M, et al. Short locked nucleic acid antisense oligonucleotides potently reduce apolipoprotein B mRNA and serum cholesterol in mice and non-human primates. *Nucleic Acids Res.* 2010; 38(20):7100-7111. doi:10.1093/nar/gkq457

Example 3: A Human Model of PDAC

Figures 13A, 13B, 13C, 13D:
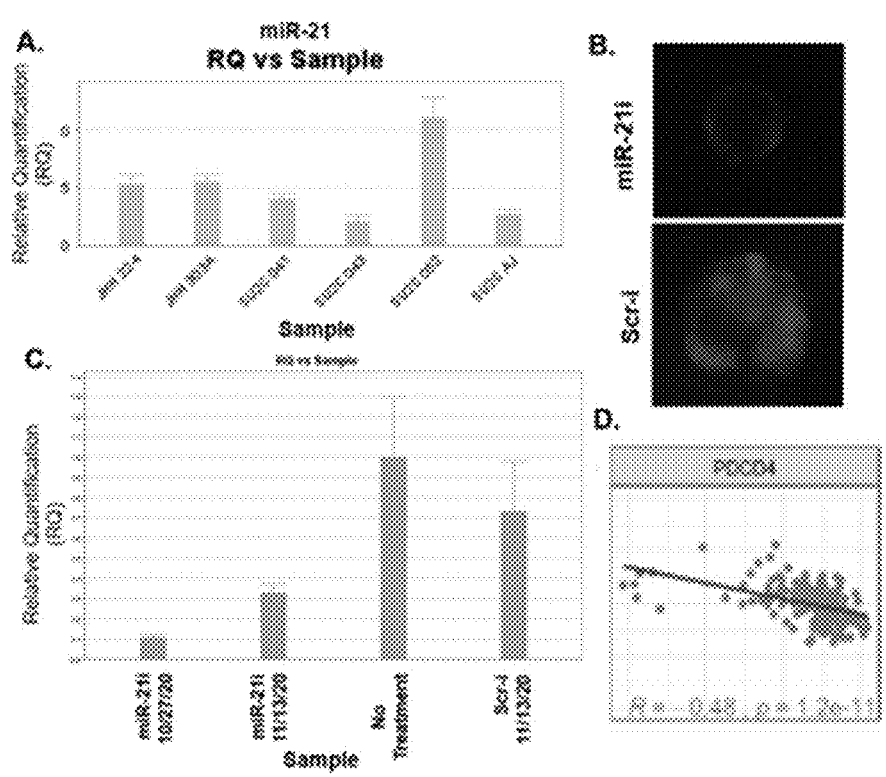
FIGS. 13A-13D are a series of graphs, plots and images showing the miR-21 endogenous expression and inhibition.

The human model of PDAC that captures interpatient heterogeneity to enhances the understanding of miR-21's role in human PDAC tumorigenesis and progression[2-6]. In translating the murine findings, it was found that endogenous miR-21 levels in PDO models of PDAC are heterogeneous (FIGS. 13A-13D). Further, and miR-21 expression can be modulated in human models using RNAi technologies (FIGS. 13A-13C).

Materials and Methods

Organoid Culturing: Six patient-derived organoid (PDO) lines were established from endoscopic biopsies and surgical specimens. Patients included were diagnosed with PDAC and were enrolled into an IRB-approved tissue acquisition protocol from Massachusetts General Hospital (MGH) or Johns Hopkins Hospital. The endoscopic ultrasound-directed biopsies obtained at MGH were shipped on ice overnight in transfer media with Penicillin/Streptomycin. The surgical tumor samples were dissociated with Collagenase Crude Type XI (Sigma-Aldrich, C9407-1G) and suspended in Matrigel (Corning, 356231). Cultures were then established and maintained as previously described[1].

Lentiviral Transduction: Six stable miR-21 knock-down PDO lines were generated using LENTI-PAC™ HIV Expression Packaging Kit GeneCopoeia, U.S. (LT001). miR-21 inhibitor and non-specific scramble inhibitor constructs were purchased from inventoried GeneCopoeia vectors (hsa-miR-21-5p: HmiR-AN0316-AM031; scramble: CmiR-AN0001-AM03). Pseudovirus was prepared using 293Ta packaging cells (GeneCopoeia, LT008) per manufacturer protocol. Virus was concentrated using the LENTI-PAC™ Lentivirus Concentration Solution (GeneCopoeia LT007). For cell transduction, PDO lines were plated in a 48 well plate with the concentrated virus and centrifuged at 1700 RPM in a 4° C. centrifuge for 1 hour. Cells were then incubated with virus at 37° C. for 6 hours. After the incubation period the cells were washed and plated in Matrigel. Serial antibiotic selection with Hygromycin Gold (Invivogen, ant-hg-1) was initiated 2 days after plating.

Imaging: To demonstrate successful construct incorporation, organoids were imaged weekly using a Nikon TE200 Inverted Fluorescence & Phase Contrast Tissue Culture microscope at the 20× objective lens to identify the presence of the mCherry reporter. Fluorescent images were obtained following an exposure time of 2 seconds while white light images were obtained following a 40 ms exposure.

RNA Extraction: To demonstrate successful miRNA knock-down and evaluate expression of mRNA targets, RNA extraction (Qiagen, Kit miRNeasy Mini Kit; 217004) was completed for each cell line under the following conditions: non-transduced, transduced with the scramble inhibitor, transduced with the miR-21 inhibitor.

miRNA Reverse Transcription: cDNA was generated using TAQMAN™ MicroRNA Reverse Transcription Kit (ThermoFisher Scientific, 4366596). Applied Biosystems probes for miR-21 and snRNA U6 (has-miR-21: RT000397; U6: RT001973) were used to generate cDNA for the miRNAs of interest. Reverse transcription was completed using the Applied Biosystems GeneAmp PCR System 9700. NanoDrop 2000 (Thermo Scientific) was used to quantify the cDNA product.

mRNA Reverse Transcription: cDNA was generated using Invitrogen TAQMAN Reverse Transcription Reagents (Catalog Number: N8080234). Reverse transcription was completed using the Applied Biosystems GeneAmp PCR System 9700. NanoDrop 2000 (Thermo Scientific) was used to quantify the cDNA product.

miRNA PCR: Real-time quantitative PCR was completed according to the ThermoFisher TaqMan Gene Expression Assays Protocol (TaqMan Universal PCR Master Mix (2×), 430571) using Applied Biosystems probes (miR-21 Assay ID: 000397; U6 snRNA assay ID: 001973). miRNA was quantified as previously described using relative quantitation with snRNA U6 as the endogenous control[7]. PCR was run on the StepOne™ Real-Time PCR System (ThermoFisher Scientific, 4376357). Data were analyzed using Applied Biosystems StepOne™ Software v2.3 Real-Time PCR Decision Tree.

mRNA PCR: Real-time quantitative PCR was completed using the ThermoFisher TaqMan Gene Expression Assays Protocol. mRNA targets included PDCD4 (Hs00377253) with 18S (Hs99999901) as the endogenous control. RNA was quantified as previously described using relative quantitation and 18S ribosomal RNA as the endogenous control[7]. PCR was run on the StepOne™ Real-Time PCR System (ThermoFisher Scientific, 4376357). Data were analyzed using Applied Biosystems StepOne™ Software v2.3 Real-Time PCR Decision Tree.

Evaluation of the Cancer Genome Atlas (TCGA): MiRNA expression data from TCGA was interrogated to evaluate for an mRNA target correlation with miR expression[8,9]. MicroRNA expression data from TCGA was obtained from the National Cancer Institute Genome Data Commons[8]. R version 3.6 was used to subset the data frame to isolate the PDAC cohort. MicroRNA expression data was subject to variance stabilization transformation prior to statistical analysis. MiR-21 mRNA targets were obtained from miR-WALK and used to assess the relationship between miR-21 and mRNA targets[10,11].

Results

Stable Lentiviral Knock-Down of miR-21 Expression: Six stable miR-21 knock-down PDO lines were generated from 6 different patients with a range of endogenous miR-21 expression as evaluated by qPCR (FIG. 13A). Sustained incorporation of the construct was visualized by examining the presence of the mCherry reporter (FIG. 13B). Successful knock-down was evaluated with qPCR following serial selection with Hygromycin Gold. Percent knock-down improved over time with ongoing antibiotic selection with maximum knock-down of ~85% of the endogenous expression (FIG. 13C).

Figure 14:
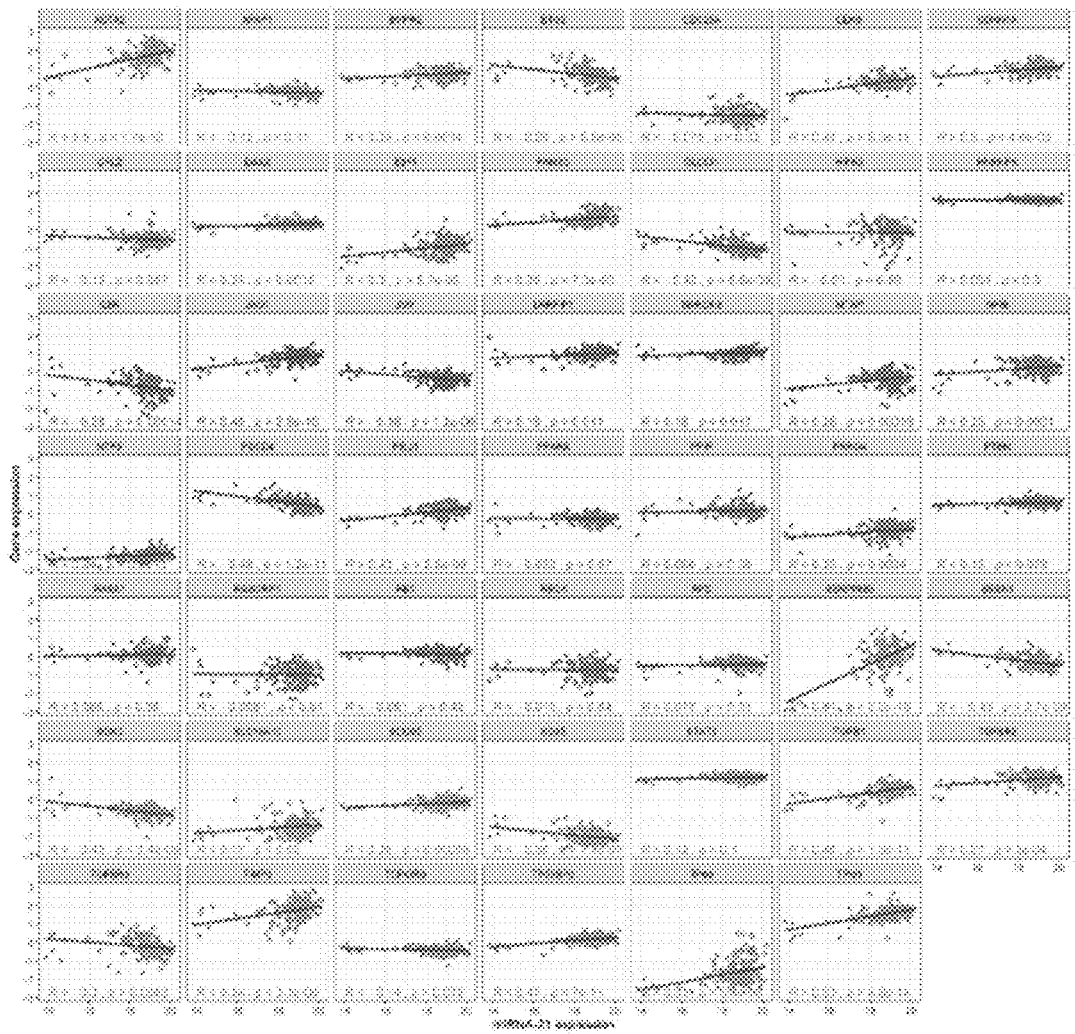
FIG. 14 is a series of plots demonstrating the relationship of miR-21 expression to target mRNA expression is heterogeneous in TCGA PDAC cohort. x-axis: miR-21 expression; y-axis: target mRNA expression.
Figure 15:
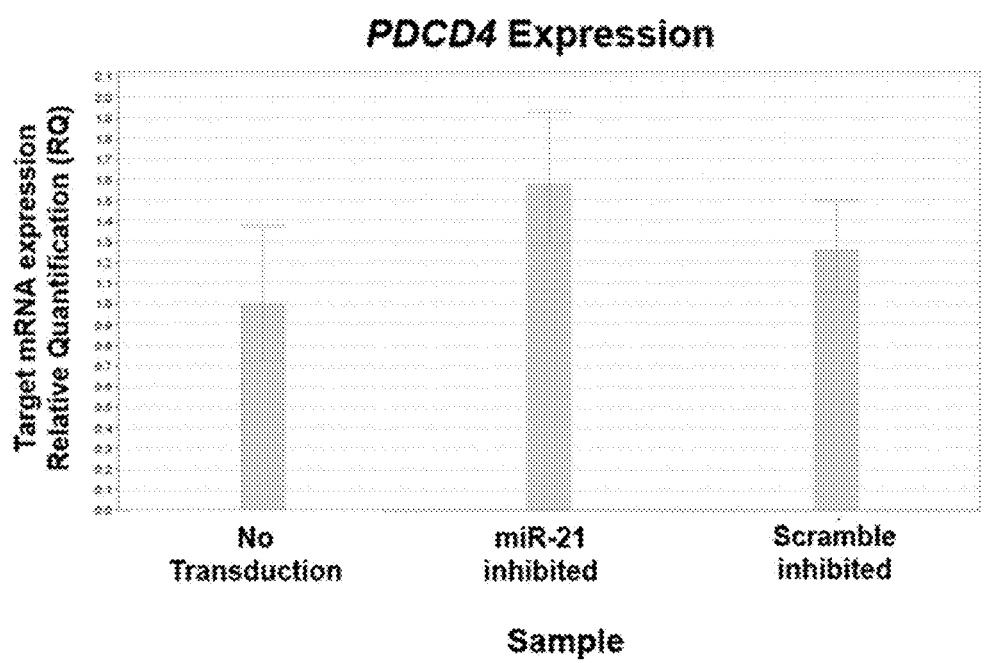
FIG. 15 is a graph demonstrating that miR-21 inhibition results in an increase in PDCD4 expression in a PDO model of PDAC. n=3 technical replicates per condition.

TCGA Interrogation of miRWALK Targets OF miR-21: To complement the molecular study, an analysis of miR-21's 48 miRWALK[10,11] mRNA targets in The Cancer Genome Atlas (TCGA) PDAC cohort demonstrated a heterogeneous relationship between miR-21 expression and expression of mRNA targets (FIG. 14). Prominently, an inverse relationship was identified between miR-21 expression and the expression of one of its target mRNAs: programmed cell death protein 4 (PDCD4). This finding further supports a role of miR-21 in the regulation of critical determinants of cellular fate (FIG. 13D). PDCD4 can inhibit the ERK/MAPK pathway and ultimately suppress cytokine expression; it is also upregulated in apoptosis[12]. Similarly, PDCD4 was described as a functional target of miR-21 in breast cancer cells, with miR-21 inhibition resulting in decreased cell proliferation[13].

qPCR Evaluation of mRNA Targets Following miR-21 Knock-Down: After validation of successful miR-21 knock-down, qPCR was used to examine the relationship between miR-21 gene target expression and miR-21 expression. PDCD4 has been evaluated as the pilot target because of its biological relevance and the inverse relationship identified between miR-21 expression and gene target expression in the query of TCGA. Similar to the computational evaluation, PDCD4 expression increased following miR-21 knock-down providing evidence that miR-21 knock-down as a potential mechanism for regaining the tumor suppressor function of PDCD4 in PDAC (FIG. 15).

REFERENCES FOR EXAMPLE 3

1. Seppala T T, Zimmerman J W, Sereni E, et al. Patient-derived Organoid Pharmacotyping is a Clinically Tractable Strategy for Precision Medicine in Pancreatic Cancer. *Ann Surg.* 2020; 272(3):427-435. doi:10.1097/sla.0000000000004200
2. Baker L A, Tiriac H, Clevers H, Tuveson D A. Modeling Pancreatic Cancer with Organoids. *Trends in Cancer.* 2016; 2(4):176-190. doi:10.1016/j.trecan.2016.03.004
3. Moreira L, Bakir B, Chatterji P, Dantes Z, Reichert M, Rustgi A K. Pancreas 3D Organoids: Current and Future Aspects as a Research Platform for Personalized Medicine in Pancreatic Cancer. *Cmgh.* 2018; 5(3):289-298. doi:10.1016/j.jcmgh.2017.12.004
4. Boj S F, Hwang C Il, Baker L A, et al. Organoid models of human and mouse ductal pancreatic cancer. *Cell.* 2015; 160(1-2):324-338. doi:10.1016/j.cell.2014.12.021
5. Tiriac H, Bucobo J C, Tzimas D, et al. Successful creation of pancreatic cancer organoids by means of EUS-guided fine-needle biopsy sampling for personalized cancer treatment. *Gastrointest Endosc.* 2018; 87(6):1474-1480. doi:10.1016/j.gie.2017.12.032
6. Tsai S, McOlash L, Palen K, et al. Development of primary human pancreatic cancer organoids, matched stromal and immune cells and 3D tumor microenvironment models. *BMC Cancer.* 2018; 18:335. doi:10.1186/s12885-018-4238-4
7. Chu N J, Anders R A, Fertig E J, et al. Inhibition of miR-21 regulates mutant KRAS effector pathways and intercepts pancreatic ductal adenocarcinoma development. *Cancer Prev Res.* Published online May 14, 2020: canprevres.0053.2020. doi:10.1158/1940-6207.capr-20-0053
8. Thorsson V, Gibbs D L, Brown S D, et al. The Immune Landscape of Cancer. *Immunity.* 2018; 48(4):812-830.e14. doi:10.1016/j.immuni.2018.03.023
9. Liu J, Lichtenberg T, Hoadley K A, et al. An Integrated TCGA Pan-Cancer Clinical Data Resource to Drive High-Quality Survival Outcome Analytics. *Cell.* 2018; 173(2): 400-416.ell. doi:10.1016/j.cell.2018.02.052
10. Dweep H, Sticht C, Pandey P, Gretz N. MiRWalk—Database: Prediction of possible miRNA binding sites by "walking" the genes of three genomes. *J Biomed Inform.* 2011; 44(5):839-847. doi:10.1016/j.jbi.2011.05.002
11. Dweep H, Gretz N. MiRWalk2.0: A comprehensive atlas of microRNA-target interactions. *Nat Methods.* 2015; 12(8):697. doi:10.1038/nmeth.3485
12. Jiang Y, Jia Y, Zhang L. Role of programmed cell death 4 in diseases: a double-edged sword. *Cell Mol Immunol.* 2017; 14(11):884-886. doi:10.1038/cmi.2017.84
13. Frankel L B, Christoffersen N R, Jacobsen A, Lindow M, Krogh A, Lund A H. Programmed cell death 4 (PDCD4) is an important functional target of the microRNA miR-21 in breast cancer cells. *J Biol Chem.* 2008; 283(2):1026-1033. doi:10.1074/jbc.M707224200

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

What is claimed:

1. A method of treating pancreatic ductal adenocarcinoma (PDA) in a subject comprising:
   diagnosing the subject as being at a pre-malignant stage or early stages of developing PDA, comprising detecting one or more microRNAs (miRNAs) as having a dysregulated expression as compared to a normal control, the miRNAs selected from one or more of miR-21, miR-16 or miR-28;
   administering to the subject a composition comprising a therapeutically effective amount of a microRNA-21 (miR-21) inhibitor, wherein the miR-21 inhibitor is an antagomir or antisense oligonucleotide; thereby treating pancreatic ductal adenocarcinoma.

2. The method of claim 1, wherein the one or more microRNAs (miRNAs) detected as having a dysregulated expression is miR-21.

3. The method of claim 1, further comprising detecting in the subject's cells increased expression of KRAS mutations (mKRAS) and/or KRAS activation as compared to a normal control.

4. The method of claim 1 wherein the subject is diagnosed as being at a pre-malignant stage.

5. The method of claim 4 wherein administering the miR-21 inhibitor intercepts developing premalignant pancreatic lesions.

6. The method of claim 1 wherein administering the miR-21 inhibitor intercepts developing premalignant pancreatic lesions.

7. A method of treating pancreatic cancer, pancreatic dysplasia, or a pre-cancerous pancreatic cancer in a subject comprising:
   administering to the subject a composition comprising a therapeutically effective amount of a microRNA-21 (miRNA-21) inhibitor, wherein the miRNA inhibitor is an antagomir, siRNA or antisense oligonucleotide or combination thereof,
   and wherein dysregulated expression of one or more microRNAs (miRNAs) selected from miR-21, miR-16 or miR-28 is detected in the subject at a pre-malignant stage or early stages of developing pancreatic cancer, as compared to a normal subject;
   thereby treating the cancer.

8. The method of claim 7 further comprising diagnosing the subject as being at a pre-malignant stage and an effective amount of microRNA-21 (miR-21) inhibitor is administered to the diagnosed subject.

9. The method of claim 8, wherein the microRNAs (miRNAs) detected as having a dysregulated expression is miR-21.

10. The method of claim 9, wherein detection of dysregulated expression of one or more miRNAs comprising miR-21 is diagnostic of a lower-grade premalignant pancreatic intraepithelial neoplasia (PanIN) (P1).

11. The method of claim 7, wherein the miRNA inhibitor is an antisense oligonucleotide.

12. The method of claim 7, wherein the miRNA inhibitor is administered systemically.

13. The method of claim 7, further comprising administering one or more chemotherapeutic agents distinct from the microRNA (miRNA) inhibitor.

14. The method of claim 7, wherein a pharmaceutical composition comprising the one or more miRNA inhibitors is administered to the subject.

15. The method of claim 7, wherein the subject has pancreatic cancer or dysplasia and comprises: ductal adenocarcinoma, pancreatic acinar cell carcinoma, neuroendocrine cell carcinoma, sarcoma of the pancreas, metastatic cancer involving the pancreas, pancreaticoblastoma, or bile duct carcinoma.

16. The method of claim 7, wherein the subject is suffering from a pre-cancerous pancreatic state that is selected from mucinous cystadenoma, serous cystadenoma, islet cell tumor, mucinous duct ectasia, intraductal papillary mucinous neoplasm, pancreatic intraepithelial neoplasia, solid and cystic papillary tumor of the pancreas.

17. The method of claim 7, wherein the microRNAs (miRNAs) detected as having a dysregulated expression is miR-21.

18. The method of claim 17, wherein detection of dysregulated expression of miR-21 is diagnostic of a lower-grade premalignant pancreatic intraepithelial neoplasia (PanIN) (P1).

19. The method of claim 7 wherein the subject is suffering from pancreatic cancer and administering the composition treats the pancreatic cancer.

20. The method of claim 7 wherein the subject is suffering from pancreatic dysplasia and administering the composition treats the pancreatic dysplasia.

21. The method of claim 7 wherein the subject is suffering from a pre-cancerous pancreatic cancer and administering the composition treats the pre-cancerous pancreatic cancer.

22. The method of claim 7 wherein administering the miR-21 inhibitor intercepts developing premalignant pancreatic lesions, thereby treating the cancer.

* * * * *